(12) United States Patent
Verschoor et al.

(10) Patent No.: US 9,133,520 B2
(45) Date of Patent: Sep. 15, 2015

(54) SINGLE NUCLEOTIDE POLYMORPHISMS (SNPS) IN GENES ASSOCIATED WITH INFLAMMATORY DISEASES

(71) Applicant: University of Guelph, Guelph (CA)

(72) Inventors: Chris P. Verschoor, Hamilton (CA); Niel A. Karrow, Belwood (CA)

(73) Assignee: University of Guelph, Guelph, Ontario (CA)

( * ) Notice: Subject to any disclaimer, the term of this patent is extended or adjusted under 35 U.S.C. 154(b) by 89 days.

(21) Appl. No.: 13/845,545

(22) Filed: Mar. 18, 2013

(65) Prior Publication Data

US 2013/0189692 A1 Jul. 25, 2013

Related U.S. Application Data

(62) Division of application No. 12/854,408, filed on Aug. 11, 2010, now Pat. No. 8,445,656.

(60) Provisional application No. 61/232,965, filed on Aug. 11, 2009.

(51) Int. Cl.
*C12Q 1/68* (2006.01)
*C12P 19/34* (2006.01)

(52) U.S. Cl.
CPC ........ *C12Q 1/6883* (2013.01); *C12Q 2600/124* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS 5,541,308 A 7/1996 Hogan
2001/0053519 A1 12/2001 Fodor et al.

OTHER PUBLICATIONS

Hegele, ARterioscler. Thromb. Vasc. Biol, 2002, 22:1058-1061.*
Ionnidis (Plost Med, 2005, 2(8):e124, 696-701).*
Verschoor (2009, Mamm Genome, 2009, 20:447-454).*
Ashwell, M.S., et al., "Detection of quantitative trait loci affecting milk production, health, and reproductive traits in Holstein cattle", J Dairy Sci., 2004, vol. 87, pp. 468-475.
Buck, G.A., et al., "Design Strategies and Performance of Custom DNA Sequencing Primers", Biotechniques, 1999, vol. 27, No. 3, p. 528-536.
Couper, K.N., et al., "IL-10: the master regulator of immunity to infection", J Immunol, 2008, vol. 180. No. 9, pp. 5771-5777.
Ding, Y., et al., "Differential IL-10R1 expression plays a critical role in IL-10-mediated immune regulation", J Immunol., 2001, vol. 167, pp. 6884-6892.
GenBank Accession NC_007313, GI 76871753, Printed Mar. 30, 2012.
Gonda, M.G., et al., "Genetic variation of *Mycobacterium avium* ssp. paratuberculosis infection in US Holsteins", J Dairy Sci., 2006, vol. 89, No. 5, pp. 1804-1812.
Hexanucleotide Mix of Boehringer Mannheim, 1997 Biochemicals Catalog.
Khalifeh, M.S. and Stabel J.R., "Upregulation of transforming growth factor-beta and interleukin-10 in cows with clinical Johne's disease", Vet Immunol Immunopatho., 2004, vol. 99, No. 1-2, pp. 39-46.
Khatkar, M.S., et al., "Quantitative trait loci mapping in dairy cattle: review and meta-analysis", Genet. Sel Evol., 2004, vol. 36, pp. 163-190.
Koets, A.P., et al., "Genetic variation of susceptibility to *Mycobacterium avium* subsp. paratuberculosis infection in dairy cattle", J Dairy Sci., 2000, vol. 83, No. 11, pp. 2702-2708.
Mortensen, H., et al., "Genetic variation and heritability of the antibody response to *Mycobacterium avium* subspecies paratuberculosis in Danish Holstein cows", J Dairy Sci., 2004, vol. 87, No. 7, pp. 2108-2113.
Oviedo-Boyso, J., et al., "Innate immune response of bovine mammary gland to pathogenic bacteria responsible for mastitis", Journal of Infection, 2007, vol. 54, No. 4, pp. 399-409.
Tao, W., et al., "Construction and application of a bovine immune-endocrine cDNA microarray", Vet Immunology and Immunopathology, 2004, vol. 101, p. 1-17.
Verschoor, C.P., et al., "Single nucleotide polymorphisms (SNPs) in pro- and anti-inflammatory cytokines are associated with health and production traits in Canadian dairy bulls", 2008 CBMRN-MRWC Joint Scientific Meeting, Nov. 3-6, 2008, Toronto, Ontario, Canada, Poster Presentation.
Verschoor, C.P., et al., "Single nucleotide polymorphisms (SNPs) in the bovine IL-10 α and β receptor, and their association with milk somatic cell score and susceptibility to *Mycobacterium avium* paratuberculosis (MAP) infection", 2008 Canadian Kennedy Conference and 2008 Canadian Society of Animal Science Annual Meeting, Guelph, Ontario, Canada, Poster Presentation.
Verschoor, C.P., et al., "SNPs in the bovine IL-10 receptor are associated with somatic cell score in Canadian dairy bulls", Mamm Genome (2009) 20:447-454.
Weiss, D.J., et al., "A critical role of interleukin-10 in the response of bovine macrophages to infection by *Mycobacterium avium* subsp paratuberculosis", Am J Vet Res., 2005, vol. 66, No. 4, pp. 721-726.
Zaahl, M.G., et al., "The -237C→T promoter polymorphism of the SLC11A1 gene is associated with a protective effect in relation to inflammatory bowel disease in the South African population", Int J Colorectal Dis., 2006, vol. 21, No. 5, pp. 402-408.

* cited by examiner

*Primary Examiner* — Sarae Bausch
(74) *Attorney, Agent, or Firm* — Bereskin & Parr LLP/S.E.N.C.R.L., s.r.l.; Micheline Gravelle

(57) ABSTRACT

The present disclosure describes the identification of single nucleotide polymorphisms (SNPs) in inflammatory diseases and uses thereof, and methods of screening for, diagnosing, identifying susceptibility to or detecting a risk of developing an inflammatory disease comprising detecting the presence or absence of at least one SNP identified in a gene associated with inflammatory disease.

3 Claims, No Drawings

SEQUENCE LISTING

```
<160> NUMBER OF SEQ ID NOS: 45

<210> SEQ ID NO 1
<211> LENGTH: 8880
<212> TYPE: DNA
<213> ORGANISM: Artificial Sequence
<220> FEATURE:
<223> OTHER INFORMATION: Bos taurus interleukin 10

<400> SEQUENCE: 1
ttgtctgcca ctcaattgtg cagttggtct gaagagaatg gaaagcaaat tgtattgatt      60
tgatcgaatg aatcctggcc cattagaatg gaaatattg gcttttattt tccaagctt     120 tctgaaaact gagaaagccc aagtctagcc aaagagaaag cagggttttt aacaaactga    180
agaaaagaga gcaagagtga gagaagaatt aaaagtggaa atggaaagta gagtcaaaaa    240
taagtctgca gtagagtccc tcccaccacc cagcgccctg actgccccca gccctcgcag    300
cctgatcccg gggccccagc cccttggcga aggggattca cagtaacagg tagggcacgg    360
tgaagcagcc cccagactcc taggggttct gacttgaaac cacaggtgca catgtgaggc    420
tctgccgctt ccaggacaca catgatgctc agaggcgatg tcatgctgaa gaaccgcaca    480
gactactggg aaactctgcg tgaaggagac agcagtgaag caatgggcat ctcccttctt    540
gctgcaggtc aggggcctcc gtgtaggtcc tctactcctt cctcggaggc caggctttga    600
tcaccctcct cccgttcatc ctcacacaga catttttgtt aaatgtctca attaaggttc    660
agctccttaa gccagcagct ctcaaagtcc ggtccaagga cagtttgtat gaggactttt    720
```

```
gtctgctaac tgtatagttc tatgaggctg gattttctcc atatgcttcc acctcaaaaa    780
cctatcacac tgggttggct gtaggagcag atgtcagagt gtaagttttt ctgttaaacc    840
aggtatgcaa agagctttgc gacagtgtca gaacagtaca ctcctctcac tgaatgtgtt    900
ctgacttaga aaacagttat ttttcattaa aaatatgcta tttattttaa catgtagtgg    960
gtttttattg tttttcttta gaacgccata catggacttt taaaaaaatt cttagttttt   1020
tttttctacc atgatcaata tcaatagaca taatctaaca aagtaaaagc tctttgaggt   1080
cttcaatact ttttaagaag gtaaagcagt cctgaatcca aatagtttga gaagagttga   1140
ctaagggaat ccaggaccac actgaacacg gtgacccact cccactccct gctctggaga   1200
atggaccacc tcgggctgga gtgtaaatga cacactcaca gtagaagtga tgcaggtcca   1260
ggacggaggg agcggccagc ttgtcccgtg ttagtgcggc cgtgcaccta agcacacatg   1320
cagtggggtt gaggatttag agttggggtc catcttacag atgaaggtcg gagcaggcaa   1380
gctgaaggca ggcatcagct ctcttaaata gggcccatga aggagactat gcttcaaggg   1440
tgccagggca ggagggtgag ccaaactatt cttttatgtc actgcagtca catcttaaag   1500
acaatataca gaagaaactc ctttctgttt gcaaatactc gagggcctga aatatttccc   1560
taaaagaaaa atatctaagc aactctcacc cccatctcca gctcctaagc ataagggcta   1620
tgcgccctgc acgtgcataa tagagttatc actgttttat ggaggaaatg cttattttca   1680
cagacttctc gcttctgctc atcactgctg ctcacatctt agacaactcc ccccggccat   1740
tggtgctgac catgaaaact cagtgatata acactcatgt cagtcaagga attaagtact   1800
gatttgagaa gaagaatgca aaaggaatcg agttctgatt tcgcctttgt tattaactac   1860
ctctagtgcc tgcttcccgg gtggcactgg tagtaaagaa cccggctgcc agtgcagaag   1920
acataagagc tccaagttcc atctgtgtgt tgggaagatc ccctggagga gggcatggca   1980
acccactcca gtattcttgc ctggagaatc ccgtggacag gggagcctgg tgggctacag   2040
tccatggggt cgcaaagagt tggacacgac tgaagcgact tagcatgcac gcatgcagtg   2100
cctgggaaag tcactttctt ttctaggcct cagtttgccc acctgtaaaa tgaagaacgt   2160
ggattttgtt gctgttgttg tttggtcact aagccctgtc cggctctttt gtgacccccat   2220
ggaccatagc ctgttaggct actttcaccc tctactttat gtgagatagt cgtcaaatgt   2280
agccacttac agccacaaag agttcaggag gcacacgctc cgtcatgctc catcatcgac   2340
aatatttagt gagagccttg gatgtgcctg gaattgtttt gagtacgagg caaacagcaa   2400
taatcaaaaa tagacatgca ccctgccccct gcggagggct gtccaatgga agagatagag   2460
atcaagcagg tgaccacgta gccatgcgag taattacaag ctggcatcag tactacagag   2520
aaaaggagca aggtgtcctg agacacaccc aggtggctca accttttcag gggaataagg   2580
aaaaactcat gtgacaaagt aagctctaag ctgagaactg aaggataaag agaagggaat   2640
cccctctctt taatctcttt ccatgcagaa aaggagagact acatgcgcaa aggccctgta   2700
gtagaataga gagcacagat catttgaaaa aaaataaaag aggaaagccg gtaaggctgg   2760
gatgcacaga gaagtggaca gtgttggaag gtgaggcaga aggaacactc agggtcagag   2820
gatgcagggg gctgtaaaca gcattaagaa cacaggtcct tattttaccc aggaagggga   2880
agtggcacgt cattgaaggg tttaagcaag gggagagtca tgatcagagt ggtgttttga   2940
aaataatccc ttgggctaca aagaagaaaa cagtttggaa aacagatttt agaatatcaa   3000
ccaggcactt gtttggagcc caggagagat aagatgttag cttgaaccag acagtcgctg   3060
```

```
ctgctgctga tgcaaataga gagaagttag acgattagaa agatgtttgt gggggctttc    3120
ctggtggtcc aggggttaag aatccaatgc aggggtgtg ggtttgatcc ctggttggga     3180
aactgagatc tcacacacca cagggcaact aagcctgcat actgcaagga agaaccaggg    3240
cagcttaagc ttaagaagga aaaaaaaagg atgtttgtga agaaaattct gcaagacctt    3300
gtaatagatt ggacataggt tattaagaga gagagaggaa ccaacaagtt atttctaggc    3360
gtccagcatg tatgttatgt tagatggtgg tcccctttcct gagtgagggc accatgtcac   3420
tggatgaagc tgagatgaag ctatgtatt agtctctgat aaaaatgggc cccatcatcc     3480
tgggtcccag cgtaaaacga aaatgttcta cagttgttaa gaatttcaag acagtgacaa    3540
cagagcaaag cacgggcccc tgagtgacca cacaagtcac gtgacttgct cagacacaag    3600
caaagtttgg ggtgtcagcc attcagggga atttgactaa actgaatcct accagaggga    3660
cagcctggga gctgaaggga tccgtctgtg cccccggctc aggaacccac tcgttactcc    3720
aggtggtcat gcagactgag cagagacagc tgtattctct gggtggcagg gtctccaaca    3780
ccttgtgtcc tggcccctgc agccaaattt ctcacgtgag aaattacaga acagggtgtc    3840
cgtcccctaa ggaaaatcca agttgcttga tttggcgcca tcgttgcaca aaggggaatt    3900
ccacgttggc tgtccaaaga tcagcccttc cgctgtggtt tgcagcgtct gccggcctag    3960
gtcctcggaa gggcacccac tccagtttgc ataaccctca ctagattcag ccaaggggcc    4020
agccccaact ggggctcctt ttaaagctct gacccacaag gtctttattc tgaagcacct    4080
caaccacaag gtcaaagtca caggcagaac cctgtcccct tgagccctcc cacccccacc    4140
cccgcggcta cacgtagagg gtgtgatgcc atagtctgcg ctctggacca ggcctgttgc    4200
cgcacagccc ctgaggaacc aacggttcag ggagccgagg ggggttattc aagggaatac    4260
tagaaatttc acactgggga aactgtggta cgttctagat gtcctgaaga agaagaaatg    4320
aaactccgtt atcagccttg aagtaatagc tgcaatgagc aagcaggagc caagccctga    4380
ggggttcttt gtggaggtcg tcagcccccct ggttccaggt gggcaccctc gcacttgcct    4440
gctttcatca ctgacctgcc tgctactgtc gtggtgaccc tgttgacagg cacactggct    4500
gaaccctgag tccagcaagc caagattcca cagggcaggc ccacgtacct ccccatcttt    4560
tttccacccc tgggacagaa ttgttgcaag gcacagggca attctaccaa gaaggttgtc    4620
cttttgctga gcatgagggt ggccacgagg tgattccttg taagcccttg tacagtctag    4680
actgcactct ctaaaatcta tccacacttt gtctgcctag agtcctctgt agctaaagtc    4740
gtgaaatgca tcagtggaac attccagaaa aatcattagg gcctttggtc tctacatatg    4800
tccctcatcc ctggcatctt aaaataacac gtaggaaagc aagacggcag aaaaggccgg    4860
ttctgttgac atttgggtgc tgcgctagct ctggacaacc tgcctctgaa cttcttgtca    4920
ctggagacca aaaaataata tcccttccct tttaaagccc tggtgagtca ggctgtcttt    4980
cctttgtagc tgaatactga cattagggaa tattttggag caggggggaga agaaagaggc     5040 atttcccctc ccacacattc ctctgatttc ccagttagtc tgcacgggaa aagattcgct    5100
taaattctat ctcatgagcg cacatcagac atctgccgtg agtctagact ggagaggtga    5160
ccgggctcag gtcatttgct ctcaaggagc cacaggcta acaagcggca cctgctctgt     5220
cttgagagcc acaggccgaa tgtgtccaga ctgatgcacc gtccatccgc agggatctgc    5280
tcactcctcc cctgctcggg ctcttctctg ggctggaaag gccagcccag atcgaacata    5340
cagacggctg acatttattt atgtctcatc tatgtaaccc tgtgagtttg gacttttttg    5400
cagtggattg taatgacttt tcagatgaat gataccttca cggtcttgag acacaggtgt    5460
```

```
catctttgtt tactgtttgg tcaacatata agcagggat cttaactttt cccaaaatgt   5520
gcatacctct tctcgtataa catcttgaca catcggttct atgagattta tggatagga    5580
agatcttgtt gtctccattt gttaattaag tgattgcatc aaggagattg cctaaatggt   5640
ctctgaccat tcagattgtg aaaattttga gaggagagag gacaacggtt tcaaatcagt   5700
ggaggaagat caacaattca acaaatgact tgaagtgatt ggctgctgct gctaagtcgc   5760
ttcagtcatg tccgactctg tgcgacccca tagatggcag cccaccaggc tctgcgaccc   5820
ctgggattct ccaggcaaga acactggagt gggttgccat ttccttctcc aatgcatgaa   5880
agtgaaaagt gaaagtgaag tcactcagtc gtgtctgacc ctcagcgacc ccatggactg   5940
cagcccacca ggctcctcca tccatgggat tttccaggca agagtactag agtggggtgc   6000
cattgccttc tccggaagta attggcaaca cgttccaaaa caagaagcc agaagctaag    6060
cctcagccta cctgatgtgt tatagaagaa agatagaaat ggctctttcc tcctcctttc   6120
acctgccatt gcgtgcatgt gtgcgtgtcc atgtctgtgt gagtgtgtct ttaatatttg   6180
aaattataag aagaaagtgg aagacactca gcataccttc ctgagttgct gtccctgttt   6240
ctctgagtgc ttgcctgtgt ctagacctgc ccaggtccag gctcctccag ccccgttccg   6300
ggctcacagg atactctcct atgcccattc aacacagga aaaggaagc tatgtgccta    6360
gcacattcca gaggccagac cctgtactca gcaccaggta tataggataa tgaaacagcg   6420
ccaggtctca gagagctcac actgtctagc agaggcagtg gggtacatgg atgatagcag   6480
cggttgttgt cgattgagta gcgtagaggg gcacagggca cggtggcaaa ctgggtaaga   6540
ggcggtctgc accacctggg tccagaagta gggcctctgg cctgagggat ctgccaggct   6600
gagtctgcac ccagaacacc catctcgag aaaggttagc cctgtggact aaagcaaaca    6660
caacccagaa aacccaggag ccaagaggtg aggggcaggg cagaagggat gcaaacccca   6720
gtccctgacc ccttcgctgt gtttcctagt ggccaaagtc agaactctta gctaagccca   6780
gtgtaaatat ggcaggagca gcaattcctg agtcagttct acacctgtat aatattttaa   6840
ttttattaaa gcattagtca atgtataatg tgttaattta tgcttcagtt atacatatat   6900
acatatatat atattcttat tcattctctt ttccattatg ttttatcatt ggatatggaa   6960
tatagtttca tgcctatttc taaaacttct ttctcccttc atgagtcttg gatttctgcc   7020
ttcacattcc ccaagggtg ggaagtgagg ctacagccca ctgctcctgc cccacgaggt    7080
acagcgtggg cctggaccct cttcctcctt cctgcccccg cccactcaca acagccccgg   7140
tatatccacc ctccttgtct ggtgcagtga gcttctttaa tggggaaggc tcagaaccca   7200
gggccaccaa tgctgatgca ggaaggcatg gaaataacag aaacactgga gacaccctac   7260
gtctggatcc acgagttacc tccccgatcc cctgcccatg tgaagcccaa aggccctcca   7320
gcaggcagga ggcaggtact gctgcaccct caggatggac agaaaacagg cagaggaggg   7380
tcaagtgact tgcccgggtt taaagcatga cggagcccag gcctcctggc ccctggatcg   7440
gagttcttca caggagaggc ggggagaagc cctgcagaa ggagtcaagg cacagtctcc    7500
accctttcct tctagtggta aggcaacatt cctcactaca tctggcttac tccacccctg   7560
cacacacacg cgcgcacaca cacacacaca cgaatgtgca catccaaaga aagacaaata   7620
acgtttcttt ggaaggagaa gggtagggaa gaggggataa agaggcctca tatccagcct   7680
ccatagaatc tcaacttatt ttccttgtta cttctgcttc tttctcccca agtgtgagtc   7740
tccagccaaa gcagttcaca acccagaaga aacctaatgc ctctttaatc caaaatttcc   7800
```

| | |
|---|---|
| attctgcacc ctggggccag tgtagagtag ggaatagttg gcctgaatgt caggcagacc | 7860 |
| tcagtgcaga ttctggctcc ctccctcggc gcccatgcac agggtacctg acacctctgt | 7920 |
| gtctcggctg gttcactgtg cagtggcggg gaggtcccgg tgactggcag gcacagcttc | 7980 |
| cagtgagcat ggactatgcc tcctaacacc ccctgaggat ggggcagcgg aggggggttag | 8040 |
| aggcatagat ctgagagtct aaatgaaccc agggctaggg aaggaatctg gagcacaccc | 8100 |
| catgcccctg actgtcctct gggaagctgg ccactttgag gagtaatcct ggaacataaa | 8160 |
| aaaaccagaa ggcagctttg aggacattta gctcacatct ttgttttctt ctggggaaac | 8220 |
| tgaggcctga agagttgagg taacttccca acccagcaag aagaagccct gaatatcaac | 8280 |
| gcaggttgag gagttgatat tatttcttaa tcacattgta ttctggaatg gccaatttgc | 8340 |
| cctcgtcact gtgatctaga gacacgtgaa tggaacccac aactgtgggt ccctgcgtac | 8400 |
| agagcagctg ttcaccccag gaaatcaact tttttttttta attaagagaa gttgaacatt | 8460 |
| attttttaaag agagagagag gtagtttctc ctaaaaatag ccatatgcag aagttcattt | 8520 |
| ttcacccatc tcttttgctt acgatgcaat atttaaaaac ttttgagtaa gaggttcacc | 8580 |
| aaatgcaaag ctggagaggt ctagggaagg gaggggcaaa gaaacctttg ccaggaaatc | 8640 |
| tgtgagtgac actgtggctt tttgtgaatg ggaggcctca cacaatataa aaggggggcac | 8700 |
| agtaggtgaa ggtctacaca acaggggctt gctcttgcaa aaccaaacca caagtccgac | 8760 |
| tcaacgaaga agacagagct ccgccatgcc cagcagctca gccctgctct gttgcctggt | 8820 |
| cttcctggct ggggtggcag ccagccgaga tgcgagcacc ctgtctgaca gcagctgtat | 8880 |

<210> SEQ ID NO 2
<211> LENGTH: 2278
<212> TYPE: DNA
<213> ORGANISM: Artificial Sequence
<220> FEATURE:
<223> OTHER INFORMATION: Bos taurus interleukin 10 receptor, alpha (IL10R_)

<400> SEQUENCE: 2

| | |
|---|---|
| atgggagcgg aagatgcacc atctggagac agtccttggt gccacctgtt tccaaagaag | 60 |
| gatttggcgc agctgctctt cctcatgatt cgcccacacc tgtctctccg aattcccagt | 120 |
| cccccctccca gcagaagtca agtcctgctt cagcacaaca ccctctca cactcggcgg | 180 |
| aatgctgggg cagtccgcgc aaccggcggc gggctcgacc tcctgacgca acggcgtgcg | 240 |
| ggcgggggcgc ctcgaggccc cgccttctg gcgtcagcct cgcggggcgt gagcggactc | 300 |
| gtcaggctga ggtttcagtc gcagccgagt agagccgctg ccggaggcga gcttctcggc | 360 |
| tccggctttg gccccggcac gggagaatgc ggtgcgccca ggatgctgtc gcaccagata | 420 |
| gtgaagctgg tggcgctcct cagcctgctc ctcggctctc gcgcgcacgg taaggatctg | 480 |
| gaactgccca gacctccatc tgcgtggttt gaagcagagt ttttccacca cgtcctctac | 540 |
| tggacaccca ttccaaatca gtctgaaagt acctattatg aagtggaact cctgaggtat | 600 |
| ggagtagagc ccacctcctg gaagtccatc cagaggtgta gccagatgct gatgatgtcc | 660 |
| tgtgatgtca ctatggagac cctgacctg tatcgcagca atggttaccg ggccagagtc | 720 |
| cgggcagtgg acggaagcca gcattccaac tggacctctc ctaacacccg cttctccatg | 780 |
| gatgaagtga ctctgacggt tgccagcgtg aagctcgagg tgcacaacag taacatcgtt | 840 |
| ggggccatcc agctcccccag gcccgaggtg gcccctgaag gcgacacata tgaaaacatc | 900 |
| ttccacaatt tccgggagta ccagattgag gttcgcaagg caccaggaca ctatgagtcc | 960 |

| catggcaagg tcaaaaacga aagcttcaaa ctcccaatcc cgagaggggt gggagagttc | 1020 |
| tgcgtcaggg tgaaaccgtc tgtgggctcc cgagtaaaca aggaggtctg gtccaaggag | 1080 |
| gagtgcatcc tgctcacctc gcagtatttc acagtgacca acatcagcat ctttctcacc | 1140 |
| ttcgtcctgc tgctctatgg agccctggcc ttctgtctga ccttccagct gtatgtgcgg | 1200 |
| cgccggggga agctgcctgc tgtcctggtc ttcaagaagc ccagtccctt caacctcatc | 1260 |
| agccagtttt cccacccaga gacccaagat accgtccaca ccctggatga ggaggccttc | 1320 |
| cccaaggtga ctccggagct gaggaactca gacatgcacg cagcaccga cagtggcttc | 1380 |
| ggcagtgcca gccgtcgct gcagaccgag gagcccagt tcctcctccc tgcctccgac | 1440 |
| ccccaggccg gggggactct ggaaaagggg atgcccagg agttggagaa cagctgtggt | 1500 |
| agtgcaggta gcagcaacag tgcagacagc gggatctgct tgccagatcc ccgcctgtgt | 1560 |
| cccggcacgg agcccagctg ggagccacag gtggggagcg acagccggga ccgggaggac | 1620 |
| agtggcattg gcctggtcca gaactctagg ggacagcctg aggatgctca gggtggctca | 1680 |
| gcttcaggcc atgtgagtcc cctgggacct gaggaacctg tggaagaaga ctcagtggca | 1740 |
| ggggccttcc agggctacct gaagcagacc cagtgcccag aggagaaggc agcccaggca | 1800 |
| ggcggcctgg aagaagagtc ttcctcaaca gaggaccttg accccaatt caggacgtgc | 1860 |
| ctggatactg aggcgggctg gcctctacca gccctggcca agggctatgt gcaacaggac | 1920 |
| cccccagaaa tgattcttgc tcctttgcag acccctgaag aacagtggga ccgaccaact | 1980 |
| gaggactggt catttctggg cttgaccagc tgtggcgacc tcggcacatc tgactggagc | 2040 |
| tttgcccatg accttgcccc tctggattgt gtgccggccc cgggcggtct cctgggcagt | 2100 |
| tttgactcag acctggtcac cctgccactg atcaccagcc tgcagtcaaa tgagtgaggc | 2160 |
| aggctaaggg cttgcttttg atttcagctg cacgctgcct ggacccagag gatccagggg | 2220 |
| ccagaagtga agcacaatgc cagtctgagc actttgctgc aggcccagta ggtgtcca | 2278 |

<210> SEQ ID NO 3
<211> LENGTH: 1800
<212> TYPE: DNA
<213> ORGANISM: Artificial Sequence
<220> FEATURE:
<223> OTHER INFORMATION: Bos taurus interleukin 10 receptor, beta
    (IL10R_)
<220> FEATURE:
<221> NAME/KEY: misc_feature
<222> LOCATION: (1042)..(1042)
<223> OTHER INFORMATION: n is a, c, g, or t

<400> SEQUENCE: 3

| ctcccccgct tgagcgccct cctgggtccc ggcgcgacta tggcgcgcag cctcctgagc | 60 |
| tggctgggcg gctgcctcct gatgtcagca ttaggaatgg ttccacctcc tgaaaatgtc | 120 |
| agaatgaatt cagttaattt caagaatatt ctacgatggg agtcacctgc ttttcccaag | 180 |
| gggaatctga cgttcacagc tcagtaccaa agttacagga aattccaaga tacatgcacg | 240 |
| agtattttgt tgacggaatg cgatttctca agtctttcca gtatggtgga ccacaccttg | 300 |
| agagtcaggg ctgaatttgc tgatgagagt tcagagtgga taaacatcac cttctgtcct | 360 |
| gtggatgaca ccactatcgg acctcccaga atgcaagtag aagcacttgc taattctttta | 420 |
| catgtgcgtt tctttgcccc aagaatcgag aatgaacctg aaccgtggac catgaggaac | 480 |
| atttataact catggactta ccatgtgcga tattggaaaa atggctctga tgaaaagttt | 540 |
| tcaatttctg gtcagtatga cttcgagttc ctccgaaatc ttgagtcaca gacaacttat | 600 |

```
tgtgttcaag ttcgagggtt tctttctgat cggaacaaag ctggagaatg gagtgagcct    660
gtctgcgagc aaacaaccat tgacgaaacc accccgtcct ggatggtggc cagcgtcctg    720
gcagcctccg tgtgcgccgc tctcctgcta ctgctcggct gcttcttcct gctgcggtgt    780
gtttacagga aggcaaggca cgccttcccc ccgaggaatt ctcttccgca gcacctgaaa    840
gagtttatga ccacccctca tcacagcact cttctcttat tctccttccc actgtctgat    900
gagaatgaag tctttgacaa actgagcgtc atcacagaag tgtctgaaag ctgcaagctg    960
aaccctgggg ccggctgcgg tctcacgacc tgacgtgggc aggggtcctt ccagctgatg   1020
tccaaggagg gagcacactc anccgggcgc agtgaccccc tccttgtcct gtctcccccc   1080
aagggcagtc agagcagcca gccagggcgg gccgagaccg cctgagtaaa ccccagatgg   1140
agagctcacg cagacgccgg ggcagcgtcc acactgccaa ggagctggac tccaaatgct   1200
cgtgtggcaa aaccttggga acttgccact ttttagaggc cttaatgatt tgaaaaaaaa   1260
gttggccact gtgatttccc tgatggtcca tcccagtggt taaaagactc catgcttcca   1320
atgcaggggg cacaggttcc atccttggtt gaaaaactaa gatcccacat atcacatgat   1380
gtggccaaaa aaaaaaaaaa caaaggttga ggttggccac cagagatatg attctcaggt   1440
atgattctcc tgtgtattca ctaatataaa aaggctttag ggaattcccc agcaggtcca   1500
gtggttagga ctccatgctt tcacagccga gggccgaggt tcagtccctg gtcacggaac   1560
tcagacctca caagccatgt ggcaaaaaaa caaaccacc aaaaaaaaaa gttttaaatg   1620
gttagaaaca aaatatata aaatgaggaa gaaagaccaa ggcaccatgg aatctgagag   1680
tgccgacatt ctgacgggag aaatggcgtc gactcagaag tcgctatcac caagcactgt   1740
acagagtgca gactctggat tctcagggac acttggactg ggtttatttt tctatgcaga   1800

<210> SEQ ID NO 4
<211> LENGTH: 1475
<212> TYPE: DNA
<213> ORGANISM: Artificial Sequence
<220> FEATURE:
<223> OTHER INFORMATION: Bos taurus transforming growth factor, beta 1
      (TGFB1)

<400> SEQUENCE: 4
ggacgagcca tcaggaaccg caaacccgac tcccgcgaag acttgacccc agatttcgga     60
cgcaccccct tgcacggccc cccaactccc cagcctctct cctgagcccc gcgcatccg    120 aggacccttc tccgggatcc gggatctctc tcagacttgc ctcagctttc ctattcaaga    180
tcacccatct ctagtaccag agctcaccca tctcggtttt ttttccgtgg ataccgaga    240 acccacccat cagagcctcc cctccagctc tgctccgttc tccctgaagg cctcaactct    300
ccccgcaaac agaccctcct accttttcct cgggagaccc ccaccaccc cagcccctgt    360 aggggcgggg cctccctctt cccaccccag cccagctcgc gctctcggct gtgccggggg    420
gcgccgcctc cccatgccg ccctcggggc tgcggctgct gccgctgctg ctgccgctgc    480
tgtggctgct aatgctgacg cctggccggc cggtcgcacg gctgtccacc tgcaagacca    540
tcgacatgga gctggtgaag cggaatgccg aaacggagga gccagaggcg gactactacg    600
ccaaggaggt cacccgcgtg ctaatggtgg aatacgcaa caaatctat gacaaaatga    660 agtctagctc gcacagcata tatatgttct tcaacacgtc cgagctccgg gaagcggtgc    720
ccgaacctgt gttgctctct cgggcagagc tgcgcctgct gaggctcaag ttaaagtgg    780 agcagcacgt ggagctgtac cagaaatata gcaacaattc ctggcgctac ctcagcaacc    840
```

```
ggctgctcgc ccccagcgac tcaccggagt ggctgtcctt tgacgtcact ggagttgtgc    900
ggcagtggct gacccgcaga gaggaaatag agggctttcg cctcagtgcc cactgttcct    960
gtgacagtaa agataacacg cttcaagtgg acattaacgg gttcagttcc ggccgccggg   1020
gtgacctcgc caccattcac ggcatgaacc ggcccttcct gctcctcatg ccacccctc    1080 tggagagggc ccagcacctg cacagctccc gccaccgccg agccctggac accaactact   1140
gcttcagctc cacagaaaag aactgctgtg ttcgtcagct ctacattgac ttccggaagg   1200
acctgggctg gaagtggatt catgaaccca aggggtacca cgccaatttc tgcctggggc   1260
cctgccctta catctggagc ctggatacac agtacagcaa ggtcctggcc ctgtacaacc   1320
agcacaaccc gggcgcttcg gcggcgccgt gctgcgtgcc tcaggcgctg agcccctgc    1380 ccatcgtgta ctacgtgggc cgcaagccca atgtggagca gttgtccaac atgatcgtgc   1440
gctcctgcaa gtgcagctga ggccccgtcc caccc                              1475
```

<210> SEQ ID NO 5
<211> LENGTH: 4280
<212> TYPE: DNA
<213> ORGANISM: Artificial Sequence
<220> FEATURE:
<223> OTHER INFORMATION: Bos taurus similar to transforming growth
      factor beta type II receptor, TGF beta R-II, transcript variant 1
      (TGFBR2)

<400> SEQUENCE: 5

```
gcacgccggg cccgacgaca ctccgcgcgc gcacccgccg gccgggccgg cctccagctc     60
cgctcccctc ggccaccggg gccccccgcg cctcgcccgc cgccaccctc cccgcggccc    120
gccgcgccac atctggctgc accgctgctg ggcgcccggc gcgggtccgg agggcgcgga    180
ggcgcggcgt acgcgctcgg gccggtctat gaggagcggc gggggctgcc atgggccggg    240
ggctgctcgg gggcctgtgg ccgctgcacg tcgtcctgtg gacgcgcatc gccagcacga    300
tcccgccgca cgttcccaag tcggttaaca gcgatatgat ggtcactgac cacaacggcg    360
ccatcaagct gtcgcagctg tgtaagttct gcgacgtgcg gtcgtccacc tgtgacaacc    420
agaagtcctg ctggagcaac tgcagcatca cggccatctg cgagaagccg gaggaggtct    480
gcgtggctgt ctggaggaag aatgatgaga acatcacgct ggagacagtc tgccatgacc    540
ccaagattgc ctaccatgga tttgtcctgg acgatgctgc ttcttcaaag tgtatcatga    600
aggaaagaaa ggggtccgga gagactttct tcatgtgctc ctgcagctcc gaagaatgca    660
atgaccacat tatcttctcc gaagagtaca ccagcagtaa ccccgacttg ctgctggtta    720
tcttccaagt gacaggcgtc agcctcctgc caccgctggg catcgccatc gcagtcatca    780
tcactttcta ctgctaccgc atccaccggc agcagaagct gagcccagcc tgggactcgg    840
gcaagccgcg caagctgatg gagttcagtg agcacctggc catcatcctg gaggacgacc    900
gctccgacat cagctccacc tgcgccaaca acatcaacca caacacggag ctgctgccca    960
tcgagctgga caccctggtg ggcaaggggc gcttcgccga ggtctacaag gccaagctga   1020
agcagaacac gtctgagcag ttcgagaccg tggccgtcaa gatcttcccc tacgaggagt   1080
atgcctcctg gaagacggag aaggacatct tctcggacat caacctcaag cacgagaaca   1140
tcctgcagtt cctgacggcc gagcagcgca agacggagct gggcaagcag tactggctca   1200
tcactgcctt ccacgccaag ggcaacctgc aggagtacct gacgcgccac gtcatcagct   1260
gggaggacct cgccggctgg gcggctcgc tggcccgcgg catcgcgcac ctgcacagcg   1320 accacccct gtgcggccgg cccaagatgc ccatcgtgca cagggacctc aagagctcca   1380
```

```
acatcctggt caagggcgac ctcacctgct gcctctgcga cttcgggctc tcactgcggc    1440
tggaccccac cctgtcagtg gatgacctgg ccaacagtgg gcaggtggga acggcgagat    1500
acatggctcc agaggtcctc gagtccagga tgaatctgga gaacgtggag tccttcaagc    1560
agacggatgt ctactccatg gccctggtgc tctgggagat gacgtctcgc tgcaacgcag    1620
tgggagaagt gaaggactat gagcctccgt tcgggtctaa ggtgcgggag catccctgtg    1680
tggaaagcat gaaggacaac gtgctgagag atcgaggccg accagagatt cccagctcct    1740
ggctcaacca ccagggcatc cagacggtgt gcgagacgct ggccgaatgc tgggaccatg    1800
accccgaggc ccggctcacg gcgcagtgcg tggccgagcg cttcagcgag ctggagcacc    1860
tggacaggct ctccgggagg agcagctcgg aggagaagat ccccgaagat ggctccctca    1920
acactaccaa atagctcttc ccgcggccgg cccagcgcgg ccgccctgtg gccaaagagc    1980
agggtcagca gaaagctgcc cctgacgatg cttcctggaa cccggggtgc tccctcccc    2040 gagctgggag ggggtggcag gaagcagctt ctgcctttga cgttgtcata ggataagctg    2100
tgttagcact tcctcaggaa atgagattga tcttacaata gccaataaca tttgcactt    2160 attaatgcct gtatataaat atgaaatagc tatgtttata tatatctata tatgtctata    2220
tatacacagc catacttgtg gaaagagatg aggacagaga ccacacgtgc ccagacgtgg    2280
gctggatggg cagcctcagc acttggcggc acgcgtgtgc tgggctcggg gcacacgggg    2340 aggggtctc tgcctttaga gagaggctcg ggtctaggag cctgctgtgc cgcattgcac    2400
ttgcttttgc aacgtagtaa ctccctgcac tgggtcctgt cctggctgtg gagccaagtg    2460
gagccgcact gtctggggac cagaccccaa ggtccccacg tcccatcatc tctcctggac    2520
tcggcactga gcgtcacacc cacgtttgtt ttgtgaacct ctgtcctcag ctagctcaga    2580
aagtctcatc gcgtcaacgt tttaagtccc atctttacc tccacaagct acagaaaaat    2640
caggacatgt tttccctacc cgtgaaattg ccacaccttg tactaatgag aaaatgttct    2700
ttttaaaaaa atccccccct ccacctatgt tactgttccc catttcctaa aagggcacag    2760
atctcccttc caggctcttt atgttcagtt tttcatcacg ctcggtttct gtcttccgct    2820
tgccatgcat cactggtggg tctcaggctc caggggact tgagcacgtt ttggccacgt    2880
ggacagtatt gaagcagcat tgtgctgcca cagtcaggac tgtccaggca ctcggaacgt    2940
gcatcttgct tggccagcac agtgtttaac aaaattgagc cactttttaa atatctggag    3000
attttgcaaa caattttggg atccccgagt gagactagat agctgatggc ttacagttct    3060
cgctgtgcca cgtcattcac agatgatggt gtagacacac ttagaaagct gctctcttcc    3120
cctgtgaaca ttcgtgtttc cccctgttct caccctagtt tgggaattaa accttctttc    3180
cccagccaag gttccctgca agaaatgtgc attcacgcaa tcattctctg gctatagagt    3240
gtcgttttga ttcccttcct ggggttaaaa ttcgaagttg gcctttttt ttttttttgga    3300 gtgacaggga ctgcctctgg atggtcccta ttaacccaaa tctcttttgc ttgtatatta    3360
aagagtgttc ccctttgcat tcaaaggggg agaccttac tccaagaagt tgttgtcatg    3420
gttaccagtc tcttagtcat acccaccttc ccaatgtttg cagaatttga atgtgggatg    3480
caggagtccc atctacagtt aggaaatatg tgtccatgtg ggtaagaaca agaatgagc    3540 tttaatcctc cataagaaac ttggtaatcc acaaacaggt gttaatgctg caaataacaa    3600
gctcttttgt aaacatgatt tgaagcttat tttcagccaa ataggtagga atattggaga    3660
gggactggca atgatcagat cagctctgct tgggttttgg aagccgcatc tcattgggt    3720
```

| | |
|---|---|
| tttagcagac acgctgaagt tgggattaag tggaattttt aggaaccctt cttggttcaa | 3780 |
| gtggactgag agagattagg cagtttggcc acaatgccat ggaagtgccc agaagtcccg | 3840 |
| tgcactttag ggctggtgat gctgtcccaa tagctgttgc tcattgacct ctagtggtga | 3900 |
| atttctagaa tactggtcca ttatgggaac tgccaagatt caaaagagct ttatcacttc | 3960 |
| tgggtcatca tcagcataaa ctggaatgta gatgatactg tggcttgttt tatgtgtgtt | 4020 |
| ttttccttat tcaagaaaaa gaccaaggaa taacattctg tagttcctaa aaatactgac | 4080 |
| tttttttcact acgtaaaggg aaagttgtat tcttttatgg aacatttcag caatactcat | 4140 |
| gtattaaaat aggaatgtga atgctgtata ctcttttttat atcaaatgtg tcaagcactt | 4200 |
| attttcattc tatgcattgt ttgtctttta tataaataaa atgtttattc gattgaataa | 4260 |
| agcaaaagta ctcaggtcag | 4280 |

<210> SEQ ID NO 6
<211> LENGTH: 2276
<212> TYPE: DNA
<213> ORGANISM: Artificial Sequence
<220> FEATURE:
<223> OTHER INFORMATION: Bos taurus solute carrier family 11
      (proton-coupled divalent metal ion transporters), member 1
      (SLC11A1)- NRAMP1

<400> SEQUENCE: 6

| | |
|---|---|
| gcttgccatg cccgtgaggg gctgcccggc acgccagcca ctcgcacaga gagtgcccga | 60 |
| gcctgcggtc ctcatgtcag gtgacacggg ccccccaaag cagggaggga ccagatatgg | 120 |
| ctccatctcc agcccaccca gtccagagcc acagcaagca cctcccggag ggacctacct | 180 |
| aagtgagaag atccccattc cggatacaga atcgggtaca ttcagcctga ggaagctgtg | 240 |
| ggccttcacg gggcctggat tcctcatgag catcgcattc ctggacccag aaacattga | 300 |
| gtcggatctt caggctgggg ctgtggctgg attcaaactg ctctgggtgc tgctgtgggc | 360 |
| cacagtgttg ggcttgcttt gccagcgact ggctgcccgg ctgggcgtgg tgacaggcaa | 420 |
| ggacttgggc gaggtctgcc atctctacta ccctaaggtg ccccgcattc tcctctggct | 480 |
| gaccatcgag ctagccatcg tgggctcaga catgcaggaa gtcattggca cagctattgc | 540 |
| attcagtctg ctctccgccg gacgaatccc actctggggt ggtgtcctca tcaccgtcgt | 600 |
| ggacactttc ttcttcctct tcctcgataa ctacggggttg cggaagctgg aagccttttt | 660 |
| tggatttctt attaccataa tggccttgac cttcggctat gagtacgtgg tggctcagcc | 720 |
| tgctcaggga gcattgcttc agggcctgtt cctgccctcg tgcccaggct gtggccagcc | 780 |
| cgagctgctg caagccgtgg gcatcattgg cgccatcatc atgccccaca catctacct | 840 |
| gcattcctcc ctggtcaagt ctcgagaggt agaccggtcc cggcgggcgg acatccgaga | 900 |
| ggccaacatg tacttcctga ttgaagccac catcgccctg tctgtctcct tcctcatcaa | 960 |
| cctgtttgtc atggctgtct ttgggcaagc cttctacaag caaaccaacc aggctgcgtt | 1020 |
| caacatctgt gccgacagca gcctccacga ctacgcgccg atctttccca ggaacaacct | 1080 |
| gaccgtggca gtggacattt accaaggagg cgtgatcctg ggctgcctct tggtcctcc | 1140 |
| agccctgtac atctgggccg tgggtctcct ggctgctggg cagagctcca ccatgaccgg | 1200 |
| cacctacgcg ggacagtttg tgatggaggg cttcctgaag ctgcggtggt cacgcttcgc | 1260 |
| ccgagtcctg ctcactcgct cctcgccat cctgcccact gtgctcctgg ctgtcttcag | 1320 |
| ggacttgcgg gacctgtcag gcctcaacga cctgctcaat gtgctgcaga gcctgctgct | 1380 |
| tcccttcgct gtgctgccca tcctcacctt caccagcatg cccgccctga tgcaggagtt | 1440 |

```
tgccaatggc ctggtgagca aagttatcac ttcctccatc atggtgctgg tctgcgccgt   1500
caacctttac ttcgtgatca gctacttgcc cagcctcccc cacccctgcct acttcagcct   1560 tgtagcactg ctggccgcag cctacctggg cctcaccact acctggtct ggacctgtct    1620 catcacccag ggagccactc ttctggccca cagttcccac caacgcttcc tgtatgggct    1680
tcctgaagag gatcaggaga aggggaggac ctcgggatga gctcccacca gggcctggcc    1740
acgggtggaa tgagtgggca cagtggcctg tcagacaagg gtgtgtgtgt gtgtgtgtgt    1800
gtgtatgtgt gtgaaggcag caagacagac agggagttct ggaagctggc caacgtgagt    1860
tccagaggga cctgtgtgtg tgtgacacac tggcctgcca gacaagggtg tgtgtgtgtg    1920
tgtgtgtgtg tgtgcatgca cagcaagacg agagggagt tctggaaggc agccaacgtg    1980
agttccatag ggacctgcta tttcctagct cagatctcag tgttcttgac tataaaatgg    2040
ggacacctac cttggagtgg ttgtaaataa gacacttgaa cgcagagcct agcacttcag    2100
atttaaaaac aaaagaatca taattccaaa agttactgag cactatcaca ggagtgacct    2160
gacagaccca cccagtctag ggtgggaccc aggctccaaa ctgatttaaa ataagagtct    2220
gaaaatgcta aataaatgct gttgtgctta gtccccgaat ccatatgact agtaga         2276

<210> SEQ ID NO 7
<211> LENGTH: 8880
<212> TYPE: DNA
<213> ORGANISM: Artificial Sequence
<220> FEATURE:
<223> OTHER INFORMATION: Bos taurus interleukin 10

<400> SEQUENCE: 7
ttgtctgcca ctcaattgtg cagttggtct gaagagaatg gaaagcaaat tgtattgatt     60
tgatcgaatg aatcctggcc cattagaatg gaaaatattg gcttttattt tccaagctttt    120 tctgaaaact gagaaagccc aagtctagcc aaagagaaag cagggttttt aacaaactga    180
agaaaagaga gcaagagtga gagaagaatt aaaagtggaa atggaaagta gagtcaaaaa    240
taagtctgca gtagagtccc tcccaccacc cagcgccctg actgccccca gccctcgcag    300
cctgatcccg gggccccagc cccttggcga aggggattca cagtaacagg tagggcacgg    360
tgaagcagcc cccagactcc tagggggttct gacttgaaaac cacaggtgca catgtgaggc   420
tctgccgctt ccaggacaca catgatgctc agaggcgatg tcatgctgaa gaaccgcaca    480
gactactggg aaactctgcg tgaaggagac agcagtgaag caatgggcat ctcccttctt    540
gctgcaggtc aggggcctcc gtgtaggtcc tctactcctt cctcggaggc caggctttga    600
tcaccctcct cccgttcatc ctcacacaga cattttttgtt aaatgtctca attaaggttc    660
agctccttaa gccagcagct ctcaaagtcc ggtccaagga cagtttgtat gaggactttt    720
gtctgctaac tgtatagttc tatgaggctg gattttctcc atatgcttcc acctcaaaaa    780
cctatcacac tgggttggct gtaggagcag atgtcagagt gtaagttttt ctgttaaacc    840
aggtatgcaa agagctttgc gacagtgtca gaacagtaca ctcctctcac tgaatgtgtt    900
ctgacttaga aaacagttat ttttcattaa aaatatgcta tttattttaa catgtagtgg    960
gtttttatcg ttttttcttta gaacgccata catggacttt taaaaaaatt tcttagtttt   1020
tttttctacc atgatcaata tcaatagaca taatctaaca aagtaaaagc tctttgaggt   1080
cttcaatact tttaagaag gtaaagcagt cctgaatcca aatagtttga aagagttga    1140 ctaagggaat ccaggaccac actgaacacg gtgacccact cccactccct gctctggaga   1200
```

```
atggaccacc tcgggctgga gtgtaaatga cacactcaca gtagaagtga tgcaggtcca    1260
ggacggaggg agcggccagc ttgtcccgtg ttagtgcggc cgtgcaccta agcacacatg    1320
cagtggggtt gaggatttag agttggggtc catcttacag atgaaggtcg gagcaggcaa    1380
gctgaaggca ggcatcagct ctcttaaata gggcccatga aggagactat gcttcaaggg    1440
tgccagggca ggagggtgag ccaaactatt cttttatgtc actgcagtca catcttaaag    1500
acaatataca gaagaaactc ctttctgttt gcaaatactc gagggcctga aatatttccc    1560
taaaagaaaa atatctaagc aactctcacc cccatctcca gctcctaagc ataagggcta    1620
tgcgccctgc acgtgcataa tagagttatc actgttttat ggaggaaatg cttatttca    1680 cagacttctc gcttctgctc atcactgctg ctcacatctt agacaactcc ccccggccat    1740
tggtgctgac catgaaaact cagtgatata cactcatgt cagtcaagga attaagtact    1800
gatttgagaa gaagaatgca aaaggaatcg agttctgatt tcgcctttgt tattaactac    1860
ctctagtgcc tgcttcccgg gtggcactgg tagtaaagaa cccggctgcc agtgcagaag    1920
acataagagc tccaagttcc atctgtgtgt tgggaagatc ccctggagga gggcatggca    1980
acccactcca gtattcttgc ctggagaatc ccgtggacag gggagcctgg tgggctacag    2040
tccatggggt cgcaaagagt tggacacgac tgaagcgact tagcatgcac gcatgcagtg    2100
cctgggaaag tcactttctt ttctaggcct cagtttgccc acctgtaaaa tgaagaacgt    2160
ggattttgtt gctgttgttg tttggtcact aagccctgtc cggctctttt gtgaccccat    2220
ggaccatagc ctgttaggct actttcaccc tctactttat gtgagatagt cgtcaaatgt    2280
agccacttac agccacaaag agttcaggag gcacacgctc cgtcatgctc catcatcgac    2340
aatatttagt gagagccttg gatgtgcctg gaattgtttt gagtacgagg caaacagcaa    2400
taatcaaaaa tagacatgca ccctgcccct gcggagggct gtccaatgga agagatagag    2460
atcaagcagg tgaccacgta gccatgcgag taattacaag ctggcatcag tactacagag    2520
aaaaggagca aggtgtcctg agacacaccc aggtggctca accttttcag gggaataagg    2580
aaaaactcat gtgacaaagt aagctctaag ctgagaactg aaggataaag agaagggaat    2640
cccctctctt taatctcttt ccatgcagaa aaggagagact acatgcgcaa aggccctgta    2700
gtagaataga gagcacagat catttgaaaa aaaataaaag aggaaagccg gtaaggctgg    2760
gatgcacaga gaagtggaca gtgttggaag gtgaggcaga aggaacactc agggtcagag    2820
gatgcagggg gctgtaaaca gcattaagaa cacaggtcct tattttaccc aggaagggga    2880
agtggcacgt cattgaaggg tttaagcaag gggagagtca tgatcagagt ggtgttttga    2940
aaataatccc ttgggctaca agaagaaaa cagtttggaa aacagatttt agaatatcaa    3000
ccaggcactt gtttggagcc caggagagat aagatgttag cttgaaccag acagtcgctg    3060
ctgctgctga tgcaaataga gagaagttag acgattagaa agatgtttgt ggggctttc    3120 ctggtggtcc aggggttaag aatccaatgc aggggtgtg ggtttgatcc ctggttggga    3180
aactgagatc tcacacacca cagggcaact aagcctgcat actgcaagga agaaccaggg    3240
cagcttaagc ttaagaagga aaaaaaagg atgtttgtga agaaaattct gcaagacctt    3300
gtaatagatt ggacataggt tattaagaga gagagaggaa ccaacaagtt atttctaggc    3360
gtccagcatg tatgttatgt tagatggtgg tccccttcct gagtgagggc accatgtcac    3420
tggatgaagc tgagatgaag ctatgtattt agtctctgat aaaaatgggc cccatcatcc    3480
tgggtcccag cgtaaaacga aaatgttcta cagttgttaa gaatttcaag acagtgacaa    3540
cagagcaaag cacgggcccc tgagtgacca cacaagtcac gtgacttgct cagacacaag    3600
```

-continued

```
caaagtttgg ggtgtcagcc attcagggga atttgactaa actgaatcct accagaggga    3660
cagcctggga gctgaaggga tccgtctgtg cccccggctc aggaacccac tcgttactcc    3720
aggtggtcat gcagactgag cagagacagc tgtattctct gggtggcagg gtctccaaca    3780
ccttgtgtcc tggcccctgc agccaaattt ctcacgtgag aaattacaga acagggtgtc    3840
cgtcccctaa ggaaaatcca agttgcttga tttggcgcca tcgttgcaca aagggaatt     3900 ccacgttggc tgtccaaaga tcagcccttc cgctgtggtt tgcagcgtct gccggcctag    3960
gtcctcggaa gggcacccac tccagtttgc ataaccctca ctagattcag ccaaggggcc    4020
agccccaact ggggctcctt ttaaagctct gacccacaag gtctttattc tgaagcacct    4080
caaccacaag gtcaaagtca caggcagaac cctgtcccct tgagccctcc caccccacc     4140 cccgcggcta cacgtagagg gtgtgatgcc atagtctgcg ctctggacca ggcctgttgc    4200
cgcacagccc ctgaggaacc aacggttcag ggagccgagg ggggttattc aagggaatac    4260
tagaaatttc acactgggga aactgtggta cgttctagat gtcctgaaga agaagaaatg    4320
aaactccgtt atcagccttg aagtaatagc tgcaatgagc aagcaggagc caagccctga    4380
ggggttcttt gtggaggtcg tcagcccct ggttccaggt gggcaccctc gcacttgcct     4440
gctttcatca ctgacctgcc tgctactgtc gtggtgaccc tgttgacagg cacactggct    4500
gaaccctgag tccagcaagc caagattcca cagggcaggc ccacgtacct ccccatcttt    4560
tttccacccc tgggacagaa ttgttgcaag gcacagggca attctaccaa gaaggttgtc    4620
cttttgctga gcatgagggt ggccacgagg tgattccttg taagcccttg tacagtctag    4680
actgcactct ctaaaatcta tccacacttt gtctgcctag agtcctctgt agctaaagtc    4740
gtgaaatgca tcagtggaac attccagaaa aatcattagg gcctttggtc tctacatatg    4800
tccctcatcc ctggcatctt aaaataacac gtaggaaagc aagacggcag aaaaggccgg    4860
ttctgttgac atttgggtgc tgcgctagct ctggacaacc tgcctctgaa cttcttgtca    4920
ctggagacca aaaaataata tccctttcct tttaaagccc tggtgagtca ggctgtcttt    4980
cctttgtagc tgaatactga cattagggaa tattttggag cagggggaga agaaagaggc    5040
atttcccctc ccacacattc ctctgatttc ccagttagtc tgcacgggaa aagattcgct    5100
taaattctat ctcatgagcg cacatcagac atctgccgtg agtctagact ggagaggtga    5160
ccgggctcag gtcatttgct ctcaaggagc ccacaggcta acaagcggca cctgctctgt    5220
cttgagagcc acaggccgaa tgtgtccaga ctgatgcacc gtccatccgc agggatctgc    5280
tcactcctcc cctgctcggg ctcttctctg ggctggaaag gccagcccag atcgaacata    5340
cagacggctg acatttattt atgtctcatc tatgtaaccc tgtgagtttg gacttttg      5400 cagtggattg taatgacttt tcagatgaat gataccttca cggtcttgag acacaggtgt    5460
catctttgtt tactgtttgg tcaacatata agcagggat cttaacttttt cccaaaatgt    5520 gcatacctct tctcgtataa catcttgaca catcggttct atgagattta tggatagggaa  5580 agatcttgtt gtctccattt gttaattaag tgattgcatc aaggagattg cctaaatggt    5640
ctctgaccat tcagattgtg aaatttttga gaggagagag gacaacggtt tcaaatcagt    5700
ggaggaagat caacaattca acaaatgact tgaagtgatt ggctgctgct gctaagtcgc    5760
ttcagtcatg tccgactctg tgcgacccca tagatggcag cccaccaggc tctgcgaccc    5820
ctgggattct ccaggcaaga acactggagt gggttgccat ttccttctcc aatgcatgaa    5880
agtgaaaagt gaaagtgaag tcactcagtc gtgtctgacc ctcagcgacc ccatggactg    5940
```

```
cagcccacca ggctcctcca tccatgggat tttccaggca agagtactag agtggggtgc    6000
cattgccttc tccggaagta attggcaaca cgttccaaaa caaagaagcc agaagctaag    6060
cctcagccta cctgatgtgt tatagaagaa agatagaaat ggctctttcc tcctcctttc    6120
acctgccatt gcgtgcatgt gtgcgtgtcc atgtctgtgt gagtgtgtct ttaatatttg    6180
aaattataag aagaaagtgg aagacactca gcataccttc ctgagttgct gtccctgttt    6240
ctctgagtgc ttgcctgtgt ctagacctgc ccaggtccag gctcctccag ccccgttccg    6300
ggctcacagg atactctcct atgcccattc aacacagga aaaggaagc tatgtgccta     6360 gcacattcca gaggccagac cctgtactca gcaccaggta tataggataa tgaaacagcg    6420
ccaggtctca gagagctcac actgtctagc agaggcagtg gggtacatgg atgatagcag    6480
cggttgttgt cgattgagta gcgtagaggg cacagggca cggtggcaaa ctgggtaaga     6540
ggcggtctgc accacctggg tccagaagta gggcctctgg cctgagggat ctgccaggct    6600
gagtctgcac ccagaacacc catctcagag aaaggttagc cctgtggact aaagcaaaca    6660
caacccagaa aacccaggag ccaagaggtg agggcaggg cagaagggat gcaaaaccca     6720
gtccctgacc ccttcgctgt gtttcctagt ggccaaagtc agaactctta gctaagccca    6780
gtgtaaatat ggcaggagca gcaattcctg agtcagttct acacctgtat aatattttaa    6840
ttttattaaa gcattagtca atgtataatg tgttaattta tgcttcagtt atacatatat    6900
acatatatat atattcttat tcattctctt ttccattatg ttttatcatt ggatatggaa    6960
tatagtttca tgcctatttc taaaacttct ttctcccttc atgagtcttg gatttctgcc    7020
ttcacattcc ccaaggggtg ggaagtgagg ctacagccca ctgctcctgc cccacgaggt    7080
acagcgtggg cctggaccct cttcctcctt cctgccccg cccactcaca acagccccgg     7140
tatatccacc ctccttgtct ggtgcagtga gcttctttaa tggggaaggc tcagaaccca    7200
gggccaccaa tgctgatgca ggaaggcatg gaaataacag aaacactgga gacaccctac    7260
gtctggatcc acgagttacc tccccgatcc cctgcccatg tgaagcccaa aggccctcca    7320
gcaggcagga ggcaggtact gctgcaccct caggatggac agaaaacagg cagaggaggg    7380
tcaagtgact tgcccggggtt taaagcatga cggagcccag gcctcctggc ccctggatcg    7440
gagttcttca caggagaggc ggggagaagc ccctgcagaa ggagtcaagg cacagtctcc    7500
accctttcct tctagtggta aggcaacatt cctcactaca tctggcttac tccacccctg    7560
cacacacacg cgcgcacaca cacacacaca cgaatgtgca catccaaaga aagacaaata    7620
acgtttcttt ggaaggagaa gggtagggaa gaggggataa agaggcctca tatccagcct    7680
ccatagaatc tcaacttatt ttccttgtta cttctgcttc tttctcccca agtgtgagtc    7740
tccagccaaa gcagttcaca acccagaaga aacctaatgc ctctttaatc caaaatttcc    7800
attctgcacc ctggggccag tgtagagtag ggaatagttg gcctgaatgt caggcagacc    7860
tcagtgcaga ttctggctcc ctccctcggc gcccatgcac agggtacctg acacctctgt    7920
gtctcggctg gttcactgtg cagtggcggg gaggtcccgg tgactggcag gcacagcttc    7980
cagtgagcat ggactatgcc tcctaacacc ccctgaggat ggggcagcgg aggggggttag    8040 aggcatagat ctgagagtct aaatgaaccc agggctaggg aaggaatctg agcacaccc     8100 catgcccctg actgtcctct gggaagctgg ccactttgag gagtaatcct ggaacataaa    8160
aaaaccagaa ggcagctttg aggacattta gctcacatct tgttttctt ctggggaaac     8220 tgaggcctga gagttgagg taacttccca acccagcaag aagaagccct gaatatcaac     8280
gcaggttgag gagttgatat tatttcttaa tcacattgta ttctggaatg gccaatttgc    8340
```

```
cctcgtcact gtgatctaga gacacgtgaa tggaacccac aactgtgggt ccctgcgtac    8400
agagcagctg ttcaccccag gaaatcaact tttttttta attaagagaa gttgaacatt    8460
atttttaaag agagagagag gtagtttctc ctaaaaatag ccatatgcag aagttcattt    8520
ttcacccatc tcttttgctt acgatgcaat atttaaaaac ttttgagtaa gaggttcacc    8580
aaatgcaaag ctggagaggt ctagggaagg gaggggcaaa gaaacctttg ccaggaaatc    8640
tgtgagtgac actgtggctt tttgtgaatg ggaggcctca cacaatataa aaggggcac     8700 agtaggtgaa ggtctacaca acaggggctt gctcttgcaa aaccaaacca caagtccgac    8760
tcaacgaaga agacagagct ccgccatgcc cagcagctca gccctgctct gttgcctggt    8820
cttcctggct ggggtggcag ccagccgaga tgcgagcacc ctgtctgaca gcagctgtat    8880
```

<210> SEQ ID NO 8
<211> LENGTH: 8880
<212> TYPE: DNA
<213> ORGANISM: Artificial Sequence
<220> FEATURE:
<223> OTHER INFORMATION: Bos taurus interleukin 10

<400> SEQUENCE: 8

```
ttgtctgcca ctcaattgtg cagttggtct gaagagaatg gaaagcaaat tgtattgatt      60
tgatcgaatg aatcctggcc cattagaatg gaaatattg gcttttattt tccaagcttt     120
tctgaaaact gagaaagccc aagtctagcc aaagagaaag caggttttt aacaaactga     180 agaaaagaga gcaagagtga gagaagaatt aaaagtggaa atggaaagta gagtcaaaaa    240
taagtctgca gtagagtccc tcccaccacc cagcgccctg actgcccca gccctcgcag     300 cctgatcccg gggccccagc cccttggcga aggggattca cagtaacagg tagggcacgg    360
tgaagcagcc cccagactcc tagggggttct gacttgaaac cacaggtgca catgtgaggc    420
tctgccgctt ccaggacaca catgatgctc agagcgatg tcatgctgaa gaaccgcaca     480
gactactggg aaactctgcg tgaaggagac agcagtgaag caatgggcat ctcccttctt    540
gctgcaggtc aggggcctcc gtgtaggtcc tctactcctt cctcggaggc caggctttga    600
tcaccctcct cccgttcatc ctcacacaga cattttttgtt aaatgtctca attaaggttc    660
agctccttaa gccagcagct ctcaaagtcc ggtccaagga cagtttgtat gaggactttt    720
gtctgctaac tgtatagttc tatgaggctg gattttctcc atatgcttcc acctcaaaaa    780
cctatcacac tgggttggct gtaggagcag atgtcagagt gtaagttttt ctgttaaacc    840
aggtatgcaa agagctttgc gacagtgtca gaacagtaca ctcctctcac tgaatgtgtt    900
ctgacttaga aaacagttat ttttcattaa aaatatgcta tttattttaa catgtagtgg    960 gttttttattg ttttttcttta gaacgccata catggacttt taaaaaaatt tcttagttt    1020 tttttctacc atgatcaata tcaatagaca taatctaaca aagtaaaagc tctttgaggt    1080
cttcaatact ttttaagaag gtaaagcagt cctgaatcca aatagtttga gaagagttga    1140
ctaagggaat ccaggaccac actgaacacg gtgacccact cccactccct gctctggaga    1200
atggaccacc tcgggctggc gtgtaaatga cacactcaca gtagaagtga tgcaggtcca    1260
ggacggaggg agcggccagc ttgtcccgtg ttagtgcggc cgtgcaccta gcacacatg     1320 cagtggggtt gaggatttag agttggggtc catcttacag atgaaggtcg gagcaggcaa    1380
gctgaaggca ggcatcagct ctcttaaata gggcccatga aggagactat gcttcaaggg    1440
tgccagggca ggagggtgag ccaaactatt cttttatgtc actgcagtca catcttaaag    1500
```

| | |
|---|---|
| acaatataca gaagaaactc ctttctgttt gcaaatactc gagggcctga aatatttccc | 1560 |
| taaaagaaaa atatctaagc aactctcacc cccatctcca gctcctaagc ataagggcta | 1620 |
| tgcgccctgc acgtgcataa tagagttatc actgttttat ggaggaaatg cttattttca | 1680 |
| cagacttctc gcttctgctc atcactgctg ctcacatctt agacaactcc ccccggccat | 1740 |
| tggtgctgac catgaaaact cagtgatata acactcatgt cagtcaagga attaagtact | 1800 |
| gatttgagaa gaagaatgca aaaggaatcg agttctgatt tcgcctttgt tattaactac | 1860 |
| ctctagtgcc tgcttcccgg gtggcactgg tagtaaagaa cccggctgcc agtgcagaag | 1920 |
| acataagagc tccaagttcc atctgtgtgt tgggaagatc ccctggagga gggcatggca | 1980 |
| acccactcca gtattcttgc ctggagaatc ccgtggacag gggagcctgg tgggctacag | 2040 |
| tccatgggt cgcaaagagt tggacacgac tgaagcgact tagcatgcac gcatgcagtg | 2100 |
| cctgggaaag tcactttctt ttctaggcct cagtttgccc acctgtaaaa tgaagaacgt | 2160 |
| ggattttgtt gctgttgttg tttggtcact aagccctgtc cggctctttt gtgaccccat | 2220 |
| ggaccatagc ctgttaggct actttcaccc tctactttat gtgagatagt cgtcaaatgt | 2280 |
| agccacttac agccacaaag agttcaggag gcacacgctc cgtcatgctc catcatcgac | 2340 |
| aatatttagt gagagccttg gatgtgcctg gaattgtttt gagtacgagg caaacagcaa | 2400 |
| taatcaaaaa tagacatgca ccctgcccct gcggagggct gtccaatgga agagatagag | 2460 |
| atcaagcagg tgaccacgta gccatgcgag taattacaag ctggcatcag tactacagag | 2520 |
| aaaaggagca aggtgtcctg agacacaccc aggtggctca acctttcag gggaataagg | 2580 |
| aaaaactcat gtgacaaagt aagctctaag ctgagaactg aaggataaag agaagggaat | 2640 |
| cccctctctt taatctcttt ccatgcagaa aagggagact acatgcgcaa aggccctgta | 2700 |
| gtagaataga gagcacagat catttgaaaa aaaataaaag aggaaagccg gtaaggctgg | 2760 |
| gatgcacaga gaagtggaca gtgttggaag gtgaggcaga aggaacactc agggtcagag | 2820 |
| gatgcagggg gctgtaaaca gcattaagaa cacaggtcct tattttaccc aggaagggga | 2880 |
| agtggcacgt cattgaaggg tttaagcaag gggagagtca tgatcagagt ggtgtttga | 2940 |
| aaataatccc ttgggctaca agaagaaaa cagtttggaa aacagatttt agaatatcaa | 3000 |
| ccaggcactt gtttggagcc caggagagat aagatgttag cttgaaccag acagtcgctg | 3060 |
| ctgctgctga tgcaaataga gagaagttag acgattagaa agatgtttgt ggggctttc | 3120 |
| ctggtggtcc agggggttaag aatccaatgc aggggggtgtg ggtttgatcc ctggttggga | 3180 |
| aactgagatc tcacacacca cagggcaact aagcctgcat actgcaagga agaaccaggg | 3240 |
| cagcttaagc ttaagaagga aaaaaaagg atgtttgtga agaaaattct gcaagacctt | 3300 |
| gtaatagatt ggacataggt tattaagaga gagagaggaa ccaacaagtt atttctaggc | 3360 |
| gtccagcatg tatgttatgt tagatggtgg tcccctcct gagtgagggc accatgtcac | 3420 |
| tggatgaagc tgagatgaag ctatgtattt agtctctgat aaaaatgggc cccatcatcc | 3480 |
| tgggtcccag cgtaaaacga aaatgttcta cagttgttaa gaatttcaag acagtgacaa | 3540 |
| cagagcaaag cacgggcccc tgagtgacca cacaagtcac gtgacttgct cagacacaag | 3600 |
| caaagtttgg ggtgtcagcc attcagggga atttgactaa actgaatcct accagaggga | 3660 |
| cagcctggga gctgaaggga tccgtctgtg cccccggctc aggaacccac tcgttactcc | 3720 |
| aggtggtcat gcagactgag cagagacagc tgtattctct gggtggcagg gtctccaaca | 3780 |
| ccttgtgtcc tggcccctgc agccaaattt ctcacgtgag aaattacaga acagggtgtc | 3840 |
| cgtcccctaa ggaaaatcca agttgcttga tttggcgcca tcgttgcaca aaggggaatt | 3900 |

```
ccacgttggc tgtccaaaga tcagcccttc cgctgtggtt tgcagcgtct gccggcctag    3960
gtcctcggaa gggcacccac tccagtttgc ataaccctca ctagattcag ccaaggggcc    4020
agccccaact ggggctcctt ttaaagtctc gacccacaag gtctttattc tgaagcacct    4080
caaccacaag gtcaaagtca caggcagaac cctgtcccct tgagccctcc caccccacc    4140
cccgcggcta cacgtagagg gtgtgatgcc atagtctgcg ctctggacca ggcctgttgc    4200
cgcacagccc ctgaggaacc aacggttcag ggagccgagg ggggttattc aagggaatac    4260
tagaaatttc acactgggga aactgtggta cgttctagat gtcctgaaga agaagaaatg    4320
aaactccgtt atcagccttg aagtaatagc tgcaatgagc aagcaggagc caagccctga    4380
ggggttcttt gtggaggtcg tcagccccct ggttccaggt gggcaccctc gcacttgcct    4440
gctttcatca ctgacctgcc tgctactgtc gtggtgaccc tgttgacagg cacactggct    4500
gaaccctgag tccagcaagc caagattcca cagggcaggc ccacgtacct ccccatcttt    4560
tttccacccc tgggacagaa ttgttgcaag gcacagggca attctaccaa gaaggttgtc    4620
cttttgctga gcatgagggt ggccacgagg tgattccttg taagcccttg tacagtctag    4680
actgcactct ctaaaatcta tccacacttt gtctgcctag agtcctctgt agctaaagtc    4740
gtgaaatgca tcagtggaac attccagaaa aatcattagg gcctttggtc tctacatatg    4800
tccctcatcc ctggcatctt aaaataacac gtaggaaagc aagacggcag aaaaggccgg    4860
ttctgttgac atttgggtgc tgcgctagct ctggacaacc tgcctctgaa cttcttgtca    4920
ctggagacca aaaataata tccctttcct tttaaagccc tggtgagtca ggctgtcttt    4980
cctttgtagc tgaatactga cattagggaa tattttggag caggggaga agaaagaggc    5040
atttcccctc ccacacattc ctctgatttc ccagttagtc tgcacgggaa aagattcgct    5100
taaattctat ctcatgagcg cacatcagac atctgccgtg agtctagact ggagaggtga    5160
ccgggctcag gtcatttgct ctcaaggagc cacaggcta acaagcggca cctgtgctgt    5220
cttgagagcc acaggccgaa tgtgtccaga ctgatgcacc gtccatccgc agggatctgc    5280
tcactcctcc cctgctcggg ctcttctctg ggctggaaag gccagcccag atcgaacata    5340
cagacggctg acatttattt atgtctcatc tatgtaaccc tgtgagtttg ggactttttg    5400
cagtggattg taatgacttt tcagatgaat gataccttca cggtcttgag acacaggtgt    5460
catctttgtt tactgtttgg tcaacatata agcagggat cttaactttt cccaaaatgt    5520
gcatacctct tctcgtataa catcttgaca catcggttct atgagattta tggatagga    5580
agatcttgtt gtctccattt gttaattaag tgattgcatc aaggagattg cctaaatggt    5640
ctctgaccat tcagattgtg aaaattttga gaggagagag gacaacggtt tcaaatcagt    5700
ggaggaagat caacaattca acaaatgact tgaagtgatt ggctgctgct gctaagtcgc    5760
ttcagtcatg tccgactctg tgcgaccca tagatggcag cccaccaggc tctgcgaccc    5820
ctgggattct ccaggcaaga acactggagt ggggttgccat ttccttctcc aatgcatgaa    5880
agtgaaaagt gaaagtgaag tcactcagtc gtgtctgacc ctcagcgacc ccatggactg    5940
cagcccacca ggctcctcca tccatgggat tttccaggca agagtactag agtggggtgc    6000
cattgccttc tccggaagta attggcaaca cgttccaaaa caagaagcc agaagctaag    6060
cctcagccta cctgatgtgt tatagaagaa agatagaaat ggctctttcc tcctcctttc    6120
acctgccatt gcgtgcatgt gtgcgtgtcc atgtctgtgt gagtgtgtct ttaatatttg    6180
aaattataag aagaaagtgg aagacactca gcataccttc ctgagttgct gtccctgttt    6240
```

```
ctctgagtgc ttgcctgtgt ctagacctgc ccaggtccag gctcctccag ccccgttccg   6300
ggctcacagg atactctcct atgcccattc caacacagga aaaggaagc tatgtgccta    6360 gcacattcca gaggccagac cctgtactca gcaccaggta tataggataa tgaaacagcg   6420
ccaggtctca gagagctcac actgtctagc agaggcagtg gggtacatgg atgatagcag   6480
cggttgttgt cgattgagta gcgtagaggg gcacagggca cggtggcaaa ctgggtaaga   6540
ggcggtctgc accacctggg tccagaagta gggcctctgg cctgagggat ctgccaggct   6600
gagtctgcac ccagaacacc catctcagag aaaggttagc cctgtggact aaagcaaaca   6660
caacccagaa aacccaggag ccaagaggtg aggggcaggg cagaagggat gcaaaaccca   6720
gtccctgacc ccttcgctgt gtttcctagt ggccaaagtc agaactctta gctaagccca   6780
gtgtaaatat ggcaggagca gcaattcctg agtcagttct acacctgtat aatattttaa   6840
ttttattaaa gcattagtca atgtataatg tgttaattta tgcttcagtt atacatatat   6900
acatatatat atattcttat tcattctctt ttccattatg ttttatcatt ggatatggaa   6960
tatagtttca tgcctatttc taaaacttct ttctcccttc atgagtcttg gatttctgcc   7020
ttcacattcc caaggggtg ggaagtgagg ctacagccca ctgctcctgc cccacgaggt    7080
acagcgtggg cctggaccct cttcctcctt cctgcccccg cccactcaca acagcccgg    7140 tatatccacc ctccttgtct ggtgcagtga gcttctttaa tggggaaggc tcagaaccca   7200
gggccaccaa tgctgatgca ggaaggcatg gaaataacag aaacactgga cacccctac    7260 gtctggatcc acgagttacc tccccgatcc cctgcccatg tgaagcccaa aggccctcca   7320
gcaggcagga ggcaggtact gctgcaccct caggatggac agaaaacagg cagaggaggg   7380
tcaagtgact tgcccgggtt taaagcatga cggagcccag gcctcctggc ccctggatcg   7440
gagttcttca caggagaggc ggggagaagc ccctgcagaa ggagtcaagg cacagtctcc   7500 acccttttcct tctagtggta aggcaacatt cctcactaca tctggcttac tccacccctg   7560
cacacacacg cgcgcacaca cacacacaca cgaatgtgca catccaaaga aagacaaata   7620
acgtttcttt ggaaggagaa gggtagggaa gaggggataa agaggcctca tatccagcct   7680
ccatagaatc tcaacttatt ttccttgtta cttctgcttc tttctcccca agtgtgagtc   7740
tccagccaaa gcagttcaca acccagaaga aacctaatgc ctctttaatc caaaatttcc   7800
attctgcacc ctggggccag tgtagagtag ggaatagttg gcctgaatgt caggcagacc   7860
tcagtgcaga ttctggctcc ctccctcggc gcccatgcac agggtacctg acacctctgt   7920
gtctcggctg gttcactgtg cagtggcggg gaggtcccgg tgactggcag gcacagcttc   7980
cagtgagcat ggactatgcc tcctaacacc ccctgaggat ggggcagcgg aggggttag    8040 aggcatagat ctgagagtct aaatgaaccc agggctaggg aaggaatctg gagcacaccc   8100
catgcccctg actgtcctct gggaagctgg ccactttgag gagtaatcct ggaacataaa   8160
aaaaccagaa ggcagctttg aggacattta gctcacatct ttgttttctt ctggggaaac   8220
tgaggcctga agagttgagg taacttccca acccagcaag aagaagccct gaatatcaac   8280
gcaggttgag gagttgatat tatttcttaa tcacattgta ttctggaatg gccaatttgc   8340
cctcgtcact gtgatctaga gacacgtgaa tggaacccac aactgtgggt ccctgcgtac   8400
agagcagctg ttcaccccag gaaatcaact ttttttttta attaagagaa gttgaacatt   8460 attttttaaag agagagagag gtagtttctc ctaaaaatag ccatatgcag aagttcattt   8520
ttcacccatc tctttttgctt acgatgcaat atttaaaaac ttttgagtaa gaggttcacc   8580
aaatgcaaag ctggagaggt ctagggaagg gaggggcaaa gaaacctttg ccaggaaatc   8640
```

```
tgtgagtgac actgtggctt tttgtgaatg ggaggcctca cacaatataa aaggggcac    8700 agtaggtgaa ggtctacaca acaggggctt gctcttgcaa aaccaaacca caagtccgac   8760
tcaacgaaga agacagagct ccgccatgcc cagcagctca gccctgctct gttgcctggt   8820
cttcctggct ggggtggcag ccagccgaga tgcgagcacc ctgtctgaca gcagctgtat   8880
```

<210> SEQ ID NO 9
<211> LENGTH: 2278
<212> TYPE: DNA
<213> ORGANISM: Artificial Sequence
<220> FEATURE:
<223> OTHER INFORMATION: Bos taurus interleukin 10 receptor, alpha (IL10R_)

<400> SEQUENCE: 9

```
atgggagcgg aagatgcacc atctggagac agtccttggt gccacctgtt ccaaagaag     60 gatttggcgc agctgctctt cctcatgatt cgcccacacc tgtctctccg aattcccagt   120 cccccctccca gcagaagtca agtcctgctt cagcacaaca cccctctca cactcggcgg   180 aatgctgggg cagtccgcgc aaccggcggc gggctcgacc tcctgacgca acggcgtgcg   240
ggcggggcgc ctcgaggccc cgcccttctg gcgtcagcct cgcggggcgt gagcggactc   300
gtcaggctga ggtttcagtc gcagccgagt agagccgctg ccggaggcga gcttctcggc   360
tccggctttg gccccggcac gggagaatgc ggtgcgccca ggatgctgtc gcaccagata   420
gtgaagctgg tggcgctcct cagcctgctc ctcggctctc gcgcgcacgg taaggatctg   480
gaactgccca gacctccatc tgcgtggttt gaagcagagt ttttccacca cgtcctctac   540
tggacaccca ttccaaatca gtctgaaagt acctattatg aagtggaact cctgaggtat   600
ggagtagagc ccacctcctg gaagtccatc cagaggtgta gccagatgct gatgatgtcc   660
tgtgatgtca ctatggagac cctggacctg tatcgcagca atggttaccg ggccagagtc   720
cgggcagtgg acggaagcca gcattccaac tggacctctc ctaacacccg cttctccatg   780
gatgaagtga ctctgacggt tgccagcgtg aagctcgagg tgcacaacag taacatcgtt   840
ggggccatcc agctccccag gcccgaggtg gcccctgaag gcgacacata tgaaaacatc   900
ttccacaatt tccgggagta ccagattgag gttcgcaagg caccaggaca ctatgagtcc   960
catggcaagg tcaaaaacga aagcttcaaa ctcccaatcc cgagagggggt gggagagttc  1020 tgcgtcaggg tgaaaccgtc tgtgggatcc cgagtaaaca aggaggtctg gtccaaggag  1080
gagtgcatcc tgctcacctc gcagtatttc acagtgacca acatcagcat ctttctcacc  1140
ttcgtcctgc tgctctatgg agccctggcc ttctgtctga ccttccagct gtatgtgcgg  1200
cgccggggga agctgcctgc tgtcctggtc ttcaagaagc ccagtccctt caacctcatc  1260
agccagtttt cccacccaga gacccaagat accgtccaca ccctggatga ggaggccttc  1320
cccaaggtga ctccggagct gaggaactca gacatgacg gcagcaccga cagtggcttc  1380
ggcagtgcca agccgtcgct gcagaccgag gagccccagt cctcctcccc tgcctccgac  1440
ccccaggccg gggggactct ggaaaagggg atgcccagg agttggagaa cagctgtggt  1500
agtgcaggta gcagcaacag tgcagacagc gggatctgct tgccagatcc ccgcctgtgt  1560
cccggcacgg agcccagctg ggagccacag gtggggagcg acagccggga ccggggaggac  1620 agtggcattg gcctggtcca gaactctagg ggacagcctg aggatgctca gggtggctca  1680
gcttcaggcc atgtgagtcc cctgggacct gaggaacctg tggaagaaga ctcagtggca  1740
ggggccttcc agggctacct gaagcagacc cagtgcccag aggagaaggc agcccaggca  1800
```

-continued

| | |
|---|---|
| ggcggcctgg aagaagagtc ttcctcaaca gaggaccttg accccaatt caggacgtgc | 1860 |
| ctggatactg aggcgggctg gcctctacca gccctggcca agggctatgt gcaacaggac | 1920 |
| cccccagaaa tgattcttgc tcctttgcag acccctgaag aacagtggga ccgaccaact | 1980 |
| gaggactggt catttctggg cttgaccagc tgtggcgacc tcggcacatc tgactggagc | 2040 |
| tttgcccatg accttgcccc tctggattgt gtgccggccc cgggcggtct cctgggcagt | 2100 |
| tttgactcag acctggtcac cctgccactg atcaccagcc tgcagtcaaa tgagtgaggc | 2160 |
| aggctaaggg cttgcttttg atttcagctg cacgctgcct ggacccagag gatccagggg | 2220 |
| ccagaagtga agcacaatgc cagtctgagc actttgctgc aggcccagta ggtgtcca | 2278 |

<210> SEQ ID NO 10
<211> LENGTH: 2278
<212> TYPE: DNA
<213> ORGANISM: Artificial Sequence
<220> FEATURE:
<223> OTHER INFORMATION: Bos taurus interleukin 10 receptor, alpha
      (IL10R_)

<400> SEQUENCE: 10

| | |
|---|---|
| atgggagcgg aagatgcacc atctggagac agtccttggt gccacctgtt ccaaagaag | 60 |
| gatttggcgc agctgctctt cctcatgatt cgcccacacc tgtctctccg aattcccagt | 120 |
| cccccctccca gcagaagtca gtcctgcttc agcacaacaa cccctctca cactcggcgg | 180 |
| aatgctgggg cagtccgcgc aaccggcggc gggctcgacc tcctgacgca acggcgtgcg | 240 |
| ggcggggcgc ctcgaggccc cgcccttctg gcgtcagcct cgcggggcgt gagcggactc | 300 |
| gtcaggctga ggtttcagtc gcagccgagt agagccgctg ccggaggcga gcttctcggc | 360 |
| tccggctttg gccccggcac gggagaatgc ggtgcgccca ggatgctgtc gcaccagata | 420 |
| gtgaagctgg tggcgctcct cagcctgctc ctcggctctc gcgcgcacgg taaggatctg | 480 |
| gaactgccca gacctccatc tgcgtggttt gaagcagagt ttttccacca cgtcctctac | 540 |
| tggacaccca ttccaaatca gtctgaaagt acctattatg aagtggaact cctgaggtat | 600 |
| ggagtagagc ccacctcctg gaagtccatc cagaggtgta gccagatgct gatgatgtcc | 660 |
| tgtgatgtca ctatggagac cctggacctg tatcgcagca atggttaccg ggccagagtc | 720 |
| cgggcagtgg acgaagcca gcattccaac tggacctctc ctaacacccg cttctccatg | 780 |
| gatgaagtga ctctgacggt tgccagcgtg aagctcgagg tgcacaacag taacatcgtt | 840 |
| ggggccatcc agctccccag gcccgaggtg gcccctgaag gcgacacata tgaaaacatc | 900 |
| ttccacaatt tccgggagta ccagattgag gttcgcaagg caccaggaca ctatgagtcc | 960 |
| catggcaagg tcaaaaacga aagcttcaaa ctcccaatcc gagaggggt gggagagttc | 1020 |
| tgcgtcaggg tgaaaccgtc tgtgggctcc gagtaaaca aggaggtctg gtccaaggag | 1080 |
| gagtgcatcc tgctcacctc gcagtatttc acagtgacca acatcagcat ctttctcacc | 1140 |
| ttcgtcctgc tgctctatgg agccctggcc ttctgtctga ccttccagct gtatgtgcgg | 1200 |
| cgccggggga agctgcctgc tgtcctggtc ttcaagaagc ccagtcccct caacctcatc | 1260 |
| agccagttttt cccacccaga gacccaagat accgtccaca ccctggatga ggaggccttc | 1320 |
| cccaaggtga ctccggagct gaggaactca gacatgcacg gcagcaccga cagtggcttc | 1380 |
| ggcagtgcca agccgtcact gcagaccgag gagcccagt tcctcctccc tgcctccgac | 1440 |
| cccaggccg ggggactct ggaaaagggg atgcccagg agttggagaa cagctgtggt | 1500 |
| agtgcaggta gcagcaacag tgcagacagc gggatctgct tgccagatcc ccgcctgtgt | 1560 |

| | |
|---|---|
| cccggcacgg agcccagctg ggagccacag gtggggagcg acagccggga ccggaggac | 1620 |
| agtggcattg gcctggtcca gaactctagg ggacagcctg aggatgctca gggtggctca | 1680 |
| gcttcaggcc atgtgagtcc cctgggacct gaggaacctg tggaagaaga ctcagtggca | 1740 |
| ggggccttcc agggctacct gaagcagacc cagtgcccag aggagaaggc agcccaggca | 1800 |
| ggcggcctgg aagaagagtc ttcctcaaca gaggaccttg accccaatt caggacgtgc | 1860 |
| ctggatactg aggcgggctg gcctctacca gccctggcca agggctatgt gcaacaggac | 1920 |
| cccccagaaa tgattcttgc tcctttgcag acccctgaag aacagtggga ccgaccaact | 1980 |
| gaggactggt catttctggg cttgaccagc tgtggcgacc tcggcacatc tgactggagc | 2040 |
| tttgcccatg accttgcccc tctggattgt gtgccggccc cgggcggtct cctgggcagt | 2100 |
| tttgactcag acctggtcac cctgccactg atcaccagcc tgcagtcaaa tgagtgaggc | 2160 |
| aggctaaggg cttgcttttg atttcagctg cacgctgcct ggacccagag gatccagggg | 2220 |
| ccagaagtga agcacaatgc cagtctgagc actttgctgc aggcccagta ggtgtcca | 2278 |

```
<210> SEQ ID NO 11
<211> LENGTH: 2278
<212> TYPE: DNA
<213> ORGANISM: Artificial Sequence
<220> FEATURE:
<223> OTHER INFORMATION: Bos taurus interleukin 10 receptor, alpha
      (IL10R_)

<400> SEQUENCE: 11
```

| | |
|---|---|
| atgggagcgg aagatgcacc atctggagac agtccttggt gccacctgtt tccaaagaag | 60 |
| gatttggcgc agctgctctt cctcatgatt cgcccacacc tgtctctccg aattcccagt | 120 |
| cccccctccca gcagaagtca agtcctgctt cagcacaaca cccctctca cactcggcgg | 180 |
| aatgctgggg cagtccgcgc aaccggcggc gggctcgacc tcctgacgca acggcgtgcg | 240 |
| ggcggggcgc ctcgaggccc cgcccttctg gcgtcagcct cgcggggcgt gagcggactc | 300 |
| gtcaggctga ggtttcagtc gcagccgagt agagccgctg ccggaggcga gcttctcggc | 360 |
| tccggctttg gccccggcac gggagaatgc ggtgcgccca ggatgctgtc gcaccagata | 420 |
| gtgaagctgg tggcgctcct cagcctgctc ctcggctctc gcgcgcacgg taaggatctg | 480 |
| gaactgccca gacctccatc tgcgtggttt gaagcagagt ttttccacca cgtcctctac | 540 |
| tggacaccca ttccaaatca gtctgaaagt acctattatg aagtggaact cctgaggtat | 600 |
| ggagtagagc ccacctcctg gaagtccatc cagaggtgta gccagatgct gatgatgtcc | 660 |
| tgtgatgtca ctatggagac cctggacctg tatcgcagca atggttaccg ggccagagtc | 720 |
| cgggcagtgg acggaagcca gcattccaac tggacctctc ctaacacccg cttctccatg | 780 |
| gatgaagtga ctctgacggt tgccagcgtg aagctcgagg tgcacaacag taacatcgtt | 840 |
| ggggccatcc agctccccag gcccgaggtg gcccctgaag gcgacacata tgaaaacatc | 900 |
| ttccacaatt tccgggagta ccagattgag gttcgcaagg caccaggaca ctatgagtcc | 960 |
| catggcaagg tcaaaaacga aagcttcaaa ctcccaatcc gagaggggt gggagagttc | 1020 |
| tgcgtcaggg tgaaaccgtc tgtgggctcc gagtaaaca aggaggtctg gtccaaggag | 1080 |
| gagtgcatcc tgctcaccct gcagtatttc acagtgacca acatcagcat ctttctcacc | 1140 |
| ttcgtcctgc tgctctatgg agccctggcc ttctgtctga ccttccagct gtatgtgcgg | 1200 |
| cgccggggga agctgcctgc tgtcctggtc ttcaagaagc cagtccctt caacctcatc | 1260 |
| agccagtttt cccacccaga gacccaagat accgtccaca ccctggatga ggaggccttc | 1320 |

```
cccaaggtga ctccggagct gaggaactca gacatgcacg gcagcaccga cagtggcttc    1380
ggcagtgcca agccgtcgct gcagaccgag gagccccagt tcctcctccc tgcctccgac    1440
ccccaggccg gggggactct ggaaaagggg atgccccagg agttggagaa cagctgtggt    1500
agtgcaggta gtagcaacag tgcagacagc gggatctgct tgccagatcc ccgcctgtgt    1560
cccggcacgg agcccagctg ggagccacag gtggggagcg acagccggga ccggaggac    1620 agtggcattg gcctggtcca gaactctagg ggacagcctg aggatgctca gggtggctca    1680
gcttcaggcc atgtgagtcc cctgggacct gaggaacctg tggaagaaga ctcagtggca    1740
ggggccttcc agggctacct gaagcagacc cagtgcccag aggagaaggc agcccaggca    1800
ggcggcctgg aagaagagtc ttcctcaaca gaggaccttg accccaatt caggacgtgc    1860 ctggatactg aggcgggctg gcctctacca gccctggcca agggctatgt gcaacaggac    1920
cccccagaaa tgattcttgc tcctttgcag accccctgaag aacagtggga ccgaccaact    1980
gaggactggt catttctggg cttgaccagc tgtggcgacc tcggcacatc tgactggagc    2040
tttgcccatg accttgcccc tctggattgt gtgccggccc cgggcggtct cctgggcagt    2100
tttgactcag acctggtcac cctgccactg atcaccagcc tgcagtcaaa tgagtgaggc    2160
aggctaaggg cttgcttttg atttcagctg cacgctgcct ggacccagag gatccagggg    2220
ccagaagtga agcacaatgc cagtctgagc actttgctgc aggcccagta ggtgtcca     2278
```

<210> SEQ ID NO 12
<211> LENGTH: 2278
<212> TYPE: DNA
<213> ORGANISM: Artificial Sequence
<220> FEATURE:
<223> OTHER INFORMATION: Bos taurus interleukin 10 receptor, alpha
      (IL10R_)

<400> SEQUENCE: 12

```
atgggagcgg aagatgcacc atctggagac agtccttggt gccacctgtt tccaaagaag      60
gatttggcgc agctgctctt cctcatgatt cgcccacacc tgtctctccg aattcccagt     120 cccccctccca gcagaagtca agtcctgctt cagcacaaca acccctctca cactcggcgg     180
aatgctgggg cagtccgcgc aaccggcggc gggctcgacc tcctgacgca acggcgtgcg     240
ggcggggcgc tcgaggccc cgccttctg gcgtcagcct cgcggggcgt gagcggactc     300
gtcaggctga ggtttcagtc gcagccgagt agagccgctg ccggaggcga gcttctcggc     360
tccggctttg gccccggcac gggagaatgc ggtgcgccca ggatgctgtc gcaccagata     420
gtgaagctgg tggcgctcct cagcctgctc ctcggctctc gcgcgcacgg taaggatctg     480
gaactgccca gacctccatc tgcgtggttt gaagcagagt ttttccacca cgtcctctac     540
tggacaccca ttccaaatca gtctgaaagt acctattatg aagtggaact cctgaggtat     600
ggagtagagc ccacctcctg gaagtccatc cagaggtgta gccagatgct gatgatgtcc     660
tgtgatgtca ctatggagac cctggacctg tatcgcagca atggttaccg ggccagagtc     720
cgggcagtgg acggaagcca gcattccaac tggacctctc ctaacacccg cttctccatg     780
gatgaagtga ctctgacggt tgccagcgtg aagctcgagg tgcacaacag taacatcgtt     840
ggggccatcc agctccccag gcccgaggtg gcccctgaag gcgacacata tgaaaacatc     900
ttccacaatt tccgggagta ccagattgag gttcgcaagg caccaggaca ctatgagtcc     960
catggcaagg tcaaaaacga aagcttcaaa ctcccaatcc cgagagggt gggagagttc    1020 tgcgtcaggg tgaaaccgtc tgtgggctcc cgagtaaaca aggaggtctg gtccaaggag    1080
```

```
gagtgcatcc tgctcacctc gcagtatttc acagtgacca acatcagcat ctttctcacc    1140
ttcgtcctgc tgctctatgg agccctggcc ttctgtctga ccttccagct gtatgtgcgg    1200
cgccggggga agctgcctgc tgtcctggtc ttcaagaagc ccagtccctt caacctcatc    1260
agccagtttt cccacccaga gacccaagat accgtccaca ccctggatga ggaggccttc    1320
cccaaggtga ctccggagct gaggaactca gacatgcacg gcagcaccga cagtggcttc    1380
ggcagtgcca agccgtcgct gcagaccgag gagccccagt tcctcctccc tgcctccgac    1440
ccccaggccg gggggactct ggaaaagggg atgcccagg agttggagaa cagctgtggt     1500
agtgcaggta gcagcaacag tgcagacagc gggatctgct tgccagatcc ccgcctgtgt    1560
cccggcacgg agcccagctg ggagccacag gtggggagtg acagccggga ccgggaggac    1620
agtggcattg gcctggtcca gaactctagg ggacagcctg aggatgctca gggtggctca    1680
gcttcaggcc atgtgagtcc cctgggacct gaggaacctg tggaagaaga ctcagtggca    1740
ggggccttcc agggctacct gaagcagacc cagtgcccag aggagaaggc agcccaggca    1800
ggcggcctgg aagaagagtc ttcctcaaca gaggaccttg accccaatt caggacgtgc     1860
ctggatactg aggcgggctg gcctctacca gccctggcca agggctatgt gcaacaggac    1920
cccccagaaa tgattcttgc tcctttgcag accccgaag acagtggga ccgaccaact      1980
gaggactggt catttctggg cttgaccagc tgtggcgacc tcggcacatc tgactggagc    2040
tttgcccatg accttgcccc tctggattgt gtgccggccc cgggcggtct cctgggcagt    2100
tttgactcag acctggtcac cctgccactg atcaccagcc tgcagtcaaa tgagtgaggc    2160
aggctaaggg cttgcttttg atttcagctg cacgctgcct ggacccagag gatccagggg    2220
ccagaagtga agcacaatgc cagtctgagc actttgctgc aggcccagta ggtgtcca     2278
```

<210> SEQ ID NO 13
<211> LENGTH: 2278
<212> TYPE: DNA
<213> ORGANISM: Artificial Sequence
<220> FEATURE:
<223> OTHER INFORMATION: Bos taurus interleukin 10 receptor, alpha (IL10R_)

<400> SEQUENCE: 13

```
atgggagcgg aagatgcacc atctggagac agtccttggt gccacctgtt tccaaagaag     60
gatttggcgc agctgctctt cctcatgatt cgcccacacc tgtctctccg aattcccagt    120
ccccctccca gcagaagtca agtcctgctt cagcacaaca ccccctctca cactcggcgg    180
aatgctgggg cagtccgcgc aaccggcggc gggctcgacc tcctgacgca acggcgtgcg    240
ggcggggcgc ctcgaggccc cgccttctg gcgtcagcct cgcggggcgt gagcggactc     300
gtcaggctga ggtttcagtc gcagccgagt agagccgctg ccggaggcga gcttctcggc    360
tccggctttg gccccggcac gggagaatgc ggtgcgccca ggatgctgtc gcaccagata    420
gtgaagctgg tggcgctcct cagcctgctc ctcggctctc gcgcgcacgg taaggatctg    480
gaactgccca gacctccatc tgcgtggttt gaagcagagt ttttccacca cgtcctctac    540
tggacaccca ttccaaatca gtctgaaagt acctattatg aagtggaact cctgaggtat    600
ggagtagagc ccacctcctg gaagtccatc cagaggtgta gccagatgct gatgatgtcc    660
tgtgatgtca ctatggagac cctggacctg tatcgcagca atggttaccg ggccagagtc    720
cgggcagtgg acggaagcca gcattccaac tggacctctc taacacccg cttctccatg    780
gatgaagtga ctctgacggt tgccagcgtg aagctcgagg tgcacaacag taacatcgtt    840
```

```
ggggccatcc agctccccag gcccgaggtg gcccctgaag gcgacacata tgaaaacatc    900
ttccacaatt tccgggagta ccagattgag gttcgcaagg caccaggaca ctatgagtcc    960
catggcaagg tcaaaaacga aagcttcaaa ctcccaatcc gagaggggt gggagagttc    1020 tgcgtcaggg tgaaaccgtc tgtgggctcc cgagtaaaca aggaggtctg gtccaaggag    1080
gagtgcatcc tgctcacctc gcagtatttc acagtgacca acatcagcat ctttctcacc    1140
ttcgtcctgc tgctctatgg agccctggcc ttctgtctga ccttccagct gtatgtgcgg    1200
cgccggggga agctgcctgc tgtcctggtc ttcaagaagc ccagtcccct caacctcatc    1260
agccagtttt cccacccaga gacccaagat accgtccaca ccctggatga ggaggccttc    1320
cccaaggtga ctccggagct gaggaactca gacatgcacg gcagcaccga cagtggcttc    1380
ggcagtgcca gccgtcgct gcagaccgag gagccccagt tcctcctccc tgcctccgac    1440
ccccaggccg gggggactct ggaaaagggg atgcccagg agttggagaa cagctgtggt    1500
agtgcaggta gcagcaacag tgcagacagc gggatctgct tgccagatcc ccgcctgtgt    1560
cccggcacgg agcccagctg ggagccacag gtggggagcg acagccggga ccgggaggac    1620
agtggcattg gcctggtcca gaactctagg ggacagcctg aggatgctca gggtggctca    1680
gcctcaggcc atgtgagtcc cctgggacct gaggaacctg tggaagaaga ctcagtggca    1740
ggggccttcc agggctacct gaagcagacc cagtgcccag aggagaaggc agcccaggca    1800
ggcggcctgg aagaagagtc ttcctcaaca gaggaccttg accccaatt caggacgtgc    1860 ctggatactg aggcgggctg gcctctacca gccctggcca agggctatgt gcaacaggac    1920
cccccagaaa tgattcttgc tcctttgcag acccctgaag aacagtggga ccgaccaact    1980
gaggactggt catttctggg cttgaccagc tgtggcgacc tcggcacatc tgactgagc    2040 tttgcccatg accttgcccc tctggattgt gtgccggccc cgggcggtct cctgggcagt    2100
tttgactcag acctggtcac cctgccactg atcaccagcc tgcagtcaaa tgagtgaggc    2160
aggctaaggg cttgcttttg atttcagctg cacgctgcct ggacccagag gatccagggg    2220
ccagaagtga agcacaatgc cagtctgagc actttgctgc aggcccagta ggtgtcca     2278
```

<210> SEQ ID NO 14
<211> LENGTH: 2278
<212> TYPE: DNA
<213> ORGANISM: Artificial Sequence
<220> FEATURE:
<223> OTHER INFORMATION: Bos taurus interleukin 10 receptor, alpha (IL10R_)

<400> SEQUENCE: 14

```
atgggagcgg aagatgcacc atctggagac agtccttggt gccacctgtt tccaaagaag    60
gatttggcgc agctgctctt cctcatgatt cgcccacacc tgtctctccg aattcccagt    120 cccccctccca gcagaagtca agtcctgctt cagcacaaca ccccctctca cactcggcgg    180
aatgctgggg cagtccgcgc aaccggcggc gggctcgacc tcctgacgca acggcgtgcg    240
ggcggggcgc ctcgaggccc cgcccttctg gcgtcagcct cgcggggcgt gagcggactc    300
gtcaggctga ggtttcagtc gcagccgagt agagccgctg ccgaggcga gcttctcggc    360 tccggctttg gccccggcac gggagaatgc ggtgcgccca ggatgctgtc gcaccagata    420
gtgaagctgg tggcgctcct cagcctgctc ctcggctctc gcgcgcacgg taaggatctg    480
gaactgccca gacctccatc tgcgtggttt gaagcagagt ttttccacca cgtcctctac    540
tggacaccca ttccaaatca gtctgaaagt acctattatg aagtggaact cctgaggtat    600
```

```
ggagtagagc ccacctcctg gaagtccatc cagaggtgta gccagatgct gatgatgtcc      660
tgtgatgtca ctatggagac cctggacctg tatcgcagca atggttaccg ggccagagtc      720
cgggcagtgg acggaagcca gcattccaac tggacctctc ctaacacccg cttctccatg      780
gatgaagtga ctctgacggt tgccagcgtg aagctcgagg tgcacaacag taacatcgtt      840
ggggccatcc agctccccag gcccgaggtg gcccctgaag gcgacacata tgaaaacatc      900
ttccacaatt tccgggagta ccagattgag gttcgcaagg caccaggaca ctatgagtcc      960
catggcaagg tcaaaaacga aagcttcaaa ctcccaatcc cgagaggggt gggagagttc     1020
tgcgtcaggg tgaaaccgtc tgtgggctcc cgagtaaaca aggaggtctg gtccaaggag     1080
gagtgcatcc tgctcacctc gcagtatttc acagtgacca acatcagcat ctttctcacc     1140
ttcgtcctgc tgtctctatg gagccctggc cttctgtctga ccttccagct gtatgtgcgg     1200
cgccggggga agctgcctgc tgtcctggtc ttcaagaagc ccagtcccct caacctcatc     1260
agccagtttt cccacccaga gacccaagat accgtccaca ccctggatga ggaggccttc     1320
cccaaggtga ctccggagct gaggaactca gacatgcacg gcagcaccga cagtggcttc     1380
ggcagtgcca gccgtcgct gcagaccgag gagccccagt tcctcctccc tgcctccgac     1440
ccccaggccg gggggactct ggaaaagggg atgcccagg agttggagaa cagctgtggt     1500
agtgcaggta gcagcaacag tgcagacagc gggatctgct tgccagatcc ccgcctgtgt     1560
cccggcacgg agcccagctg ggagccacag gtggggagcg acagccggga ccgggaggac     1620
agtggcattg gcctggtcca gaactctagg ggacagcctg aggatgctca gggtggctca     1680
gcttcaggcc atgtgagtcc cctgggacct gagggacctg tggaagaaga ctcagtggca     1740
ggggccttcc agggctacct gaagcagacc cagtgcccag aggagaaggc agcccaggca     1800
ggcggcctgg aagaagagtc ttcctcaaca gaggaccttg accccaatt caggacgtgc     1860 ctggatactg aggcgggctg gcctctacca gccctggcca agggctatgt gcaacaggac     1920
cccccagaaa tgattcttgc tcctttgcag acccctgaag aacagtggga ccgaccaact     1980
gaggactggt catttctggg cttgaccagc tgtggcgacc tcggcacatc tgactgagc      2040 tttgcccatg accttgcccc tctggattgt gtgccggcc cgggcggtct cctgggcagt     2100
tttgactcag acctggtcac cctgccactg atcaccagcc tgcagtcaaa tgagtgaggc     2160
aggctaaggg cttgcttttg atttcagctg cacgctgcct ggaccagag gatccagggg     2220 ccagaagtga agcacaatgc cagtctgagc actttgctgc aggcccagta ggtgtcca       2278
```

<210> SEQ ID NO 15
<211> LENGTH: 1800
<212> TYPE: DNA
<213> ORGANISM: Artificial Sequence
<220> FEATURE:
<223> OTHER INFORMATION: Bos taurus interleukin 10 receptor, beta (IL10R_)
<220> FEATURE:
<221> NAME/KEY: misc_feature
<222> LOCATION: (1042)..(1042)
<223> OTHER INFORMATION: n is a, c, g, or t
<400> SEQUENCE: 15

```
ctcccccgct tgagcgccct cctgggtccc ggcgcgacta tggcgcgcag cctcctgagc       60
tggctgggcg gctgcctcct gatgtcagca ttaggaatgg ttccacctcc tgaaaatgtc      120
agaatgaatt cagttaattt caagaatatt ctacgtggg agtcacctgc ttttcccaag      180
gggaatctga cgttcacagc tcagtaccaa agttacagga aattccaaga tacatgcacg      240
```

```
agtattttgt tgacggaatg cgatttctca agtctttcca agtatggtga ccacaccttg    300
agagtcaggg ctgaatttgc tgatgagagt tcagagtgga taaacatcac cttctgtcct    360
gtggatgaca ccactatcgg acctcccaga atgcaagtag aagcacttgc taattcttta    420
catgtgcgtt tctttgcccc aagaatcgag aatgaacctg aaccgtggac catgaggaac    480
atttataact catggactta ccatgtgcga tattggaaaa atggctctga tgaaaagttt    540
ttaatttctg gtcagtatga cttcgagttc ctccgaaatc ttgagtcaca gacaacttat    600
tgtgttcaag ttcgagggtt tctttctgat cggaacaaag ctggagaatg gagtgagcct    660
gtctgcgagc aaacaaccat tgacgaaacc accccgtcct ggatggtggc cagcgtcctg    720
gcagcctccg tgtgcgccgc tctcctgcta ctgctcggct gcttcttcct gctgcggtgt    780
gtttacagga aggcaaggca cgccttcccc ccgaggaatt ctcttccgca gcacctgaaa    840
gagtttatga ccacccctca tcacagcact cttctcttat tctccttccc actgtctgat    900
gagaatgaag tctttgacaa actgagcgtc atcacagaag tgtctgaaag ctgcaagctg    960
aaccctgggg ccggctgcgg tctcacgacc tgacgtgggc aggggtcctt ccagctgatg   1020
tccaaggagg agcacactc anccgggcgc agtgaccccc tccttgtcct gtctcccccc   1080
aagggcagtc agagcagcca gccagggcgg gccgagaccg cctgagtaaa ccccagatgg   1140
agagctcacg cagacgccgg ggcagcgtcc acactgccaa ggagctggac tccaaatgct   1200
cgtgtggcaa aaccttggga acttgccact ttttagaggc cttaatgatt tgaaaaaaaa   1260
gttggccact gtgatttccc tgatggtcca tcccagtggt taaaagactc catgcttcca   1320 atgcagggg cacaggttcc atccttggtt gaaaaactaa gatcccacat atcacatgat   1380
gtggccaaaa aaaaaaaaaa caaaggttga ggttggccac cagagatatg attctcaggt   1440
atgattctcc tgtgtattca ctaatataaa aaggctttag ggaattcccc agcaggtcca   1500
gtggttagga ctccatgctt tcacagccga gggccgaggt tcagtccctg gtcacggaac   1560
tcagacctca caagccatgt ggcaaaaaaa caaaccacc aaaaaaaaaa gttttaaatg   1620
gttagaaaca aaaatatata aaatgaggaa gaaagaccaa ggcaccatgg aatctgagag   1680
tgccgacatt ctgacgggag aaatggcgtc gactcagaag tcgctatcac caagcactgt   1740
acagagtgca gactctggat tctcagggac acttggactg ggtttatttt tctatgcaga   1800
```

<210> SEQ ID NO 16
<211> LENGTH: 1800
<212> TYPE: DNA
<213> ORGANISM: Artificial Sequence
<220> FEATURE:
<223> OTHER INFORMATION: Bos taurus interleukin 10 receptor, beta
      (IL10R_)
<220> FEATURE:
<221> NAME/KEY: misc_feature
<222> LOCATION: (1042)..(1042)
<223> OTHER INFORMATION: n is a, c, g, or t

<400> SEQUENCE: 16

```
ctcccccgct tgagcgccct cctgggtccc ggcgcgacta tggcgcgcag cctcctgagc     60
tggctgggcg gctgcctcct gatgtcagca ttaggaatgg ttccacctcc tgaaaatgtc    120
agaatgaatt cagttaattt caagaatatt ctacgatggg agtcacctgc ttttcccaag    180
gggaatctga cgttcacagc tcagtaccaa agttacagga aattccaaga tacatgcacg    240
agtattttgt tgacggaatg cgatttctca agtctttcca agtatggtga ccacaccttg    300
agagtcaggg ctgaatttgc tgatgagagt tcagagtgga taaacatcac cttctgtcct    360
```

```
gtggatgaca ccactatcgg acctcccaga atgcaagtag aagcacttgc taattcttta      420
catgtgcgtt tctttgcccc aagaatcgag aatgaacctg aaccgtggac catgaggaac      480
atttataact catggactta ccatgtgcga tattggaaaa atggctctga tgaaaagttt      540
tcaatttctg gtcagtatga cttcgagttc ctccgaaatc ttgagtcaca gacaacttat      600
tgtgttcgag ttcgagggtt tctttctgat cggaacaaag ctggagaatg gagtgagcct      660
gtctgcgagc aaacaaccat tgacgaaacc accccgtcct ggatggtggc cagcgtcctg      720
gcagcctccg tgtgcgccgc tctcctgcta ctgctcggct gcttcttcct gctgcggtgt      780
gtttacagga aggcaaggca cgccttcccc ccgaggaatt ctcttccgca gcacctgaaa      840
gagtttatga gccaccctca tcacagcact cttctcttat tctccttccc actgtctgat      900
gagaatgaag tctttgacaa actgagcgtc atcacagaag tgtctgaaag ctgcaagctg      960
aaccctgggg ccggctgcgg tctcacgacc tgacgtgggc aggggtcctt ccagctgatg     1020
tccaaggagg gagcacactc anccgggcgc agtgacccc tccttgtcct gtctcccccc      1080
aagggcagtc agagcagcca gccagggcgg gccgagaccg cctgagtaaa ccccagatgg     1140
agagctcacg cagacgccgg ggcagcgtcc acactgccaa ggagctggac tccaaatgct     1200
cgtgtggcaa aaccttggga acttgccact ttttagaggc cttaatgatt tgaaaaaaaa     1260
gttggccact gtgatttccc tgatggtcca tcccagtggt taaaagactc catgcttcca     1320 atgcagggg cacaggttcc atccttggtt gaaaaactaa gatcccacat atcacatgat      1380
gtggccaaaa aaaaaaaaa caaaggttga ggttggccac cagagatatg attctcaggt     1440
atgattctcc tgtgtattca ctaatataaa aaggctttag ggaattcccc agcaggtcca     1500
gtggttagga ctccatgctt tcacagccga gggccgaggt tcagtccctg gtcacggaac     1560
tcagacctca caagccatgt ggcaaaaaaa caaaccacc aaaaaaaaaa gttttaaatg      1620
gttagaaaca aaaatatata aaatgaggaa gaaagaccaa ggcaccatgg aatctgagag     1680
tgccgacatt ctgacgggag aaatggcgtc gactcagaag tcgctatcac caagcactgt     1740
acagagtgca gactctggat ctcagggac acttggactg ggtttatttt tctatgcaga      1800
```

<210> SEQ ID NO 17
<211> LENGTH: 1475
<212> TYPE: DNA
<213> ORGANISM: Artificial Sequence
<220> FEATURE:
<223> OTHER INFORMATION: Bos taurus transforming growth factor, beta 1
      (TGFB1)

<400> SEQUENCE: 17

```
ggacgagcca tcaggaaccg caaacccgac tcccgcgaag acttgacccc agatttcgga       60 cgcacccct tgcacggccc cccaactccc cagcctctct cctgagcccc cgcgcatccg       120
aggacccttc tccgggatcc gggatctctc tcagacttgc ctcagctttc ctattcaaga      180
tcacccatct ctagtaccag agctcaccca tctcggtttt ttttccgtgg ataccgaga       240 acccacccat cagagcctcc cctccagctc tgctccgttc tccctgaagg cctcaactct      300
ccccgcaaac agaccctcct accttttcct cgggagaccc ccaccaccc cagcccctgt      360 aggggcgggg cctccctctt cccaccccag cccagctcgc gctctcggct gtgccggggg     420
gcgccgcctc cccatgccg ccctcggggc tgcggctgct gccgctgctg ctgccgctgc      480
tgtggctgct aatgctgacg cctggccggc cggtcgcacg gctgtccacc tgcaagacca     540
tcgacatgga gctggtgaag cggaatgccg aaacggagga gccagaggcg gactactacg     600
```

```
ccaaggaggt cacccgcgtg ctaatggtgg aatacggcaa caaaatctat gacaaaatga      660
agtctagctc gcacagcata tatatgttct caacacgtc tgagctccgg aagcggtgc       720 ccgaacctgt gttgctctct cgggcagagc tgcgcctgct gaggctcaag ttaaaagtgg      780
agcagcacgt ggagctgtac cagaaatata gcaacaattc ctggcgctac ctcagcaacc      840
ggctgctcgc ccccagcgac tcaccggagt ggctgtcctt tgacgtcact ggagttgtgc      900
ggcagtggct gacccgcaga gaggaaatag agggctttcg cctcagtgcc cactgttcct      960
gtgacagtaa agataacacg cttcaagtgg acattaacgg gttcagttcc ggccgccggg     1020
gtgacctcgc caccattcac ggcatgaacc ggcccttcct gctcctcatg ccacccctc      1080 tggagagggc ccagcacctg cacagctccc gccaccgccg agccctggac caaactact      1140 gcttcagctc cacagaaaag aactgctgtg ttcgtcagct ctacattgac ttccggaagg     1200
acctgggctg gaagtggatt catgaaccca aggggtacca cgccaatttc tgcctggggc     1260
cctgccctta catctggagc ctggatacac agtacagcaa ggtcctggcc ctgtacaacc     1320
agcacaaccc gggcgcttcg gcggcgccgt gctgcgtgcc tcaggcgctg agcccctgc      1380 ccatcgtgta ctacgtgggc cgcaagccca atgtggagca gttgtccaac atgatcgtgc     1440
gctcctgcaa gtgcagctga ggccccgtcc caccc                                1475

<210> SEQ ID NO 18
<211> LENGTH: 2276
<212> TYPE: DNA
<213> ORGANISM: Artificial Sequence
<220> FEATURE:
<223> OTHER INFORMATION: Bos taurus solute carrier family
      11(proton-coupled divalent metal ion transporters), member 1
      (SLC11A1)- NRAMP1

<400> SEQUENCE: 18
gcttgccatg cccgtgaggg gctgccccggc acgccagcca ctcgcacaga gagtgcccga      60
gcctgcggtc ctcatgtcag gtgacacggg ccccccaaag cagggaggga ccagatatgg     120
ctccatctcc agcccaccca gtccagagcc acagcaagca cctccggag ggacctacct      180 aagtgagaag atccccattc cggatacaga atcgggtaca ttcagcctga ggaagctgtg     240
ggccttcacg gggcctggat tcctcatgag catcgcattc ctggacccag gaaacattga     300
gtcggatctt caggctgggg ctgtggctgg attcaaactg ctctgggtgc tgctgtgggc     360
cacagtgttg ggcttgcttt gccagcgact ggctgcccgg ctgggcgtgg tgacaggcaa     420
ggacttgggc gaggtctgcc atctctacta ccctaaggtg ccccgcattc tcctctggct     480
gaccatcgag ctagccatcg tgggctcaga catgcaggaa gtcattggca cagctattgc     540
attcagtctg ctctccgccg gacgaatccc actctgggt ggtgtcctca tcaccgtcgt     600
ggacactttc ttcttcctct tcctcgataa ctacgggttg cggaagctgg aagccttttt     660
tggatttctt attaccataa tggccttgac cttcggctat gagtacgtgg tggctcagcc     720
tgttcaggga gcattgcttc agggcctgtt cctgccctcg tgcccaggct gtggccagcc     780
cgagctgctg caagccgtgg gcatcattgg cgccatcatc atgccccaca acatctacct     840
gcattcctcc ctggtcaagt ctcgagaggt agaccggtcc cggcgggcgg acatccgaga     900
ggccaacatg tacttcctga ttgaagccac catcgccctg tctgtctcct tcctcatcaa     960
cctgtttgtc atggctgtct ttgggcaagc cttctacaag caaaccaacc aggctgcgtt    1020
caacatctgt gccgacagca gcctccacga ctacgcgccg atctttccca ggaacaacct    1080
```

```
gaccgtggca gtggacattt accaaggagg cgtgatcctg ggctgcctct tggtcctcc    1140 agccctgtac atctgggccg tgggtctcct ggctgctggg cagagctcca ccatgaccgg    1200
cacctacgcg ggacagtttg tgatggaggg cttcctgaag ctgcggtggt cacgcttcgc    1260
ccgagtcctg ctcactcgct cctgcgccat cctgcccact gtgctcctgg ctgtcttcag    1320
ggacttgcgg gacctgtcag gcctcaacga cctgctcaat gtgctgcaga gcctgctgct    1380
tcccttcgct gtgctgccca tcctcacctt caccagcatg cccgccctga tgcaggagtt    1440
tgccaatggc ctggtgagca agttatcac ttcctccatc atggtgctgg tctgcgccgt     1500
caacctttac ttcgtgatca gctacttgcc cagcctcccc caccctgcct acttcagcct    1560
tgtagcactg ctggccgcag cctacctggg cctcaccact tacctggtct ggacctgtct    1620
catcacccag ggagccactc ttctggccca cagttcccac caacgcttcc tgtatgggct    1680
tcctgaagag gatcaggaga aggggaggac ctcgggatga gctcccacca gggcctggcc    1740
acgggtggaa tgagtgggca cagtggcctg tcagacaagg gtgtgtgtgt gtgtgtgtgt    1800
gtgtatgtgt gtgaaggcag caagacagac agggagttct ggaagctggc caacgtgagt    1860
tccagaggga cctgtgtgtg tgtgacacac tggcctgcca gacaagggtg tgtgtgtgtg    1920
tgtgtgtgtg tgtgcatgca cagcaagacg gagagggagt tctggaaggc agccaacgtg    1980
agttccatag ggacctgcta tttcctagct cagatctcag tgttcttgac tataaaatgg    2040
ggacacctac cttggagtgg ttgtaaataa gacacttgaa cgcagagcct agcacttcag    2100
atttaaaaac aaaagaatca taattccaaa agttactgag cactatcaca ggagtgacct    2160
gacagaccca cccagtctag ggtgggaccc aggctccaaa ctgatttaaa ataagagtct    2220
gaaaatgcta ataaatgct gttgtgctta gtccccgaat ccatatgact agtaga         2276
```

<210> SEQ ID NO 19
<211> LENGTH: 2276
<212> TYPE: DNA
<213> ORGANISM: Artificial Sequence
<220> FEATURE:
<223> OTHER INFORMATION: Bos taurus solute carrier family
      11(proton-coupled divalent metal ion transporters), member 1
      (SLC11A1)- NRAMP1

<400> SEQUENCE: 19

```
gcttgccatg cccgtgaggg gctgcccggc acgccagcca ctcgcacaga gagtgcccga     60
gcctgcggtc tcatgtcag gtgacacggg cccccaaag cagggaggga ccagatatgg      120
ctccatctcc agcccaccca gtccagagcc acagcaagca cctccggag ggacctacct     180 aagtgagaag atccccattc cggatacaga atcgggtaca ttcagcctga ggaagctgtg    240
ggccttcacg gggcctggat tcctcatgag catcgcattc ctggacccag aaacattga    300 gtcggatctt caggctgggg ctgtggctgg attcaaactg ctctgggtgc tgctgtgggc    360
cacagtgttg ggcttgcttt gccagcgact ggctgcccgg ctgggcgtgg tgacaggcaa    420
ggacttgggc gaggtctgcc atctctacta ccctaaggtg ccccgcattc tcctctggct    480
gaccatcgag ctagccatcg tgggctcaga catgcaggaa gtcattggca cagctattgc    540
attcagtctg ctctccgccg gacgaatccc actctggggt ggtgtcctca tcaccgtcgt    600
ggacactttc ttcttcctct cctcgataa ctacggggttg cggaagctgg aagccttttt    660
tggattcctt attaccataa tggccttgac cttcggctat gagtacgtgg tggctcagcc    720
tgctcaggga gcattgcttc agggcctgtt cctgccctcg tgcccaggct gtggccagcc    780
cgagctgctg caagccgtgg gcatcattgg cgccatcatc atgccccaca acatctacct    840
```

```
gcattcctcc ctggtcaagt ctcgagaggt agaccggtcc cggcgggcgg acatccgaga    900
ggccaacatg tacttcctga ttgaagccac catcgccctg tctgtctcct tcctcatcaa    960
cctgtttgtc atggctgtct ttgggcaagc cttctacaag caaaccaacc aggctgcgtt   1020
caacatctgt gccgacagca gcctccacga ctacgcgccg atctttccca ggaacaacct   1080
gaccgtggca gtggacattt accaaggagg cgtgatcctg ggctgcctct ttggtcctgc   1140
agccctgtac atctgggccg tgggtctcct ggctgctggg cagagctcca ccatgaccgg   1200
cacctacgcg ggacagtttg tgatggaggg cttcctgaag ctgcggtggt cacgcttcgc   1260
ccgagtcctg ctcactcgct cctgcgccat cctgcccact gtgctcctgg ctgtcttcag   1320
ggacttgcgg gacctgtcag gcctcaacga cctgctcaat gtgctgcaga gcctgctgct   1380
tcccttcgct gtgctgccca tcctcacctt caccagcatg cccgccctga tgcaggagtt   1440
tgccaatggc ctggtgagca agttatcac ttcctccatc atggtgctgg tctgcgccgt   1500
caacctttac ttcgtgatca gctacttgcc cagcctcccc cacccctgcct acttcagcct   1560 tgtagcactg ctggccgcag cctacctggg cctcaccact tacctggtct ggacctgtct   1620
catcacccag ggagccactc ttctggccca cagttcccac caacgcttcc tgtatgggct   1680
tcctgaagag gatcaggaga aggggaggac ctcgggatga gctcccacca gggcctggcc   1740
acgggtggaa tgagtgggca cagtggcctg tcagacaagg gtgtgtgtgt gtgtgtgtgt   1800
gtgtatgtgt gtgaaggcag caagacagac agggagttct ggaagctggc aacgtgagt    1860 tccagaggga cctgtgtgtg tgtgacacac tggcctgcca gacaagggtg tgtgtgtgtg   1920
tgtgtgtgtg tgtgcatgca cagcaagacg gagagggagt tctggaaggc agccaacgtg   1980
agttccatag ggacctgcta tttcctagct cagatctcag tgttcttgac tataaaatgg   2040
ggacacctac cttggagtgg ttgtaaataa gacacttgaa cgcagagcct agcacttcag   2100
atttaaaaac aaaagaatca taattccaaa agttactgag cactatcaca ggagtgacct   2160
gacagaccca cccagtctag ggtgggaccc aggctccaaa ctgatttaaa ataagagtct   2220
gaaaatgcta aataaatgct gttgtgctta gtccccgaat ccatatgact agtaga        2276
```

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
agccagcagc tctcaaagtc                                                  20

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gtgttcagtg tggtcctgga t                                                21

<210> SEQ ID NO 22
<211> LENGTH: 22
<212> TYPE: DNA
<213> ORGANISM: Artificial Sequence
<220> FEATURE:

<223> OTHER INFORMATION: primer

<400> SEQUENCE: 22
ggtaaagcag tcctgaatcc aa                                              22

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
tccttcatgg gccctattt                                                  19

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tcgtgtttat tgctctggtt gt                                              22

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
cctgcttcct tccctcct                                                   18

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
gggttcctgc tggtgactc                                                  19

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
gccaatgcca ctgtcctc                                                   18

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
gggttcctgc tggtgactc                                                  19

```
<210> SEQ ID NO 29
<211> LENGTH: 18
<212> TYPE: DNA
<213> ORGANISM: Artificial Sequence
<220> FEATURE:
<223> OTHER INFORMATION: primer

<400> SEQUENCE: 29
gccaatgcca ctgtcctc                                                 18

<210> SEQ ID NO 30
<211> LENGTH: 19
<212> TYPE: DNA
<213> ORGANISM: Artificial Sequence
<220> FEATURE:
<223> OTHER INFORMATION: primer

<400> SEQUENCE: 30
agtgcagaca gcgggatct                                                19

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ttcttcaggg gtctgcaaag                                               20

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
agtgcagaca gcgggatct                                                19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
ttcttcaggg gtctgcaaag                                               20

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
agtgcagaca gcgggatct                                                19

<210> SEQ ID NO 35
<211> LENGTH: 20
<212> TYPE: DNA
<213> ORGANISM: Artificial Sequence
<220> FEATURE:
<223> OTHER INFORMATION: primer
```

<400> SEQUENCE: 35
ttcttcaggg gtctgcaaag					20

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
gggaattcag ggaataaagc a					21

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ctgtttgggg aatgcagatt					20

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
gggaattcag ggaataaagc a					21

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ctgtttgggg aatgcagatt					20

<210> SEQ ID NO 40
<211> LENGTH: 19
<212> TYPE: DNA
<213> ORGANISM: Artificial Sequence
<220> FEATURE:
<223> OTHER INFORMATION: primer

<400> SEQUENCE: 40
cccttgccaa acactgaca					19

<210> SEQ ID NO 41
<211> LENGTH: 18
<212> TYPE: DNA
<213> ORGANISM: Artificial Sequence
<220> FEATURE:
<223> OTHER INFORMATION: primer

<400> SEQUENCE: 41
cctagcccag gccactt					18

<210> SEQ ID NO 42
<211> LENGTH: 20

```
<212> TYPE: DNA
<213> ORGANISM: Artificial Sequence
<220> FEATURE:
<223> OTHER INFORMATION: primer

<400> SEQUENCE: 42
tcctctggag aagggaaagg                                               20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
attcagaggc aggagtcgag                                               20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
acatgtgttg gccaagtgaa                                               20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
acatccgagt cctgagtggt                                               20
```

SINGLE NUCLEOTIDE POLYMORPHISMS (SNPS) IN GENES ASSOCIATED WITH INFLAMMATORY DISEASES

RELATED APPLICATIONS

This application is a division of U.S. application Ser. No. 12/854,408 filed Aug. 11, 2010, which claims the benefit under 35 USC §119(e) of U.S. provisional application Ser. No. 61/232,965 filed Aug. 11, 2009. All of the prior applications are incorporated herein in their entirety.

INCORPORATION OF SEQUENCE LISTING

A computer readable form of the Sequence Listing "6580-P35240US02 SequenceListing.txt" (86,920 bytes), submitted via EFS-WEB and created on Mar. 18, 2013, is hereby incorporated by reference.

FIELD OF THE DISCLOSURE

The present disclosure relates to the identification of single nucleotide polymorphisms (SNPs) in genes associated with inflammatory diseases, compositions, and methods for screening for, detecting, diagnosing or identifying susceptibility to or detecting a risk of developing inflammatory diseases.

BACKGROUND OF THE DISCLOSURE

Two prominent infectious inflammatory diseases occurring in bovines, and prevalent in dairy cattle, are mastitis and Johne's disease.

It is generally known that bovine mastitis is an inflammatory disease of the mammary gland most often caused by infection with contagious and/or environmental pathogenic bacteria such as *Escherichia coli, Staphylococcus aureus, Streptococcus agalactiae* and *Streptococcus dysgalactiae*. Generally, mastitis is manifested as a clinical as well as subclinical disease, and in cases of chronic infection, animals may remain asymptomatic throughout their entire life and potentially infect others within the herd (Oviedo-Boyso et al. 2007).

Not only is mastitis the most prevalent disease affecting dairy cattle, it is also the most costly for the dairy industry, with economic losses attributed to decreased milk production and quality, increased labor due to treatment and herd management strategies, and premature culling of highly susceptible animals (Halasa et al. 2007). In the United Kingdom alone, mastitis is estimated to cost up to 287 euros per cow per year, and approximately 9 million euros to the dairy industry as a whole (Hillerton et al. 1992; Kossaibati and Esslemont 1997).

It is known that the etiology of mastitis is complex, involving many causal strains of bacteria, as well as a wide variety of host factors that contribute to disease susceptibility. These factors include parity, stage of lactation, nutritional state, and host genetics (Oviedo-Boyso et al. 2007; Pyorala 2002). Given the complexity of this disease's etiology, and even though multiple management strategies have been adopted to control its rate of incidence, there is currently no effective means to screen for, identify and eventually eradicate mastitis from the dairy industry.

As mentioned above, another inflammatory disease occurring prominently in ruminants is Johne's disease, a chronic inflammatory bowel disease caused by an infection with *Mycobacterium avium paratuberculosis* (MAP). Incidentally, Johne's disease parallels Crohn's disease in humans in many respects. Since MAP is a slow-growing intracellular pathogen, infected cattle typically remain asymptomatic for 2 to 10 years making it difficult to control Johne's disease in dairy herds (McKenna et al., 2006). During this asymptomatic period, the pathogen can be horizontally transmitted to other herd members via contaminated feces, and vertically transmitted to calves via contaminated milk and colostrum (McKenna et al., 2006).

The presence of MAP in milk also poses a zoonotic risk to humans (Waddell et al. 2008). This may be particularly relevant for individuals that are genetically predisposed to inflammatory bowel disease (IBD), since MAP has been implicated as one of several potential pathogens associated with Crohn's disease (Glasser et al., 2008). A meta-analysis of studies examining the presence of MAP in patients with Crohn's disease or ulcerative colitis for example, showed that there was a greater likelihood of detecting MAP in diseased versus healthy individuals (Feller et al., 2007). Additionally, clinical studies have also shown that anti-mycobacterial treatment of some patients with Crohn's disease can lead to pathological remission (Chamberlin et al., 2007).

Variability in the susceptibility of cattle to MAP infection is evident. In a typical commercial dairy herd where there is a consistent prevalence of MAP infection for example, it is common to find animals that remain healthy, even after several years of exposure. Additionally, there is evidence that susceptibility to MAP infection, and the development of clinical symptoms associated with Johne's disease is inherited; heritability estimates in dairy cattle have been estimated to range from 0.010 to 0.183, depending on the criteria used to diagnose MAP infection or Johne's disease (Koetz et al., 2000; Gonda et al., 2006; Mortensen et al., 2004).

SUMMARY OF THE DISCLOSURE

The present disclosure addresses the need to limit the incidence of inflammatory diseases such as bovine mastitis and Johne's disease, which would be useful for the dairy cattle industry potentially improving the overall health of herds. Accordingly, there is a need in the art for the identification of genes involved in inflammatory diseases, and particularly the identification of single nucleotide polymorphisms (SNPs) in these genes for use in screening for, diagnosing, identifying susceptibility to or detecting a risk of developing mastitis and/or *Mycobacterium avium paratuberculosis* (MAP) infection and Johne's disease. Furthermore, there is a need for selection of sires and dams with enhanced genetic resistance to mastitis and Johne's disease in cattle breeding in order to improve the overall health of cattle, and to reduce the risk of human exposure to mastitis and/or Johne's disease.

The present disclosure discloses the identification of single nucleotide polymorphisms (SNPs) in genes associated with inflammatory diseases and uses thereof. In one embodiment, the inflammatory disease is mastitis. In another embodiment, the inflammatory disease is Johne's disease. In a further embodiment, the gene associated with inflammatory disease is a gene encoding an anti-inflammatory cytokine and/or a receptor thereof, a growth factor and/or receptor thereof and/or an anti-bacterial promoting protein.

The SNPs identified by the inventors in genes associated with inflammatory disease are described in Tables 1 and 5, and include: (a) IL-10 969T>C(NCBI dbSNP ssID: ss104807640, Build 130; SEQ ID NO: 7); (b) IL-10 1220A>C(NCBI dbSNP ssID: ss104807641, Build 130; SEQ ID NO: 8); (c) IL-10Rα 1047C>A (NCBI dbSNP ssID: ss104807642, Build 130; SEQ ID NO: 9); (d) IL-10Rα

1398G>A (NCBI dbSNP ssID: ss104807643, Build 130; SEQ ID NO: 10); (e) IL-10Rα 1512C>T (NCBI dbSNP ssID: ss104807644, Build 130; SEQ ID NO: 11); (f) IL-10Rα 1599C>T (NCBI dbSNP ssID: ss104807645, Build 130; SEQ ID NO: 12); (g) IL-10Rα 1683T>C(NCBI dbSNP ssID: ss104807646, Build 130; SEQ ID NO: 13); (h) IL-10Rα 1716A>G (NCBI dbSNP ssID: ss104807647, Build 130; SEQ ID NO: 14); (i) IL-10Rβ 542C>T (NCBI dbSNP ssID: ss104807648, Build 130; SEQ ID NO: 15); (j) IL-10Rβ 608A>G (NCBI dbSNP ssID: ss104807649, Build 130; SEQ ID NO: 16); (k) TGF-βI 701C>T (NCBI dbSNP ssID: ss104807650, Build 130; SEQ ID NO: 17); (l) NRAMP1 723C>T (NCBI dbSNP ssID: ss104807654, Build 130; SEQ ID NO: 18); and (m) NRAMP1 1139C>G, NCBI dbSNP ssID: ss104807655, Build 130; SEQ ID NO: 19). Accordingly, one embodiment of the present disclosure is an isolated nucleic acid molecule comprising one of the SNPs in SEQ ID NOS: 7-19. The present inventors have also identified SNP haplotypes in various SNPs identified in the IL-10Rα gene.

The present inventors have determined the association of the identified SNPs and/or SNP haplotypes in genes related to inflammatory diseases in bovines, including for example, in mastitis and Johne's disease.

Accordingly, another aspect of the present disclosure provides a method of screening for, diagnosing, identifying susceptibility to or detecting a risk of developing an inflammatory disease comprising detecting the presence or absence of at least one SNP identified in a gene associated with inflammatory disease in a subject, wherein the presence of the at least one SNP is indicative of an increased risk of inflammatory disease in the subject, and the absence of the at least one SNP is indicative of a decreased risk of inflammatory disease in the subject. In one embodiment, the inflammatory disease is mastitis. In another embodiment, the inflammatory disease is Johne's disease. In one embodiment, the at least one of the SNPs associated with inflammatory disease includes SNPs associated with mastitis and/or SNPs associated with MAP infection.

In another embodiment, the method of screening for, diagnosing, identifying susceptibility to or detecting a risk of developing an inflammatory disease comprising detecting the presence or absence of at least one SNP identified in a gene associated with inflammatory disease in a subject, further comprises selecting a subject for a breeding program comprising, based on the presence or absence of the SNP associated with an inflammatory disease, such as mastitis and/or Johne's disease.

Another aspect of the present disclosure provides a method of treating inflammatory disease in a subject including (a) detecting the presence or absence of at least one of the SNPs associated with inflammatory disease; and (b) administering to the subject, if at least one of the SNPs associated with inflammatory disease is present, an effective amount of an agent that treats inflammatory disease. In one embodiment, the inflammatory disease is mastitis. In another embodiment, the inflammatory disease is Johne's disease.

The present disclosure also provides compositions including nucleic acid probes that may be used to detect the presence or absence of at least one of the SNPs associated with inflammatory disease. The present disclosure also provides nucleotide sequences comprising forward and reverse primers that amplify SNPs identified in genes associated with inflammatory disease.

The present disclosure also includes kits containing the nucleic acid probes or primers described herein and instructions for use.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION OF THE DISCLOSURE

I. Single Nucleotide Polymorphisms

The present inventors have investigated genes involved in inflammatory diseases, such as mastitis and Johne's disease (caused by an infection with *Mycobacterium avium paratuberculosis*), in order to identify single nucleotide polymorphisms (SNPs) in genes associated with inflammatory diseases. In particular, the present inventors investigated and selected six genes, including genes encoding anti-inflammatory cytokines and receptors thereof, growth factors and receptors thereof and an anti-bacterial promoting protein for identification of SNPs, namely, IL-10 [interleukin 10; NCBI-GeneID: 281246; SEQ ID NO: 1], IL-10Rα [interleukin 10 receptor subunit alpha; NCBI-GeneID: 513478; SEQ ID NO: 2]; IL-10Rβ [interleukin 10 receptor subunit beta; NCBI-GeneID: 767864; SEQ ID NO: 3], TGF-βI [transforming growth factor beta class I; NCBI-GeneID: 282089; SEQ ID NO: 4], TGF-βR type I [transforming growth factor beta type I receptor; NCBI-GeneID: 282382; TGF-βR type II [transforming growth factor beta type II receptor; NCBI-GeneID: 535376; SEQ ID NO: 5]; and NRAMP1 [natural resistance-associated macrophage protein 1; NCBI-GeneID: 282470; SEQ ID NO: 6].

As used herein, the term "SNP" means a single nucleotide polymorphism which is a single nucleotide position in a nucleotide sequence for which two or more alternative alleles are present in a given population.

The term "allele" means any one of a series of two or more different gene sequences that occupy the same position or locus on a chromosome.

The present inventors have identified thirteen SNPs in the IL-10, IL-10Rα, IL-10Rβ, TGF-βI and NRAMP1 genes. In particular, two SNPs were identified in IL-10; six were identified in IL-10Rα; two were identified in IL-10Rβ; one was identified in TGF-β1 and two were identified in NRAMP1 as set out immediately below and in Tables 1 and 5:

(a) the presence of a C nucleotide at position 969 in the 5' region of the IL-10 gene rather than a T nucleotide at position 969 as in SEQ ID NO: 1 (SNP IL-10 969T>C; NCBI dbSNP ssID: ss104807640, Build 130; SEQ ID NO: 7);

(b) the presence of a C nucleotide at position 1220 in the 5' region of the IL-10 gene rather than an A nucleotide at position 1220 as in SEQ ID NO: 1 (SNP IL-10 1220A>C; NCBI dbSNP ssID: ss104807641, Build 130; SEQ ID NO:8);

(c) the presence of an A nucleotide at position 1047 in the coding region of the IL-10Rα gene rather than a C nucleotide at position 1047 as in SEQ ID NO: 2 (SNP IL-10Rα 1047C>A; NCBI dbSNP ssID: ss104807642, Build 130; SEQ ID NO: 9);

(d) the presence of an A nucleotide at position 1398 in the coding region of the IL-10Rα gene rather than a G nucleotide at position 1398 as in SEQ ID NO: 2 (SNP IL-10Rα 1398G>A; NCBI dbSNP ssID: ss104807643, Build 130; SEQ ID NO: 10);

(e) the presence of a T nucleotide at position 1512 in the coding region of the IL-10Rα gene rather than a C nucleotide at position 1512 as in SEQ ID NO: 2 (SNP IL-10Rα 1512C>T; NCBI dbSNP ssID: ss104807644, Build 130; SEQ ID NO: 11);

(f) the presence of a T nucleotide at position 1599 in the coding region of the IL-10Rα gene rather than a C nucleotide at position 1599 as in SEQ ID NO: 2 (SNP IL-10Rα 1599C>T; NCBI dbSNP ssID: ss104807645, Build 130; SEQ ID NO: 12);

(g) the presence of a C nucleotide at position 1683 in the coding region of the IL-10Rα gene rather than a T nucleotide at position 1683 as in SEQ ID NO: 2 (SNP IL-10Rα 1683T>C; NCBI dbSNP ssID: ss104807646, Build 130; SEQ ID NO: 13);

(h) the presence of a G nucleotide at position 1716 in the coding region of the IL-10Rα gene rather than an A nucleotide at position 1716 as in SEQ ID NO: 2 (SNP IL-10Rα 1716A>G, NCBI dbSNP ssID: ss104807647, Build 130; SEQ ID NO: 14);

(i) the presence of a T nucleotide at position 542 in the coding region of the IL-10Rβ gene rather than a C nucleotide at position 542 as in SEQ ID NO: 3 (SNP IL-10Rβ 542C>T, NCBI dbSNP ssID: ss104807648, Build 130; SEQ ID NO: 15);

(j) the presence of a G nucleotide at position 608 in the coding region of the IL-10Rβ gene rather than an A nucleotide at position 608 as in SEQ ID NO: 3 (SNP IL-10Rβ 608A>G, NCBI dbSNP ssID: ss104807649, Build 130; SEQ ID NO: 16);

(k) the presence of a T nucleotide at position 701 in the coding region of the TGF-β1 gene rather than a C nucleotide at position 701 as in SEQ ID NO: 4 (SNP TGF-β1 701C>T, NCBI dbSNP ssID: ss104807650, Build 130; SEQ ID NO: 17);

(l) the presence of a T nucleotide at position 723 in the coding region of the NRAMP1 gene rather than a C nucleotide at position 723 as in SEQ ID NO: 6 (SNP NRAMP1 723C>T, NCBI dbSNP ssID: ss104807654, Build 130; SEQ ID NO: 18); and (m) the presence of a G nucleotide at position 1139 in the coding region of the NRAMP1 gene rather than a C nucleotide at position 1139 as in SEQ ID NO: 6 (SNP NRAMP1 1139C>G, NCBI dbSNP ssID: ss104807655, Build 130; SEQ ID NO: 19), which are associated with inflammatory diseases including mastitis and/or Johne's disease (caused by *Mycobacterium avium paratuberculosis* (MAP) infection). The present inventors found that the SNPs identified in SEQ ID NOS: 10, 11, 13 and 14 (namely, SNP IL-10Rα 1398G>A, SNP IL-10Rα 1512C>T, SNP IL-10Rα 1683T>C, and SNP IL-10Rα 1716A>G, respectively) are completely linked. The present inventors also determined that the SNPs identified in SEQ ID NOS: 9, 10 and 12 (namely, SNP IL-10Rα 1047C>A, SNP IL-10Rα 1398G>A; and SNP IL-10Rα 1599C>T, respectively) are in linkage disequilibrium.

Other variants of the above-noted genes are contemplated by the present disclosure. Accordingly, in one embodiment, the nucleotides at positions 969 and 1220 in the IL-10 gene (SEQ ID NO: 1) may have nucleotides that differ from the SNPs identified in SEQ ID NOS: 7-8 and the wild-type sequence in SEQ ID NO: 1. In another embodiment, the nucleotides at positions 1047, 1398, 1512, 1599, 1683, and 1716 in IL-10Rα gene (SEQ ID NO: 2) may have nucleotides that differs from the SNPs identified in SEQ ID NOS: 9-14 and the wild-type sequence in SEQ ID NO: 2. In another embodiment, the nucleotides at positions 542 and 608 in the IL-10Rβ gene (SEQ ID NO: 3) may have nucleotides that differ from the SNPs identified in SEQ ID NOS: 15-16 and the wild-type sequence in SEQ ID NO: 3. In another embodiment, the nucleotide at position 701 in the TGF-β1 gene (SEQ ID NO' 4) may differ from the SNP identified in SEQ ID NO: 17 and the wild-type sequence in SEQ ID NO: 4. In a further embodiment, the nucleotides at positions 723 and 1139 of the NRAMP1 gene (SEQ ID NO: 6) may differ from the SNPs identified in SEQ ID NOS: 18-19 and the wild-type sequence in SEQ ID NO: 6.

Another embodiment of the present disclosure includes an isolated nucleic acid molecule comprising one of the SNPs identified in SEQ ID NOS: 7-19. In another embodiment, the isolated nucleic acid molecule comprises one of the SNPs identified in SEQ ID NOS: 10, 11, 13 and 14. In a further embodiment, the isolated nucleic acid molecule comprises one of the SNPs identified in SEQ ID NOS: 9, 10 and 12. In another embodiment, the isolated nucleic acid molecule comprises the SNP identified in SEQ ID NO: 12.

The term "isolated nucleic acid molecule" refers to a nucleic acid substantially free of cellular material or culture medium, for example, when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

A. Haplotypes in Mastitis

Referring to Table 4, the present inventors identified and determined that various haplotypes, namely, AAT, AGT and CAT, in three of the SNPs in the IL-10Rα gene, namely, SNP IL-10Rα 1047C>A; SNP IL-10Rα 1398G>A; and SNP IL-10Rα 1599C>T showed different effects on mastitis as compared to the most frequent haplotype, AGC. In particular, the AAT haplotype in three of the SNPs in the IL-10Rα gene, namely, SNP IL-10Rα 1047C>A; SNP IL-10Rα 1398G>A; and SNP IL-10Rα 1599C>T ("AAT SNP haplotype") showed a significant effect as compared to the most frequent haplotype, AGC ("AGC SNP haplotype"). In addition, the present inventors found that SNP IL-10Rα 1398G>A is completely linked to at least three SNPs, namely, SNP IL-10Rα 1512C>T; SNP IL-10Rα 1683T>C; and SNP IL-10Rα 1716A>G. Therefore, the various haplotypes identified by the inventors, namely, AAT, AGT and CAT, also comprise these at least three SNPs.

Accordingly, in one embodiment the AGC SNP haplotype of the IL-10Rα gene associated with mastitis comprises: (a) the presence of an A nucleotide at position 1047 in the coding region of the IL-10Rα gene rather than a C nucleotide at position 1047 as in SEQ ID NO: 2; (b) the presence of G nucleotide at position 1398 as in SEQ ID NO: 2; and (c) the presence of a C nucleotide at position 1599 as in SEQ ID NO: 2.

In another embodiment, the AAT SNP haplotype of the IL-10Rα gene associated with mastitis comprises: (a) the presence of an A nucleotide at position 1047 in the coding region of the IL-10Rα gene rather than a C nucleotide at position 1047 as in SEQ ID NO: 2; (b) the presence of an A nucleotide at position 1398 in the coding region of the IL-10Rα gene rather than a G nucleotide at position 1398 as in SEQ ID NO: 2; and (c) the presence of a T nucleotide at position 1599 in the coding region of the IL-10Rα gene rather than a C nucleotide at position 1599 as in SEQ ID NO: 2.

B. Haplotypes in MAP Infection

Referring to Table 7, the present inventors also identified and determined that various haplotypes, namely, AAT, CAC and AAC, in three of the SNPs in the IL-10Rα gene, namely, SNP IL-10Rα 1047C>A; SNP IL-10Rα 1398G>A; and SNP IL-10Rα 1599C>T showed different effects on MAP infection as compared to the most frequent haplotype in the positive cohort, AGC. In particular, the AAT haplotype in three of the SNPs in the IL-10Rα gene, namely, SNP IL-10Rα 1047C>A; SNP IL-10Rα 1398G>A; and SNP IL-10Rα 1599C>T ("AAT SNP haplotype") showed a significant effect in the negative cohort as compared to the most frequent haplotype, AGC ("AGC SNP haplotype"). In addition, the inventors found that SNP IL-10Rα 1398G>A is completely linked to at least three SNPs, namely, SNP IL-10Rα 1512C>T; SNP IL-10Rα 1683T>C; and SNP IL-10Rα 1716A>G. Therefore, the various haplotypes identified by the inventors, namely, AAT, CAC and AAC, also comprise these at least three SNPs.

Accordingly, in one embodiment the AGC SNP haplotype of the IL-10Rα gene associated with MAP infection in the positive cohort comprises: (a) the presence of an A nucleotide at position 1047 in the coding region of the IL-10Rα gene rather than a C nucleotide at position 1047 as in SEQ ID NO: 2; (b) the presence of G nucleotide at position 1398 as in SEQ ID NO: 2; and (c) the presence of a C nucleotide at position 1599 as in SEQ ID NO: 2.

In another embodiment, the AAT SNP haplotype of the IL-10Rα gene associated with MAP infection in the negative cohort comprises: (a) the presence of an A nucleotide at position 1047 in the coding region of the IL-10Rα gene rather than a C nucleotide at position 1047 as in SEQ ID NO: 2; (b) the presence of an A nucleotide at position 1398 in the coding region of the IL-10Rα gene rather than a G nucleotide at position 1398 as in SEQ ID NO: 2; and (c) the presence of a T nucleotide at position 1599 in the coding region of the IL-10Rα gene rather than a C nucleotide at position 1599 as in SEQ ID NO: 2.

II. Methods and Uses of the Disclosure

A. Methods and Uses for Genetic Analysis

The present inventors have determined the association of identified individual SNPs and/or SNP haplotypes described herein in genes related to inflammatory diseases in bovines, including for example, mastitis and Johne's disease.

Accordingly, in one embodiment, the present disclosure includes methods and uses of the SNPs identified in SEQ ID NOS: 7-19 in or for genetic analysis. In one embodiment, genetic analysis includes linkage analysis or association analysis. In a further embodiment, association analysis includes analyzing association with inflammatory diseases. In another embodiment, association analysis includes analyzing association with mastitis in cattle. In another embodiment, association analysis includes analyzing association with MAP infection and/or Johne's disease in cattle.

B. Methods and Uses for Inflammatory Diseases

As noted above, the present inventors have determined the association of identified individual SNPs and/or SNP haplotypes described herein in genes related to inflammatory diseases in bovines.

Accordingly, one embodiment of the present disclosure is a method of screening for, diagnosing, identifying susceptibility to or detecting a risk of developing an inflammatory disease comprising detecting the presence or absence of at least one SNP identified in a gene associated with inflammatory disease in a subject, wherein the presence of the at least one SNP is indicative of an increased risk of inflammatory disease in the subject, and the absence of the at least one SNP is indicative of a decreased risk of inflammatory disease in the subject.

In another embodiment, the genes associated with inflammatory disease include genes that encode an anti-inflammatory cytokine, an anti-inflammatory cytokine receptor, a growth factor, a growth factor receptor and/or an anti-bacterial promoting protein. In another embodiment, the anti-inflammatory cytokine is IL-10 (interleukin 10). In another embodiment, the anti-inflammatory cytokine receptor is IL-10Rα (interleukin 10 receptor subunit alpha) and/or IL-10Rβ (interleukin 10 receptor subunit beta β). In another embodiment, the growth factor is TGF-βI (transforming growth factor beta class I). In another embodiment, the growth factor receptor is TGF-βR type I (transforming growth factor beta type I receptor) and/or TGF-βR type II (transforming growth factor beta type II receptor). In a further embodiment, the anti-bacterial promoting protein is NRAMP1 (natural resistance-associated macrophage protein 1).

In another embodiment, at least one SNP identified in a gene associated with inflammatory disease comprises:

(a) the presence of a C nucleotide at position 969 in the 5' region of the IL-10 gene rather than a T nucleotide at position 969 as in SEQ ID NO: 1 (SNP IL-10 969T>C; NCBI dbSNP ssID: ss104807640, Build 130; SEQ ID NO: 7);

(b) the presence of a C nucleotide at position 1220 in the 5' region of the IL-10 gene rather than an A nucleotide at position 1220 as in SEQ ID NO: 1 (SNP IL-10 1220A>C; NCBI dbSNP ssID: ss104807641, Build 130; SEQ ID NO:8);

(c) the presence of an A nucleotide at position 1047 in the coding region of the IL-10Rα gene rather than a C nucleotide at position 1047 as in SEQ ID NO: 2 (SNP IL-10Rα 1047C>A; NCBI dbSNP ssID: ss104807642, Build 130; SEQ ID NO: 9);

(d) the presence of an A nucleotide at position 1398 in the coding region of the IL-10Rα gene rather than a G nucleotide at position 1398 as in SEQ ID NO: 2 (SNP IL-10Rα 1398G>A; NCBI dbSNP ssID: ss104807643, Build 130; SEQ ID NO: 10);

(e) the presence of a T nucleotide at position 1512 in the coding region of the IL-10Rα gene rather than a C nucleotide at position 1512 as in SEQ ID NO: 2 (SNP IL-10Rα 1512C>T; NCBI dbSNP ssID: ss104807644, Build 130; SEQ ID NO: 11);

(f) the presence of a T nucleotide at position 1599 in the coding region of the IL-10Rα gene rather than a C nucleotide at position 1599 as in SEQ ID NO: 2 (SNP IL-10Rα 1599C>T; NCBI dbSNP ssID: ss104807645, Build 130; SEQ ID NO: 12);

(g) the presence of a C nucleotide at position 1683 in the coding region of the IL-10Rα gene rather than a T nucleotide at position 1683 as in SEQ ID NO: 2 (SNP IL-10Rα 1683T>C; NCBI dbSNP ssID: ss104807646, Build 130; SEQ ID NO: 13);

(h) the presence of a G nucleotide at position 1716 in the coding region of the IL-10Rα gene rather than an A nucleotide at position 1716 as in SEQ ID NO: 2 (SNP IL-10Rα 1716A>G, NCBI dbSNP ssID: ss104807647, Build 130; SEQ ID NO: 14);

(i) the presence of a T nucleotide at position 542 in the coding region of the IL-10Rβ gene rather than a C nucleotide at position 542 as in SEQ ID NO: 3 (SNP IL-10Rβ542C>T, NCBI dbSNP ssID: ss104807648, Build 130; SEQ ID NO: 15);

(j) the presence of a G nucleotide at position 608 in the coding region of the IL-10Rβ gene rather than an A nucleotide at position 608 as in SEQ ID NO: 3 (SNP IL-10Rβ608A>G, NCBI dbSNP ssID: ss104807649, Build 130; SEQ ID NO: 16);

(k) the presence of a T nucleotide at position 701 in the coding region of the TGF-βI gene rather than a C nucleotide at position 701 as in SEQ ID NO: 4 (SNP TGF-β1701C>T, NCBI dbSNP ssID: ss104807650, Build 130; SEQ ID NO: 17);

(l) the presence of a T nucleotide at position 723 in the coding region of the NRAMP1 gene rather than a C nucleotide at position 723 as in SEQ ID NO: 6 (SNP NRAMP1 723C>T, NCBI dbSNP ssID: ss104807654, Build 130; SEQ ID NO: 18); and (m) the presence of a G nucleotide at position 1139 in the coding region of the NRAMP1 gene rather than a C nucleotide at position 1139 as in SEQ ID NO: 6 (SNP NRAMP1 1139C>G, NCBI dbSNP ssID: ss104807655, Build 130; SEQ ID NO: 19).

C. Methods of Screening for, Diagnosing, Identifying Susceptibility to or Detecting a Risk of Developing Mastitis, and Selecting for a Breeding Program In one embodiment of the methods and uses for inflammatory disease, the inflammatory disease is mastitis. Accordingly, in another embodiment, the at least one SNP identified in a gene associated with inflammatory disease is a SNP associated with mastitis. In another embodiment, the SNP associated with mastitis comprises one of the SNPs in SEQ ID NOS: 7-17.

The present inventors have associated the identified individual SNPs and/or SNP haplotypes to mastitis. In particular, the present inventors have determined the association of the identified individual SNPs and/or SNP haplotypes to mastitis using estimated breeding values (EBV) for somatic cell scores (SCS) in cattle.

Accordingly, one embodiment of the present disclosure is a method of screening for, diagnosing, identifying susceptibility to or detecting a risk of developing mastitis comprising detecting the presence or absence of at least one of the SNPs associated with mastitis, such as the SNPs described in SEQ ID NOS: 7-17, in a subject; wherein detecting the presence of at least one of the SNPs associated with mastitis is indicative of an increased risk of mastitis in the subject, and the absence of at least one of the SNPs associated with mastitis is indicative of a decreased risk of mastitis in the subject. The increased risk is relative to a subject having an absence of at least one of the SNPs associated with mastitis. The present disclosure also provides use of a composition of the disclosure for screening for, diagnosing, identifying susceptibility to or detecting a risk of developing mastitis, and selecting a subject having an absence of at least one SNP associated with mastitis for a breeding program.

The term "mastitis" refers to an inflammatory disease of the mammary gland caused by infection with contagious and/or environmental pathogenic bacteria, including without limitation, *Escherichia coli, Staphylococcus aureus, Streptococcus agalactiae* and *Streptococcus dysgalactiae*. Symptomatic indications of mastitis infection include, for example, decreased milk production and milk quality, which may be assessed by clinical inspection and/or determining somatic cell count (SCC). Somatic cell score (SCS) is a measure of the average number of somatic cells in milk and is also used to assess milk production and/or milk quality.

The phrase "screening for, diagnosing, identifying susceptibility to or detecting a risk of developing mastitis" refers to a method or process of determining if a subject has an increased risk of or predisposition to or increased susceptibility to mastitis (i.e. by detecting the presence of at least one of the SNPs associated with mastitis), or if a subject does not have an increased risk of mastitis. The increased risk or increased susceptibility to mastitis is measured relative to a subject having an absence of the SNPs associated with mastitis as described herein. For example, SNPs may be associated with mastitis using estimated breeding values (EBV) for somatic cell scores (SCS) in cattle. In one embodiment, SNPs are associated with deregressed EBVs for SCS.

The term "subject" as used herein refers to any member of the animal kingdom, including any lactating mammal, for example a human, dog, cat, horse, cow, bovine, ruminant, bull, pig, sheep, mouse or rat. In one embodiment, the subject is a ruminant animal, such as a bovine (cow or bull). In a further embodiment, the bovine breed may be Holstein, Jersey or Guernsey. In another embodiment, the bovine breed is Holstein. In another embodiment, the bovine breed is Jersey. In a further embodiment, the bovine breed is Guernsey.

In one embodiment, the at least one SNP associated with mastitis comprises at least one of the SNPs in SEQ ID NOS: 7-17.

In another embodiment, the at least one SNP associated with mastitis comprises at least one of the SNPs in SEQ ID NOS: 10, 11, 13 and 14.

In another embodiment, the at least one SNP associated with mastitis comprises at least one of the SNPs in SEQ ID NOS: 9, 10 and 12.

In a further embodiment, the at least one SNP associated with mastitis comprises the SNP in SEQ ID NO: 12.

Another embodiment in the method of screening for, diagnosing, identifying susceptibility to or detecting a risk of developing mastitis comprising detecting the presence or absence of at least one of the SNPs associated with mastitis in a subject, further comprises selecting a subject for a breeding program based on the presence or absence of the SNP associated with mastitis. In one embodiment, a subject having an absence of the SNP associated with mastitis is selected for the breeding program. In another embodiment, the breeding program leads to subjects with reduced incidence of mastitis and enhanced genetic resistance to mastitis.

As used herein, "subjects with reduced incidence of mastitis" include for example subjects exhibiting a reduction in the clinical indications of mastitis, including asymptomatic and symptomatic indications. For example, a reduction in symptomatic indications of mastitis infection includes a reduction in decreased milk production and milk quality. Decreased milk production and milk quality may be assessed by somatic cell count (SCC) and somatic cell score (SCS). For example, decreased values of SCC and SCS correspond with a reduction of mastitis.

The term "subjects with enhanced genetic resistance to mastitis" refers to an increase in the number of subjects in a population of subjects having an absence of at least one of the SNPs associated with mastitis. In another embodiment, subjects with reduced incidence of mastitis and enhanced genetic resistance to mastitis result in improved health of subjects. As used herein "improved health of subjects" refers to subjects not exhibiting clinical indications of mastitis and/or subjects having an absence of at least one of the SNPs associated with mastitis.

The present inventors identified and determined that various haplotypes, namely, AAT, AGT and CAT, in three of the SNPs in the IL-10Rα gene, namely, SNP IL-10Rα 1047C>A; SNP IL-10Rα 1398G>A; and SNP IL-10Rα 1599C>T showed different effects on mastitis as compared to the most frequent haplotype, AGC. The present inventors showed that AAT haplotype had a significant effect on increasing SCS as compared to the most common haplotype AGC. As noted above, the inventors found that SNP IL-10Rα 1398G>A is completely linked to at least three SNPs, namely, SNP IL-10Rα 1512C>T; SNP IL-10Rα 1683T>C; and SNP IL-10Rα 1716 A>G. Therefore, the various haplotypes identified by the inventors, namely, AAT, AGT and CAT, also comprise these at least three SNPs.

Accordingly, in one embodiment, a subject having the AGC SNP haplotype is selected for the breeding program. In another embodiment, a subject having the AAT SNP haplotype is not selected for the breeding program.

As noted above, the present inventors found that the SNPs identified in SEQ ID NOS: 10, 11, 13 and 14 are completely linked; and found that the SEQ ID NOS: 9, 10 and 12 are in linkage disequilibrium. The inventors further identified various haplotypes associated with mastitis using the SNPs in SEQ ID NOS: 9, 10 and 12.

Accordingly, another embodiment of the present disclosure is a method of using linkage disequilibrium to identify alleles or haplotypes associated with mastitis that are present in a subject, for example, by using the techniques described herein to detect SNPs, which have been applied to identify the SNP alleles and haplotypes associated with mastitis described herein. In another embodiment, the present disclosure includes selecting a subject for the breeding program comprising using SNPs that are in linkage disequilibrium and thus are genetically linked to the SNPs associated with mastitis described herein.

Without wishing to be bound by a particular theory, the identified SNPs described herein may alter the gene expression of the IL-10, IL-10Rα, IL-10Rβ, TGF-βI genes and/or the amount of IL-10, IL-10Rα, IL-10Rβ, TGF-βI protein. The risk alleles in IL-10Rβ or IL-10Rβ may affect gene function (i.e. reduced mRNA expression and/or protein) by altering the mRNA secondary structure, the stability of mRNA or RNA splicing. Thus the present disclosure also includes a method of screening for, diagnosing, identifying susceptibility to or detecting a risk of developing mastitis by measuring the mRNA expression or protein of the IL-10Rβ or IL-10Rβ gene, wherein an altered amount compared to control levels is indicative of an increased risk of mastitis.

The methods of the disclosure including screening for, diagnosing, identifying susceptibility to or detecting a risk of developing mastitis, and for selecting a subject having an absence of at least one SNP associated with mastitis for a breeding program can be used in addition to or in combination with other methods.

D. Methods of Screening for, Diagnosing, Identifying Susceptibility to or Detecting a Risk of Developing Johne's Disease, and Selecting for a Breeding Program In one embodiment of the methods and uses for inflammatory disease, the inflammatory disease is Johne's disease. Accordingly, in another embodiment, the at least one SNP identified in a gene associated with inflammatory disease is a SNP associated with MAP infection. In another embodiment, the SNP associated with MAP infection comprises one of the SNPs in SEQ ID NOS: 7-19.

The present inventors have associated the identified individual SNPs and/or SNP haplotypes to Johne's disease. In particular, the present inventors have determined the association of the identified SNPs and/or SNP haplotypes to Johne's disease using an antibody response to *Mycobacterium avium paratuberculosis* (MAP) infection.

Accordingly, one embodiment of the present disclosure is a method of screening for, diagnosing, identifying susceptibility to or detecting a risk of developing Johne's disease comprising determining the presence or absence of at least one of the SNPs associated with MAP infection, such as the SNPs described in SEQ ID NOS: 7-19, in a subject; wherein detecting the presence of at least one of the SNPs associated with MAP infection is indicative of an increased risk of Johne's disease in the subject, and the absence of at least one of the SNPs associated with MAP infection is indicative of a decreased risk of Johne's disease in the subject. The increased risk is relative to a subject having an absence of at least one of the SNPs associated with MAP infection. The present disclosure also provides use of a composition of the disclosure for screening for, diagnosing, identifying susceptibility to or detecting a risk of developing Johne's disease, and selecting a subject having an absence of at least one SNP associated with MAP infection for a breeding program.

The term "Johne's disease" refers to an inflammatory disease, and in particular refers to a chronic inflammatory bowel disease which is caused by an infection with *Mycobacterium avium paratuberculosis* (MAP), which is also described herein as "MAP infection". MAP infection may be assessed by detecting MAP-specific antibodies and/or by detecting MAP bacteria. MAP bacteria may be detected using molecular diagnostics including for example, analyzing fecal culture or performing any other suitable molecular diagnostics test such as PCR. Symptomatic indications for MAP infection include without limitation chronic wasting, diarrhea and/or intestinal lesion.

The phrase "screening for, diagnosing, identifying susceptibility to or detecting a risk of developing Johne's disease" refers to a method or process of determining if a subject has an increased risk of or predisposition to or increased susceptibility to Johne's disease (i.e. by detecting the presence of at least one of the SNPs associated with MAP infection), or if a subject does not have an increased risk of Johne's disease. The increased risk or increased susceptibility to Johne's disease is measured relative to a subject having an absence of the SNPs associated with MAP infection as described herein. For example, MAP infection may be determined by identifying the presence of MAP-specific antibodies.

In one embodiment, the at least one SNP associated with MAP infection comprises one of the SNPs in SEQ ID NOS: 7-19.

In another embodiment, the at least one SNP associated with MAP infection comprises one of the SNPs in SEQ ID NOS: 10, 11, 13 and 14.

In a further embodiment, the at least one SNP associated with MAP infection comprises the SNP in SEQ ID NOS: 9, 10 and 12.

Another embodiment in the method of screening for, diagnosing, identifying susceptibility to or detecting a risk of developing Johne's disease comprising detecting the presence or absence of at least one of the SNPs associated with MAP infection in a subject, further comprises selecting a subject for a breeding program based on the presence or absence of the SNP associated with MAP infection. In one embodiment, a subject having an absence of the SNP associated with MAP infection is selected for the breeding program. In another embodiment, the breeding program leads to subjects with reduced incidence of MAP infection and/or Johne's disease and enhanced genetic resistance to MAP infection and/or Johne's disease.

As used herein, "subjects with reduced incidence of MAP infection and/or Johne's disease" include for example subjects exhibiting a reduction in the clinical indications of MAP infection, including asymptomatic and symptomatic indications. For example, a reduction in indications of MAP infection includes without limitation a reduction in the presence of MAP-specific antibodies, wasting, diarrhea and/or intestinal lesions.

The term "subjects with enhanced genetic resistance to Johne's disease" refers to an increase in the number of subjects in a population of subjects having an absence of at least one of the SNPs associated with MAP infection. In another embodiment, subjects with reduced incidence of Johne's disease and enhanced genetic resistance to Johne's disease result in improved health of subjects. As used herein "improved health of subjects" refers to subjects not exhibiting clinical indications of Johne's disease and/or subjects having an absence of at least one of the SNPs associated with MAP infection.

In another embodiment, reduced incidence of Johne's disease and enhanced genetic resistance to Johne's disease leads to a decrease in the risk of human exposure to MAP infection.

The present inventors also identified and determined that various haplotypes, namely, AAT, CAC and AAC, in three of the SNPs in the IL-10Rα gene, namely, SNP IL-10Rα 1047C>A; SNP IL-10Rα 1398G>A; and SNP IL-10Rα 1599C>T showed different effects on MAP infection as compared to the most frequent haplotype in the positive cohort, AGC. As noted above, the present inventors found that SNP IL-10Rα 1398G>A is completely linked to at least three SNPs, namely, SNP IL-10Rα 1512C>T; SNP IL-10Rα 1683T>C; and SNP IL-10Rα 1716A>G. Therefore, the various haplotypes identified by the inventors, namely, AAT, CAC and AAC, also comprise these at least three SNPs.

The present inventors found that haplotype AGC was more commonly found in the positive cohort and was thus associated with MAP infection. In contrast haplotype AAT was more commonly found in the negative cohort. Accordingly, in one embodiment, a subject having the AAT SNP haplotype is selected for the breeding program. In another embodiment, a subject having the AGC SNP haplotype is not selected for the breeding program.

As noted above, the present inventors found that the SNPs identified in SEQ ID NOS: 10, 11, 13 and 14 are completely linked; and also found that the SEQ ID NOS: 9, 10 and 12 are in linkage disequilibrium. The inventors further identified various haplotypes associated with MAP infection using the SNPs in SEQ ID NOS: 9, 10 and 12.

Accordingly, another embodiment of the present disclosure is a method of using linkage disequilibrium to identify alleles or haplotypes associated with MAP infection that are present in a subject, for example, by using techniques described herein to detect SNPs, which have been applied to identify the SNP alleles and haplotypes associated with MAP infection described herein. In another embodiment, the present disclosure includes selecting a subject for the breeding program comprising using SNPs that are in linkage disequilibrium and thus are genetically linked to the SNPs associated with MAP infection described herein.

Without wishing to be bound by a particular theory, the SNPs described herein may alter the gene expression of the IL-10, IL-10Rα, IL-10Rβ, TGF-βI genes and/or the amount of IL-10, IL-10Rα, IL-10Rβ, TGF-βI protein. The risk alleles in IL-10Rβ or IL-10Rβ may affect gene function (i.e. reduced mRNA expression and/or protein) by altering the mRNA secondary structure, mRNA folding, the stability of mRNA or RNA splicing. Thus the present disclosure also includes a method of screening for, diagnosing, identifying susceptibility to or detecting a risk of developing Johne's disease by measuring the mRNA expression or protein of the IL-10Rβ or IL-10Rβ gene, wherein an altered amount compared to control levels is indicative of an increased risk of Johne's disease.

The methods of the disclosure including screening for, diagnosing, identifying susceptibility to or detecting a risk of developing Johne's disease, and for selecting a subject having an absence of at least one SNP associated with MAP infection for a breeding program can be used in addition to or in combination with other methods.

E. Methods of Detecting SNPs

The methods described in the present disclosure, including for example, screening for, diagnosing, identifying susceptibility or detecting a risk of developing inflammatory diseases, including mastitis and/or Johne's disease and map infection, include detecting the presence or absence of the respective associated SNPs identified and described herein.

A person skilled in the art will appreciate that a number of methods can be used to measure or detect the presence of the SNPs identified in the present disclosure. For example a variety of techniques are known in the art for detecting a SNP within a sample, including genotyping, microarrays, direct sequencing, restriction mapping, Restriction Fragment Length Polymorphism, Southern Blots, SSCP, dHPLC, single nucleotide primer extension, allele-specific hybridization, allele-specific primer extension, oligonucleotide ligation assay, and invasive signal amplification, Matrix-assisted laser desorption/ionization time-of-flight (MALDI-TOF) mass spectrometry, and Fluorescence polarization (FP). Such methods optionally employ the isolated nucleic acid molecules of the disclosure.

Accordingly, in one embodiment, the SNPs are detected by genotyping. Methods of genotyping are well known in the art. In one method, primers flanking the SNP are selected and used to amplify the region comprising the SNP. The amplified region is then sequenced using DNA sequencing techniques known in the art and analyzed for the presence of the SNP alleles.

In another embodiment, the method of detecting a SNP comprises using a probe. For example, an amplified region comprising the SNP is hybridized using a composition comprising a probe specific for the SNP allele under stringent hybridization conditions. For example, isolated nucleic acids that bind to SNP alleles at high stringency may be used as probes to determine the presence of the allele. Nucleic acids may be labeled with a detectable marker. The marker or label is typically capable of producing, either directly or indirectly, a detectable signal. For example, the label may be radioopaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. In one embodiment of the present disclosure, an isolated nucleic acid sequence specifically hybridizes to at least one of the SNPs in SEQ ID NOS: 7-19.

The term "probe" refers to a nucleic acid sequence that will hybridize to a nucleic acid target sequence. In one example, the probe hybridizes to a sequence comprising a specific SNP allele or its complement under stringent conditions, but will not to the corresponding alternative allele or its complement. The length of probe depends on the hybridization conditions and the sequences of the probe and nucleic acid target sequence. In one embodiment, the probe is 8-100, 8-200 or 8-500 nucleotides in length, such as 1-7, 8-10, 11-15, 16-20, 21-25, 26-50, 51-75, 76-100, 101-150 or 151-200 nucleotides in length or at least 200, 250, 400, 500 or more nucleotides in length. In other embodiments, 10, 15, 20 or 25 nucleotides provide a lower end for the aforementioned nucleotide ranges.

The term "hybridize" refers to the sequence specific non-covalent binding interaction with a complementary nucleic acid. By "high stringency conditions" it is meant that conditions are selected which promote selective hybridization between two complementary nucleic acid molecules in solution. Hybridization may occur to all or a portion of a nucleic acid sequence molecule. The hybridizing portion is typically at least 15-20, 21-25, 26-30, 31-40, 41-50 or 50 or more nucleotides in length. Those skilled in the art will recognize that the stability of a nucleic acid duplex, or hybrids, is determined by the Tm, which in sodium containing buffers is a function of the sodium ion concentration and temperature ($Tm=81.5°$ C.$-16.6$ (Log 10 [Na+])$+0.41$(% (G+C)$-600/I$), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm$-5°$ C. for 15 minutes based on the above equation, followed by a wash of 0.2×SSC/0.1% SDS at 60° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

In another embodiment, SNPs may be detected using a primer extension assay. Briefly, an interrogation primer is hybridized to the sequence nucleotides immediately upstream of the SNP nucleotide. A DNA polymerase then extends the hybridized interrogation primer by adding a base that is complementary to the SNP. The primer sequence containing the incorporated base is then detected using methods known in the art. In one embodiment, the added base is a fluorescently labeled nucleotide. In another embodiment, the added base is a hapten-labelled nucleotide recognized by antibodies.

In a further embodiment, SNPs may be detected using restriction enzymes. For example, amplified products can be digested with a restriction enzyme that specifically recognizes sequence comprising one of the SNP alleles, but does not recognize the other allele. PCR may be used to amplify DNA comprising a SNP, and amplified PCR products are subjected to restriction enzyme digestion under suitable conditions and restriction products are assessed. If for example a specific SNP allele corresponds to a sequence digested by the restriction enzyme, digestion is indicative of detecting that particular SNP allele. Restriction products may be assayed electrophoretically as is common is the art.

SNP alleles may also be detected by a variety of other methods known in the art. For example, PCR and RT-PCR and primers flanking the SNP can be employed to amplify sequences and transcripts respectively in a sample comprising DNA (for PCR) or RNA (for RT-PCR). The amplified products are optionally sequenced to determine which of the SNP alleles is present in the sample.

Accordingly, the disclosure provides in one aspect, methods and nucleic acid molecules useful for detecting SNPs. In one embodiment, SNPs are detected by obtaining genomic DNA and primers flanking the SNP are used to amplify the region comprising the mutation. Sequencing is optionally employed to determine which SNP allele is present in the sample. Alternatively, for a sample comprising RNA, the RNA is reverse transcribed, primers flanking the SNP are used to amplify the region comprising the SNP, and sequencing is employed to determine which SNP allele is present. SNPs may also be detected using a composition comprising a probe specific for the mutated sequence.

Alternatively SNP alleles are optionally detected by a variety of other techniques known in the art including microarrays, hybridization assays, PCR based assays, molecular beacons, Dynamic allele-specific hybridization (DASH) and/or combinations of these.

Since it is known that linkage disequilibrium is exhibited in subject populations, for example in cattle populations, SNP alleles or SNP haplotypes that are not identified hereinabove may be determined by techniques known in the art, as applied to the SNP alleles and/or SNP haplotypes identified and described herein.

F. Methods of Treating Inflammatory Diseases & Uses of an Agent to Treat Inflammatory Diseases In another embodiment, the present disclosure provides a method of treating inflammatory disease in a subject comprising (a) detecting the presence or absence of at least one of the SNPs associated with inflammatory disease; and (b) administering to the subject, if at least one of the SNPs associated with disease is present, an effective amount of an agent that treats inflammatory disease.

The present disclosure also provides for use of an agent for treating inflammatory disease. Accordingly, another aspect of the present disclosure includes use of an agent for treating inflammatory disease in a subject, the subject comprising at least one of the SNPs associated with inflammatory disease, wherein the presence of the at least one SNP associated with inflammatory disease has been detected in the subject.

In one embodiment, inflammatory disease is mastitis or Johne's disease. In another embodiment, the at least one of the SNPs associated with inflammatory disease comprises a SNP associated with mastitis and/or a SNP associated with MAP infection. In another embodiment, the SNP associated with mastitis comprises one of the SNPs in SEQ ID NOS: 7-17. In another embodiment, the SNP associated with MAP infection comprises one of the SNPs in SEQ ID NOS: 7-19. In a further embodiment, the method treats mastitis wherein an effective amount of an agent that treats mastitis is administered. In another embodiment, the method treats Johne's disease wherein an effective amount of an agent that treats Johne's disease is administered.

The phrase "treats mastitis" refers to inhibiting mastitis, preventing mastitis, decreasing the severity of mastitis or improving signs and symptoms related to having mastitis. The phrase "treats Johne's disease" refers to inhibiting Johne's disease, preventing Johne's disease, decreasing the severity of Johne's disease or improving signs and symptoms related to having Johne's disease by inhibiting MAP infection, preventing MAP infection, decreasing the severity of MAP infection, or improving signs and symptoms related to having MAP infection.

The term "effective amount" means a quantity sufficient to, when administered to the subject, achieve a desired result, for example an amount effective to inhibit, decrease the severity of, or improve signs and clinical indications related to inflammatory disease, including mastitis and/or Johne's disease, in a subject. Effective amounts of therapeutic may vary according to factors such as the disease state, age, sex, weight of the animal. Dosage or treatment regime may be adjusted to provide the optimum therapeutic response.

The term "agent that treats mastitis" refers to any agent that inhibits mastitis, prevents mastitis, decreases the severity of mastitis or improves signs and symptoms related to having mastitis. Agents suitable for treating mastitis would be known to those skilled in the art.

The term "agent that treats Johne's disease" refers to any agent that inhibits MAP infection, prevents MAP infection, decreases the severity of MAP infection, or improves signs and symptoms related to having MAP infection. Agents suitable for treating Johne's disease would be known to those skilled in the art.

A "treatment" regime of a subject with an effective amount may consist of a single administration, or alternatively comprise a series of applications. The length of the treatment period depends on a variety of factors, such as the severity of the disease, the age of the subject, the concentration and the activity of the agent, or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. The compounds of the present disclosure may be administered before, during or after exposure to inflammatory diseases, including for example, mastitis and/or Johne's disease.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The methods and uses of treating inflammatory disease of the disclosure can be used in addition to or in combination with other options for treatment.

III. Compositions

The present disclosure provides compositions comprising isolated nucleic acid sequences and/or primer pairs that may be used to detect the presence or absence of the SNPs identified and disclosed herein. Methods of detecting SNPs are described elsewhere in the disclosure and may be used in addition to or in combination with the compositions discloses herein.

Accordingly, one aspect of the disclosure is a composition comprising an isolated nucleic acid sequence that specifically hybridizes to at least one of SEQ ID NOS: 7-19 or their complements. The composition is useful as a probe to detect the presence or absence of at least one of the specific SNPs and/or SNP haplotypes associated with mastitis and/or MAP infection, for example, the SNPs identified SEQ ID NOS: 7-19. In another embodiment, the composition comprises at least two isolated nucleic acid sequences that specifically hybridize to SEQ ID NOS: 7-19 or their complements.

The phrase "specifically hybridizes to at least one of SEQ ID NOS: 7-19 or their complements" means that under the same conditions, the isolated nucleic acid sequences in SEQ ID NOS: 7-19 will not hybridize to their corresponding wild-type sequence.

The present inventors have identified primers or primer pairs suitable for detecting the identified SNPs described herein, which are shown in Tables 1 and 5 (SEQ ID NOS: 20-45). Accordingly, one embodiment of the present disclosure includes an isolated nucleic acid molecule that is the amplification product of one of the primer pairs identified in SEQ ID NOS: 20-45.

Another embodiment of the present disclosure includes a composition of two or more isolated nucleotide sequences, wherein the sequences comprise forward and reverse primers that amplify the SNPs identified in SEQ ID NOS: 7-19.

The term "primer" or "primers" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less, such as 8-14 nucleotides. The factors involved in determining the appropriate primer and/or length of primer are readily known to one of ordinary skill in the art.

In another embodiment, the disclosure provides a composition of two or more isolated nucleic acid sequences that are specific primers able to amplify a sequence containing: SEQ ID NO: 7 and/or SEQ ID NO: 8 in the IL-10 gene; and/or SEQ ID NO: 9 and/or SEQ ID NO: 10 and/or SEQ ID NO: 11 and/or SEQ ID NO:12 and/or SEQ ID NO:13 and/or SEQ ID NO: 14 in the IL-10Rα gene; and/or SEQ ID NO: 15 and/or SEQ ID NO: 16 in the IL-10Rβ gene; and/or SEQ ID NO: 17 in the TGF-βI gene; and/or SEQ ID NO: 18 and/or SEQ ID NO: 19 in the NRAMP1 gene.

In one embodiment, primers for amplifying the SNP IL-10 969T>C; NCBI dbSNP ssID: ss104807640 location comprise a SNP Forward primer 5'-AGCCAGCAGCTCT-CAAAGTC-3' (SEQ ID NO:20) and a SNP Reverse primer 5'-GTGTTCAGTGTGGTCCTGGAT-3' (SEQ ID NO:21).

In one embodiment, primers for amplifying the SNP IL-10 1220A>C; NCBI dbSNP ssID: ss104807641 location comprise a SNP Forward primer 5'-GGTAAAGCAGTCCT-GAATCCAA-3' (SEQ ID NO:22) and a SNP Reverse primer 5'-TCCTTCATGGGCCCTATTT-3' (SEQ ID NO:23).

In one embodiment, primers for amplifying the SNP IL-10Rα 1047C>A; NCBI dbSNP ssID: ss104807642 location comprise a SNP Forward primer 5'-TCGTGTTTAT-TGCTCTGGTTGT-3' (SEQ ID NO:24) and a SNP Reverse primer 5'-CCTGCTTCCTTCCCTCCT-3' (SEQ ID NO:25).

In one embodiment, primers for amplifying the SNP IL-10Rα 1398G>A; NCBI dbSNP ssID: ss104807643 location comprise a SNP Forward primer 5'-GGGTTCCTGCTG-GTGACTC-3' (SEQ ID NO:26) and a SNP Reverse primer 5'-GCCAATGCCACTGTCCTC-3' (SEQ ID NO:27).

In one embodiment, primers for amplifying the SNP IL-10Rα 1512C>T; NCBI dbSNP ssID: ss104807644 location comprise a SNP Forward primer 5'-GGGTTCCTGCTG-GTGACTC-3' (SEQ ID NO:28) and a SNP Reverse primer 5'-GCCAATGCCACTGTCCTC-3' (SEQ ID NO:29).

In one embodiment, primers for amplifying the SNP IL-10Rα 1599C>T; NCBI dbSNP ssID: ss104807645 location comprise a SNP Forward primer 5'-AGTGCAGACAGCGGGATCT-3' (SEQ ID NO:30) and a SNP Reverse primer 5'-TTCTTCAGGGGTCTGCAAAG-3' (SEQ ID NO:31).

In one embodiment, primers for amplifying the SNP IL-10Rα 1683T>C; NCBI dbSNP ssID: ss104807646 location comprise a SNP Forward primer 5'-AGTGCAGACAGCGGGATCT-3' (SEQ ID NO:32) and a SNP Reverse primer 5'-TTCTTCAGGGGTCTGCAAAG-3' (SEQ ID NO:33).

In one embodiment, primers for amplifying the SNP IL-10Rα 1716A>G, NCBI dbSNP ssID: ss104807647 location comprise a SNP Forward primer 5'-AGTGCAGACAGCGGGATCT-3' (SEQ ID NO:34) and a SNP Reverse primer 5'-TTCTTCAGGGGTCTGCAAAG-3' (SEQ ID NO:35).

In one embodiment, primers for amplifying the SNP IL-10Rβ 542C>T, NCBI dbSNP ssID: ss104807648 location comprise a SNP Forward primer 5'-GGGAATTCAGGGAATAAAGCA-3' (SEQ ID NO:36) and a SNP Reverse primer 5'-CTGTTTGGGGAATGCAGATT-3' (SEQ ID NO:37).

In one embodiment, primers for amplifying the SNP IL-10Rβ 608A>G, NCBI dbSNP ssID: ss104807649 location comprise a SNP Forward primer 5'-GGGAATTCAGGGAATAAAGCA-3' (SEQ ID NO:38) and a SNP Reverse primer 5'-CTGTTTGGGGAATGCAGATT-3' (SEQ ID NO:39).

In one embodiment, primers for amplifying the SNP TGF-β1 701C>T, NCBI dbSNP ssID: ss104807650 location comprise a SNP Forward primer 5'-CCCTTGCCAAACACTGACA-3' (SEQ ID NO:40) and a SNP Reverse primer 5'-CCTAGCCCAGGCCACTTT-3' (SEQ ID NO:41).

In one embodiment, primers for amplifying the SNP NRAMP1 723C>T, NCBI dbSNP ssID: ss104807654 location comprise a SNP Forward primer 5'-TCCTCTGGAGAAGGGAAAGG-3' (SEQ ID NO:42) and a SNP Reverse primer 5'-ATTCAGAGGCAGGAGTCGAG-3' (SEQ ID NO:43).

In one embodiment, primers for amplifying the SNP NRAMP1 1139C>G, NCBI dbSNP ssID: ss104807655 location comprise a SNP Forward primer 5'-ACATGTGTTGGCCAAGTGAA-3' (SEQ ID NO:44) and a SNP Reverse primer 5'-ACATCCGAGTCCTGAGTGGT-3' (SEQ ID NO:45).

The compositions described herein are useful to identify or detect the presence of or absence of the SNPs and/or SNP haplotypes associated with inflammatory diseases, including for example, mastitis and/or MAP infection.

IV. Kits

Another aspect of the present disclosure is a kit for screening for, diagnosing, identifying susceptibility to or detecting a risk of developing inflammatory disease, for selecting a subject having an absence of at least one of the SNPs associated with inflammatory disease for a breeding program; and for treating inflammatory disease. In one embodiment, the kit comprises a probe that specifically hybridizes to a SNP associated with inflammatory disease as disclosed herein or specific primers that amplify a region comprising a SNP associated with inflammatory disease as disclosed herein and/or instructions for use. The kit can also include ancillary agents. For example, the kits can include vessels for storing or transporting the probes and/or primers; a control; instruments for obtaining a sample; and/or buffers or stabilizers.

In one embodiment, the inflammatory disease is mastitis. In another embodiment, the at least one SNP identified in a gene associated with inflammatory disease is a SNP associated with mastitis. Accordingly, in one embodiment, the kit comprises a probe that specifically hybridizes to a SNP associated with mastitis as disclosed herein or specific primers that amplify a region comprising a SNP associated with mastitis as disclosed herein and/or instructions for use.

In another embodiment, the inflammatory disease is Johne's disease. In another embodiment, the at least one SNP identified in a gene associated with inflammatory disease is a SNP associated with MAP infection. Accordingly, in another embodiment, the kit comprises a probe that specifically hybridizes to a SNP associated with MAP infection as disclosed herein or specific primers that amplify a region comprising a SNP associated with MAP infection as disclosed herein and/or instructions for use. The kit can also include ancillary agents described above.

The above disclosure generally describes the present disclosure. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Summary

Genetic variants in the form of SNPs in candidate anti-inflammatory genes that contribute to host susceptibility to mastitis were identified.

It is known that host genetics play a role in determining an animal's susceptibility to an intramammary infection (IMI). Evidence for this lies in the identification of quantitative trait loci (QTL) on nearly every bovine chromosome for either clinical mastitis or milk somatic cell score (SCS) (Rupp and Boichard 2003), and reported heritability estimates between 0.03 and 0.04 for clinical and subclinical mastitis (Bloemhof et al. 2008; Carlen et al. 2005), and between 0.08 and 0.13 for SCS (Holtsmark et al. 2008; Rupp and Boichard 1999). Milk SCS, a measure of the average number of somatic cells found in milk, is a heritable trait that is positively correlated with the incidence of clinical and subclinical mastitis ($0.66 < r < 0.94$) (de Haas et al. 2008). This indirect relationship between milk SCS and the incidence of mastitis has allowed the dairy industry to use estimated breeding values (EBVs) for SCS to select sires and dams with enhanced genetic resistance to mastitis for breeding programs. Since the large number of QTL associated with clinical mastitis and SCS suggests that the resistance to mastitis trait is polygenic in nature, the identification of SNPs that contribute to variation in these traits will require the interrogation of numerous genes, some of which are likely to be involved in regulating inflammation.

The host response to acute mastitis can generally be divided into two complementary phases: the pro-inflammatory phase associated with the onset of IMI, and the subsequent anti-inflammatory phase associated with its resolution. This innate host response may not only be sufficient to control infection, it also provides time for activation of the acquired immune system, which provides long-term protection to the host via the production of antigen-specific lymphocytes (Medzhitov and Janeway, Jr. 1997). From the host's perspective, rapid elicitation of the pro-inflammatory phase is beneficial, since it promotes the activation and recruitment of bactericidal phagocytic cells, such as neutrophils and macrophages into the mammary gland to control the spread of infection. However, if this phase is excessive or prolonged, it can contribute to mammary tissue damage as a result of over-exposure to the cytotoxic enzymes and reactive oxygen species released by these cells. The subsequent anti-inflammatory phase is therefore critical for protecting the host tissues from excessive inflammation, however, if it occurs prematurely or in excess, it also has the potential to compromise the host defense against IMI. Clearly, it is necessary for these two phases to be tightly regulated by a complex system of checks and balances in order to ensure that a chronic inflammatory or an infective state does not ensue (Brown et al. 2007).

A select group of pro- and anti-inflammatory cytokines and their receptors are likely involved in regulating the mammary inflammatory response during IMI; two such candidates are interleukin (IL-) 10 and transforming growth factor (TGF-) β1. These cytokines are known to have a prominent anti-inflammatory role at mucosal surfaces, partly through the action of regulatory T cells (CD4+CD25+) (Bingisser and Holt 2001; Lehner 2008; MacDermott 1996). During *E. coli*, *S. aureus*, or *Mycoplasma* bovis IMI, levels of IL-10 are increased in mammary gland tissue and in milk (Bannerman et al. 2004; Kauf et al. 2007; Zhu et al. 2008). Furthermore, rodent studies have demonstrated that the administration of exogenous IL-10 reduces the fever response in rats challenged with lipopolysaccharide (LPS) or heat-killed *S. aureus* (Cartmell et al. 2003). Higher levels of TGF-β1 have also been detected in the milk of dairy cattle following an *E. coli* or *S. aureus* IMI (Bannerman et al. 2006; Chockalingam et al. 2005).

A. Sample Population and Trait Records

The sample population consisted of 500 Holstein, 83 Jersey and 50 Guernsey bulls. Holstein bulls were selected across 25 sire families on the basis of extreme EBVs for SCS and protein yield. Each sire family consisted, on average, 20±4.5 sons (max=27, min=10). Jersey and Guernsey bulls were selected without pre-evaluation of EBVs and were distributed amongst 33 (max=8, min=1) and 30 (max=4, min=1) sire families, respectively. Pedigree data and EBVs for SCS were obtained from the Canadian Dairy Network (Guelph, Ontario, Canada) genetic evaluation database (April 2008). Somatic cell score is calculated as $\log_2(SCC/100,000)+3$; where SCC is the somatic cell count per milliliter of milk (Reents et al. 1995).

B. DNA extraction and snp discovery

Genomic DNA was extracted from semen generously provided by the Semex Alliance (Guelph, Ontario, Canada) using a phenol-chloroform procedure (Winfrey et al. 1997) with slight modifications to accommodate the bench-top centrifuge and the rotor. Quality and quantity of DNA were monitored by ultraviolet spectrometry.

All SNPs were identified by sequencing PCR amplicons from each candidate gene using a DNA pool constructed with DNA from 40 Holstein bulls according to Pant et al. (Pant et al. 2007) and Sharma et al. (Sharma et al. 2006). Briefly, for each bull, genomic DNA was extracted from semen and adjusted to a concentration of 5 ng/μl after several rounds of quantification using the Quant-iT PicoGreen dsDNA reagent (Invitrogen, Carlsbad, Calif., USA) followed by dilution. The resultant DNA pool was amplified using the Repli-g Ultrafast mini kit (Qiagen, Santa Clara, Calif., USA) and used as a template for PCR amplification of the 5' untranslated region and coding exons of each candidate gene. The PCR products were sequenced in both 5' and 3' orientation using an ABI Prism 3730 DNA sequencer (Applied Biosystems, Foster City Calif., USA), and SNPs were identified by visual inspection of the electropherograms. Six genes were selected for SNP discovery, IL-10 [NCBI-GeneID: 281246; SEQ ID NO:1], IL-10R subunits a [NCBI-GeneID: 513478; SEQ ID NO:2] and 13 [NCBI-GeneID: 767864; SEQ ID NO:3], TGF-β class I [NCBI-GeneID: 282089; SEQ ID NO:4], and TGF-βR type I [NCBI-GeneID: 282382] and II [NCBI-GeneID: 535376; SEQ ID NO:5]. Sequences were compared against GLEAN models using the Apollo Genome Annotation and Curation Tool to confirm correct gene structure (Version 1.6.5) (Lewis et al. 2002). In the event of a disagreement between respective GLEAN and NCBI gene models, as was the case for IL-10Rα, the GLEAN model was chosen.

In total, eleven SNPs were identified: two in IL-10 (969T>C and 1220A>C); six in IL-10Rα (1047C>A, 1398G>A, 1512C>T, 1599C>T, 1683T>C, and 1716A>G); two in IL-10Rβ (542C>T, and 608A>G), and one in TGF-61 (701C>T). Primers for SNP discovery were designed using the software Primer3 (Rozen and Skaletsky 2000), and can be found in Table 1. All SNPs were submitted to NCBI dbSNP and will be released with Build 130 (Table 1). Table 1 also indicates whether the mutation is synonymous (Syn) or non-synonymous (Non) in addition to identifying the primer set, forward (F) or reverse (R).

C. Materials and Methods

C.1 Genotyping and Haplotype Reconstruction

Genotyping of SNPs was conducted using the iPLEX MassARRAY system (Sequenom inc., San Diego, Calif., USA). One of the eleven SNPs, IL-10 1220A>C, was not genotyped using this platform due to failed primer design. Two groups of SNPs, IL-10Rα 1398G>A, 1512C>T, 1683T>C and 1716A>G, and IL-10Rβ 542C>T and 608A>G appeared to be in complete linkage, since nearly all of the genotypes matched (Pearson's $r^2$>98%). Thus, all but one SNP from each group was removed, resulting in six SNPs included in the analysis. For haplotype analysis, only the SNPs in IL-10Rα (1047C>A, 1398G>A, and 1599C>T) were included, since none of the other genes contained multiple SNPs and were located in different chromosomes. For both the SNP and haplotype association analyses, only the Holstein group was analyzed, since the Jersey and Guernsey groups did not contain a sufficient number of animals. Haplotypes were reconstructed using the software HAPPROB (Boettcher et al. 2004).

C.2 Statistical Analysis

Assessment of Hardy-Weinberg equilibrium (HWE) was performed using the package 'hardyweinberg' (Graffelman and Camarena 2008) in R, version 2.6.2 (R Development Core Team 2008). Comparison of allele frequencies across breeds was performed using a Fisher's exact test in R. Tests for significance of pair-wise linkage disequilibrium (LD) were performed as described in Krawetz and Womble (Krawetz S A and Womble D D 2003):

$$x^2_{AB, df=1} = \eta \times \frac{(\rho_{AB} - \rho_A \rho_B)^2}{\rho_A \rho_a \rho_B \rho_b}$$

where: η=number of bulls genotyped; $\rho_{AB}$=frequency of haplotype AB; $\rho_A, \rho_a$=frequency of alleles A and a, respectively; $\rho_B, \rho_b$=frequency of alleles B and b, respectively.

Tests for association of SNPs with deregressed EBVs for SCS, using the software ASREML (Gilmour et al. 2006). Analyses were performed separately for SNPs located in different chromosomes. The model included linear regression on the number of alleles and the bull polygenic effect:

$$y_i = \mu + \sum_{k=1}^{s} \beta_k Gen_k + Poly_i + \epsilon_i$$

where: $y_i$=deregressed SCS EBV for the i-th bull; $\mu$=overall mean; $\beta$=linear regression coefficient (allele substitution effect) for the k-th SNP; Gen=genotype of the k-th SNP recoded as number of alleles (0, 1 and 2), where s is the number of SNPs on the particular chromosome considered; Poly; =random polygenic effect of the i-th bull; and $\epsilon_i$=random residual effect.

All of the available pedigree information was used for modeling the covariance among polygenic effects throughout the additive relationship matrix. Haplotype analysis was performed using a similar model, only $\beta_k Gen_k$ is replaced by:

$$\sum_{k=1}^{h} \beta_k Hap_k$$

where: $\beta_k$=linear regression coefficient (haplotype effect) for the k-th haplotype; $Hap_k$=the probability for the k-th haplotype, where h is the number of observed haplotypes (7). In both cases the analyses were weighted by the number of daughters of each bull.

Experimental-wise significance levels for all tests were determined by Bonferroni correction.

D. Results

Due to nearly matching genotypic frequencies (Pearson's $r^2$>98%), four SNPs in IL-10Rα (1398G>A, 1512C>T, 1683T>C and 1716A>G), and both SNPs in IL-10Rβ (542C>T and 608A>G) were assumed to be completely linked.

Hence, all but one SNP from each of these genes was dropped from analysis in order to minimize redundancy. There were three instances in which a SNP, or group of linked SNPs, was not in HWE (comparison-wise p<0.05): the group of four linked SNPs in IL-10Rα in Holstein and Jersey, IL-10Rα 1047C>A in Jersey and the two linked SNPs in IL-10Rβ in Guernsey. After correcting for multiple testing using Bonferroni's procedure, only IL-10Rα 1047C>A in Jersey was statistically significant at an experimental-wise threshold of 10% (p<0.006).

Table 2 summarizes the genotype and allele frequencies of SNPs in candidate genes across three dairy breeds after records containing missing genotypes were removed. Data is presented as Genotype number (%), genotypic count (frequency); allele % and allelic frequency. Comparison of allele frequencies between breeds using Fisher's exact test revealed an anticipated trend in which the Holstein group differed significantly (experimental-wise p<0.01) from the Jersey and Guernsey group, and the Jersey and Guernsey group seldom differed. The only exceptions were for SNPs IL-10Rα 1398G>A and IL-10Rβ 542C>T, where no differences were identified, and for SNP TGF-β1 701C>T, where the Holstein and Guernsey group both differed from the Jersey group (Table 2).

Table 3 demonstrates the SNP effect on somatic cell score in Canadian Holstein bulls. The data is presented as: $\alpha \pm SE$, allele substitution effect±standard error. One SNP, IL-10Rα 1599C>T, showed a significant association with deregressed EBVs for SCS, with an allele substitution effect of 0.347±0.141 for the 'T' allele. This effect was retained at an experimental-wise threshold of 10% (p<0.017). The other SNPs in IL-10Rα, 1047C>A and 1398G>A, approached significance for SCS, displaying allele substitution effects of 0.255±0.142 and 0.254±0.140, respectively (Table 3).

Table 4 shows the haplotypes for SNPs 1047C>A, 1398G>A and 1599C>T in IL-10Rα, their frequency in Canadian Holstein bulls and contrasts against the most frequent haplotype (AGC) for somatic cell score. The data is presented as: (3±SE, haplotype effect±standard error; Pval, comparison-wise p-value; + experimental-wise p<0.10. After haplotype reconstruction for the three SNPs in IL-10Rα (1047C>A, 1398G>A, 1599C>T), seven haplotypes were identified, AGC (40.8%), AAT (16.8%), AAC (16.0%), CAC (11.0%), AGT (7.4%), CGC (5.0%) and CAT (3.0%). Four haplotypes showed significantly different effects on SCS as compared to the most frequent haplotype (AGC): AAT (p=0.003), AGT (p=0.029), CGC (p=0.042) and CAT (p=0.025). Only haplotype AAT met an experimental-wise significance at 10% for SCS (Table 4).

E. Discussion

The present inventors sought to identify genetic variants in the form of SNPs in candidate anti-inflammatory genes that contribute to host susceptibility to mastitis due to IMI in dairy cows. The SNP IL-10Rα 1599C>T was found to have significant comparison-wise associations with deregressed EBVs for SCS and retained its significance at an experimental-wise significance of 10% (Table 3). When haplotypes were constructed for the IL-10Rα gene, a single haplotype, AAT, was found to be strongly associated with SCS and showed a significantly different effect compared to the most prominent haplotype, AGC (Table 4).

The associations observed for SNPs in IL-10Rα indicate that this gene influences SCS and the susceptibility to mastitis. This is supported by studies that have shown that IL-10 is induced after intramammary challenge with Gram-negative and -positive bacteria and during the course of clinical mastitis (Oviedo-Boyso et al. 2007), implicating it, as well as its receptor, in the pathogenesis of mastitis.

The IL-10 receptor complex is a heterotetramer composed of two of each subunit, IL-10Rα and IL-10Rβ. The IL-10Rα subunit is chiefly responsible for ligand-binding, whereas IL-10Rβ appears to mediate signal transduction (Moore et al. 2001). Unlike IL-10Rβ, which is constitutively expressed on most cells, inducible IL-10Rα appears to be the major determinant of cellular IL-10 responsiveness (Ding et al. 2001; Tamassia et al. 2008). Alignment of bovine IL-10Rα with its mouse orthologue reveals that all of the SNPs identified in the present study, with exception to 1047C>A, are most likely located in the receptor's cytoplasmic domain. The SNPs IL-10Rα 1398G>A, 1512C>T and 1599C>T, for example, align with a region within the cytoplasmic domain that defines cellular responsiveness to IL-10. Likewise, SNPs IL-10Rα 1683T>C and 1716A>G align with a region responsible for mediating signals that stimulate cellular proliferation (Ho et al. 1995). Gasche and colleagues (Gasche et al. 2003) found that a non-synonymous SNP in the cytoplasmic domain of human IL-10Rα rendered monocytes hyporesponsive to IL-10 after LPS challenge, and that this effect was likely due to a loss-of-function. The cytoplasmic domain of IL-10Rα is also known to be important for proper internalization, and receptors carrying mutant forms of this domain exhibit prolonged signaling (Wei et al. 2006).

Unlike the above study by Gasche and colleagues, the SNPs identified in IL-10Rα in this example were all synonymous mutations and are therefore traditionally viewed as being phenotypically silent since they do not alter the amino acid sequence of the subsequent protein. However, a number of recent studies have demonstrated that synonymous mutations may affect gene function by altering mRNA secondary structure, stability, splicing (Chamary and Hurst 2005; Salomons et al. 2007), and protein expression (Shah et al. 2008). Given this, further investigation into the potential impact of these SNPs on IL-10R expression is justified.

A multiple regression model was used for SNPs residing on the same chromosome, namely those in the IL-10Rα gene. The reason for this approach is due to the fact that SNPs in proximity to one another are likely also in linkage disequilibrium (LD), and in turn, probably have a degree of correlation between their genotypes. This poses a problem in association studies since highly correlated SNPs are likely to show similar effects, thus, making it difficult to discern which SNP is the causal variant. Under low to moderate LD the confounding effect of collinearity can be accounted for using a multiple regression approach, which will give a better estimate of the actual effect (Malo et al. 2008). However, this also leads to a loss of power, manifested by inflated standard error for each estimated regression coefficient, and thus, reducing the significance of the resultant associations (Stinker and Glantz 1985). The pair-wise LD ($r^2$) between SNPs IL-10Rα 1047C>A and 1599C>T, and 1398G>A and 1599C>T, was 0.015 and 0.09, respectively, and significant at a comparison-wise threshold of p<0.01. This warrants the use of a multiple regression approach. The subsequent identification of a significant SNP effect for IL-10Rα 1599C>T further supports its characterization as a causal marker. Interestingly, a QTL for SCS has been reported on BTA15 approximately 3-5 Mb downstream of IL-10Rα (Ashwell et al. 2004).

In summary, the present example has shown associations between SCS and SNPs in the IL-10Rα gene. One SNP in particular, 1599C>T, showed an allele substitution effect of 0.347±0.141 and retained its significance at an experimental-wise threshold of 10%.

Another SNP in IL-10Rα, 1398G>A identified also plays a role in defining a cow's lactation persistency (LP) and average SCS.

Furthermore, a single haplotype in IL-10Rα, AAT, was shown to have a significant effect on increasing SCS, as compared to the most common haplotype. This would indicate that increasing the frequency of the AGC haplotype in a dairy herd while decreasing the frequency of AAT may have a beneficial effect of lowering average SCS. Therefore, the results presented here indicate that a selection program incorporating these markers could have a beneficial influence on the average SCS and productivity of a dairy herd by reducing susceptibility to mastitis.

Example 2

Summary

Genetic variants in the form of SNPs in candidate anti-inflammatory genes that contribute to host susceptibility to *Mycobacterium avium paratuberculosis* (MAP) infection were identified.

Since resistance to MAP infection is likely polygenic in nature, it is essential that multiple genes be investigated for their contribution to disease resistance. Therefore, the focus was to identify single nucleotide polymorphisms (SNPs) in several immune-related genes and investigate their association with MAP infection status in dairy cattle. Interleukin (IL)-10 and its receptor (subunits IL-10Rα and IL-10Rβ), transforming growth factor (TGF)-β1 and its receptors (TGF-βR type I and II), and natural resistance-associated macrophage protein 1 (NRAMP1) were investigated based on their previous associations with various types of human IBD (Tamizifar et al., 2008; Tedde et al., 2008; Sechi et al., 2008 and Zaahl et al., 2006). IL-10 and TGF-β1 collectively act to control the host inflammatory response to microbial antigens; IL-10 primarily operates as a feedback inhibitor of T cell responses, and TGF-β1's major function is to maintain T cell tolerance to self and commensal antigens by influencing the differentiation and homeostasis of effector and regulatory T cells (Li et al., 2008). Natural resistance-associated macrophage protein 1, also known as solute carrier family 11 member 1 (SLC11A1), is an iron transporter that exhibits pleiotropic effects on the early innate macrophage response to intracellular bacteria (McDermit et al, 2006).

A. Cohort Population

Six commercial Holstein operations in Southwestern and Eastern Ontario were selected for sample collection based on a previous history of high prevalence MAP infection. Blood was collected between the months of July and September 2007 via the coccygeal (tail) vein from more than 400 dry and lactating cows ranging in age, breed, stage of lactation, infection status, and history of MAP screening. The protocol for collection was approved by the University of Guelph animal care committee. Current infection status was determined by identifying the presence of MAP-specific plasma antibodies using the commercially available HerdChek M. pt. Antibody ELISA Test Kit (IDEXX Laboratories, Westbrook, M E, USA) according to manufacturer's instructions. Infection-free animals making up the healthy (negative) control cohort (n=242) included animals that were older than 4.5 years of age and had tested negative for MAP infection in previous years (n=197), and those that were older than 5.5 years of age without previous screening (n=45). The mean age of this cohort was 6.4 years (range, 4.5 to 12.7 years). The infected (positive) cohort (n=204) was made up of animals that were considered to be infected based on the presence of MAP-specific plasma antibodies (n=16), and a second group of animals considered to be infected based on milk MAP-specific antibodies screening carried out by Canwest DHI (Guelph, ON, CAN) (n=188); these milk samples were generously provided between July 2006 and November 2007, and due to client anonymity, information such as age, pedigree and location was not available. Genomic DNA was extracted from the buffy coat of blood samples using the DNeasy blood and tissue kit (Qiagen, Santa Clara, Calif., USA), and from milk according to methods previously described (Murphy et al., 2002).

B. Single Nucleotide Polymorphism (SNP) Discovery

All SNPs were identified by sequencing PCR amplicons from each candidate gene using a DNA pool constructed with DNA from 40 Holstein bulls according to methods described in previous studie (Pant et al., 2007; Sharma et al. 2006). Briefly, for each bull, genomic DNA was extracted from semen and adjusted to a concentration of 5 ng/μl after several rounds of quantification using the Quant-iT PicoGreen dsDNA reagent (Invitrogen, Carlsbad, Calif., USA) followed by dilution. The resultant DNA pool was amplified using the Repli-g Ultrafast mini kit (Qiagen, Santa Clara, Calif., USA), and was then used as a template for PCR amplification of the 5' untranslated region and coding exons of each candidate gene. Primers were designed using. Primer3 (Rozen et al.

2000). PCR amplicons were sequenced in both 5' and 3' orientation using an ABI Prism 3730 DNA sequencer (Applied Biosystems, Foster City Calif., USA), and SNPs were identified by visual inspection of the electropherograms. Seven genes were selected for SNP discovery, IL-10 [NCBI-GeneID: 281246; SEQ ID NO:1], IL-10Rα [NCBI-GeneID: 513478; SEQ ID NO:2], IL-10Rβ [NCBI-GeneID: 767864; SEQ ID NO:3], TGF-β1 [NCBI-GeneID: 282089; SEQ ID NO:4], TGF-βR type I [NCBI-GeneID: 282382] and TGF-6R type II [NCBI-GeneID: 535376; SEQ ID NO:5] and NRAMP1 [NCBI-GeneID: 282470; SEQ ID NO:6]. Sequences were compared against GLEAN models using the Apollo Genome Annotation and Curation Tool to confirm correct gene structure (Version 1.6.5) (Lewis et al., 2002). In the event of a disagreement between respective GLEAN and NCBI gene models, as was the case for IL10Rα, the GLEAN model was chosen.

In total, thirteen SNPs were identified: two in IL-10 [969T>C (ss104807640) and 1220A>C (ss104807641)]; six in IL-10Rα [1047C>A (ss104807642), 1398G>A (ss104807643), 1512C>T (ss104807644), 1599C>T (ss104807645), 1683T>C (ss104807646), and 1716A>G (ss104807647)]; two in IL-10Rβ [542C>T (ss104807648), and 608A>G (ss104807649)], one in TGF-β1 [701C>T (ss104807650)], and two in NRAMP1 [723C>T (ss104807654) and 1139C>G (ss104807655)]. All SNPs were submitted to NCBI dbSNP (Build 130).

C. Materials and Methods

C.1. Genotyping and Haplotype Reconstruction

SNP genotyping was conducted using the iPLEX MassARRAY system (Sequenom inc., San Diego, Calif., USA). Table 5 shows the characteristics of SNPs discovered in MO, IL10Rα/β, TGF-β1, and NRAMP1 genes. Two of the thirteen SNPs, IL-10 1220A>C, and NRAMP1 723C>T, were not genotyped using this assay due to failed primer design or inadequate quality of results (Table 5). Two groups of SNPs, IL-10Rα 1398G>A, 1512C>T, 1683T>C and 1716A>G, and IL-10Rβ542C>T and 608A>G appeared to be completely linked due to nearly matching genotype records (Pearson's $r^2 \geq 98\%$), thus all but one SNP from each group was removed from the analysis. For haplotype analysis, only the SNPs in IL-10Rα were included since no genes contained multiple unlinked SNPs, or reside on the same chromosome. The haplotypes were reconstructed in both cohorts using PHASE (version 2.1) (Stephens et al., 2003).

C.2 Statistical Analysis

SNP associations and Akaike's information criterion (AIC) were determined using a logistic regression model (PROC LOGISTIC) in SAS (version 9.1, SAS Institute Inc., NC, USA) as described in Zeng et al. (2005):

$$y_i = i + \sum_{k=1}^{s}(a_k w_k + d_k v_k) + e_i$$

where: $\gamma_i$=MAP infection status (1=infected, 0=healthy) for the i-th cow; μ=overall mean; s=number of SNPs on the particular chromosome considered; a=additive effect for the k-th SNP; w=genotype of the k-th SNP recoded as number of alleles (0, 1 and 2); d=dominance effect for the k-th SNP; v=genotype of the k-th SNP recoded as homozygote or heterozygote (0 and 1); and $\epsilon_i$=random residual effect. Haplotype analysis was performed in SAS using a similar model, only $$\sum_{k=1}^{s}(a_k w_k + d_k v_k)$$

is replaced by $$\sum_{k=1}^{h} \hat{a}_k Hap_k;$$

where: $\beta_k$=linear regression coefficient (haplotype effect) for the k-th haplotype; $Hap_k$=the probability for the k-th haplotype, where h is the number of observed haplotypes. Experimental-wise significance levels for all tests were determined by Bonferroni correction.

To assess multicollinearity, principal component analysis (PCA) was performed using PROC PRINCOMP in SAS, followed by calculation of the condition index (Belsley et al., 1991):

$$K = \frac{\lambda_{max}}{\lambda_{min}}$$

where: $\lambda_{max}, \lambda_{min}$=the largest and smallest eigen value for the variables considered, respectively.

D. Results

Due to nearly matching genotypic frequencies (Pearson's $r^2 \geq 98\%$) it was assumed that four SNPs in IL-10Rα (1398G>A, 1512C>T, 1683T>C and 1716A>G), and both SNPs in IL-10Rβ (542C>T and 608A>G) were linked. Hence, all but one SNP from each of these genes was dropped from analysis in order to minimize redundancy. Although not in complete linkage, the remaining SNPs in IL-10Rα (1047A>C, 1398G>A and 1599C>T) are relatively close to one another, and appear to be in significant linkage disequilibrium in Canadian Holstein bulls. As such, it was a concern that there would be a high degree of correlation (multi-colinearity) between them in the present dataset, thereby inflating standard error of parameter estimates and thus, reducing the significance of resultant associations (Slinker et al., 1985). Principal component analysis (PCA), followed by calculation of the condition index, suggests that these three SNPs were in a state of strong multi-co-linearity (K>140), whereas the removal of any one SNP returned the condition index to an acceptable range (7.7<K<10.5) (Meloun et al., 2002). Model selection based AIC subsequently determined that IL-10Rα 1599C>T was the most appropriate SNP to remove from the multiple regression model.

Logistic regression analysis revealed that only the SNPs in IL-10Rα were associated to MAP infection.

Table 6 indicates the genotypic frequencies and associations of SNPs in IL10, IL10Rα/13, TGF-β1, and NRAMP1 genes with MAP infection status. The SNP IL-10Rα 1047A>C showed a moderate but non-significant additive effect on MAP infection status (OR, 1.77 (0.97-3.25), p=0.064), in which the 'A' allele was more prominent in the positive cohort (Table 6). The group of linked SNPs, IL-10Rα 1398G>A, 1512C>T, 1683T>C and 1716A>G, were found to have a strong additive and dominance relationship with MAP infection status (OR, 1.92 (1.28-2.89), p<0.002, and 2.13 (1.35-3.38), p<0.002, respectively), which were retained at an experimental-wise significance of 5% (Table 6). The results suggest that the linked allele GCTA are in over-dominance over the ATCG allele, and more prominent in the positive cohort.

Haplotype reconstruction of the three unlinked SNPs in IL-10Rα (1047A>C, 1398G>A and 1599C>T) identified four combinations using PHASE. Table 7 shows the haplotype frequencies in the 3' coding region of IL10Rα gene and their association with MAP infection status. Haplotype AAC was found in less than 1% of the sample population, whereas haplotypes AGC, AAT and CAC represented 56%, 24% and 19% of the entire sample population, respectively. Individual tests for haplotype association with MAP infection revealed that haplotype AGC was more commonly found in the positive cohort (p=0.018) and haplotype AAT in the negative cohort (p=0.030) (Table 7). Haplotype contrasts against the most frequent haplotype, AGC, identified a significant effect for haplotype AAT (p=0.013)(Table 7), which was retained at an experimental-wise level of 5%.

E. Discussion

In the following cohort, two significant associations with MAP infection status were observed for the IL-10Rα gene. First, a strong association between the linked bovine SNPs IL-10Rα 1398G>A, 1512C>T, 1683T>C and 1716A>G and MAP infection status was detected. For these SNPs, the linked allele GCTA is over-dominant over the ATCG allele, and more prominent in the MAP positive cohort. Second, when haplotype analysis was performed on SNPs IL-10Rα 1047C>A, IL-10Rα 1398G>A and IL-10Rα 1599C>T, equally strong, inverse associations for the haplotypes AGC and AAT with MAP infection status were observed. Considering the strong individual relationship of IL-10Rα 1398G, 1512C, 1683T and 1716A, with MAP infection status, it is not unreasonable to assume that these linked SNPs are the primary contributor to these associations. Contrasts indicated a strong, significant effect in reducing the proportion of infected animals when replacing the most frequent haplotype AGC, with AAT. This would suggest that it may be possible to increase resistance to MAP at the population level by increasing the frequency of the AAT haplotype through selective breeding.

Interleukin-10 has emerged as an essential immunoregulatory cytokine during bacterial infections. In the context of *Mycobacterium* spp. for example, IL-10 helps to control excessive T helper 1 and CD8+ T cell responses that contribute to the immunopathology associated with infection; it also prevents the overproduction of IL-4, IL-5, and IL-13, which can lead to severe fibrosis during the T helper 2 response (Couper et al., 2008) This may be particularly relevant at mucosal surfaces, since human studies have implicated functional SNPs in the IL-10 gene as risk factors for IBD (Tedde et al., 2008) and tuberculosis (Ates et al., 2008). In cattle, IL-10 is up-regulated during subclinical and clinical MAP infections (Karcher et al., 2008 and Khalifeh, 2004), and its neutralization has been shown to promote the activation of MAP-infected bovine macrophages and subsequent killing of the organism (Weiss et al., 2005). Similar findings have also been demonstrated with human infection studies performed in vitro using *Mycobacterium tuberculosis* (Fietta et al., 2001; Al-Attyiah et al., 2008).

Although the present example found no association between variants in the bovine IL-10 gene and MAP infection, it did provide evidence that variants in the IL-10Rα gene, which encodes the ligand-binding subunit of the IL-10R and is a major determinant of IL-10 responsiveness (Ding et al., 2001; Tarnassia et al., 2008), contributes to susceptibility to MAP infection. The present inventors are unaware of previous studies indicating that variants in the IL-10R gene influence the susceptibility to *mycobacterium* infection. In support of this, associations have been reported between SNPs in the human IL-10Rα and p genes and the level of IL-10 expression in mucosal tissues (Simhan et al., 2008). Furthermore, based on alignment with the murine homologue, all of the SNPs identified within IL-10Rα, with exception to 1047C>A, appear to code for a region of the cytoplasmic domain that defines cellular responsiveness to IL-10 and mediates cellular proliferation (Ho et al., 1995). Traditionally, synonymous SNPs are viewed as "silent" and thus may not warrant functional validation, however, several studies addressing the role of codon usage bias, as well as mRNA folding, have reported otherwise (Duan et al., 2003; Charnary et al., 2005; Salomons et al., 2007).

In conclusion, several SNPs were identified in the bovine genes encoding IL-10, IL-10Rα, IL-10Rβ, TGF-β1, and NRAMP1. A strong association between a group of linked synonymous SNPs in the 3' coding region of IL-10Rα, 1398G>A, 1512C>T, 1683T>C and 1716A>G, and MAP infection status Canadian dairy cattle was established. Haplotype reconstruction of the SNPs in IL-10Rα also revealed a strong association with MAP infection status. These results provide evidence that variants in IL-10Rα contribute to susceptibility to MAP infection in dairy cattle.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Characteristics of SNPs discovered in bovine IL-10 and IL-10Rα and β and TGF-β1.

| Gene | SNP | dbSNP ssID | Region | Mutation | Primer set (5'-3') |
|---|---|---|---|---|---|
| IL-10 | 969T>C (SEQ ID NO: 7) | ss104807640 | 5' | | F: AGCCAGCAGCTCTCAAAGTC (SEQ ID NO: 20) R: GTGTTCAGTGTGGTCCTGGAT (SEQ ID NO: 21) |
| | 1220A>C (SEQ ID NO: 8) | ss104807641 | 5' | | F: GGTAAAGCAGTCCTGAATCCAA (SEQ ID NO: 22) R: TCCTTCATGGGCCCTATTT (SEQ ID NO: 23) |

TABLE 1-continued

Characteristics of SNPs discovered in bovine IL-10 and IL-10Rα and β and TGF-β1.

| Gene | SNP | dbSNP ssID | Region | Mutation | Primer set (5'-3') |
|---|---|---|---|---|---|
| IL-10Ra | 1047C>A (SEQ ID NO: 9) | ss104807642 | Coding | Syn | F: TCGTGTTTATTGCTCTGGTTGT (SEQ ID NO: 24) R: CCTGCTTCCTTCCCTCCT (SEQ ID NO: 25) |
| | 1398G>A (SEQ ID NO: 10) | ss104807643 | Coding | Syn | F: GGGTTCCTGCTGGTGACTC (SEQ ID NO: 26) R: GCCAATGCCACTGTCCTC (SEQ ID NO: 27) |
| | 1512C>T (SEQ ID NO: 11) | ss104807644 | Coding | Syn | F: GGGTTCCTGCTGGTGACTC (SEQ ID NO: 28) R: GCCAATGCCACTGTCCTC (SEQ ID NO: 29) |
| | 1599C>T (SEQ ID NO: 12) | ss104807645 | Coding | Syn | F: AGTGCAGACAGCGGGATCT (SEQ ID NO: 30) R: TTCTTCAGGGGTCTGCAAAG (SEQ ID NO: 31) |
| | 1683T>C (SEQ ID NO: 13) | ss104807646 | Coding | Syn | F: AGTGCAGACAGCGGGATCT (SEQ ID NO: 32) R: TTCTTCAGGGGTCTGCAAAG (SEQ ID NO: 33) |
| | 1716A>G (SEQ ID NO: 14) | ss104807647 | Coding | Syn | F: AGTGCAGACAGCGGGATCT (SEQ ID NO: 34) R: TTCTTCAGGGGTCTGCAAAG (SEQ ID NO: 35) |
| IL-10Rβ | 542C>T (SEQ ID NO: 15) | ss104807648 | Coding | Non | F: GGGAATTCAGGGAATAAAGCA (SEQ ID NO: 36) R: CTGTTTGGGGAATGCAGATT (SEQ ID NO: 37) |
| | 608A>G (SEQ ID NO: 16) | ss104807649 | Coding | Non | F: GGGAATTCAGGGAATAAAGCA (SEQ ID NO: 38) R: CTGTTTGGGGAATGCAGATT (SEQ ID NO: 39) |
| TGF-β1 | 701C>T (SEQ ID NO: 17) | ss104807650 | Coding | Syn | F: CCCTTGCCAAACACTGACA (SEQ ID NO: 40) R: CCTAGCCCAGGCCACTTT (SEQ ID NO: 41) |

TABLE 2

Genotype and allele frequencies of SNPs in candidate genes across three dairy breeds.

| SNP | Genotype | Holstein (N = 484) | | Jersey (N = 80) | | Guernsey (N = 47) | |
|---|---|---|---|---|---|---|---|
| | | Genotype # (%) | Allele % | Genotype # (%) | Allele % | Genotype # (%) | Allele % |
| IL-10 969T > C | TT | 336 (69) | 83[a] | 80 (100) | 100[b] | 47 (100) | 100[b] |
| | CT | 136 (28) | | 0 (0) | | 0 (0) | |
| | CC | 12 (2) | 17 | 0 (0) | 0 | 0 (0) | 0 |
| IL-10Rα 1047C > A | AA | 314 (65) | 81[a] | 17 (21) | 54[b] | 15 (32) | 57[b] |
| | CA | 156 (32) | | 53 (66) | | 24 (51) | |
| | CC | 14 (3) | 19 | 10 (13) | 46 | 8 (17) | 43 |
| IL-10Rα 1398G > A | AA | 93 (19) | 47 | 21 (26) | 58 | 12 (26) | 52 |
| | AG | 266 (55) | | 50 (63) | | 25 (53) | |
| | GG | 125 (26) | 53 | 9 (11) | 43 | 10 (21) | 48 |
| IL-10Rα 1599C > T | CC | 249 (51) | 73[a] | 80 (100) | 100[b] | 47 (100) | 100[b] |
| | TC | 205 (42) | | 0 (0) | | 0 (0) | |
| | TT | 30 (6) | 27 | 0 (0) | 0 | 0 (0) | 0 |
| IL-10Rβ 542C > T | CC | 70 (14) | 39 | 20 (25) | 48 | 11 (23) | 55 |
| | TC | 233 (48) | | 37 (46) | | 30 (64) | |
| | TT | 181 (37) | 61 | 23 (29) | 52 | 6 (13) | 45 |
| TGFβ1 701C > T | CC | 205 (42) | 65[a] | 2 (3) | 15[b] | 25 (53) | 73[a] |
| | CT | 217 (45) | | 20 (25) | | 19 (40) | |
| | TT | 62 (13) | 35 | 58 (73) | 85 | 3 (6) | 27 |

Data is presented as Genotype number (%), genotypic count (frequency); allele % and allelic frequency.

[a,b] differing superscripts indicate a statistically significant (experimental-wise p < 0.01) difference in allele frequencies between breeds for a particular SNP.

TABLE 3

SNP effect on somatic cell score in Canadian Holstein bulls.

| SNP | α ± SE | Pval |
|---|---|---|
| IL-10 969T > C | 0.011 ± 0.031 | 0.712 |
| IL-10Rα 1047C > A | 0.255 ± 0.142 | 0.075 |
| IL-10Rα 1398G > A | 0.254 ± 0.140 | 0.072 |
| IL-10Rα 1599C > T | 0.347 ± 0.141 | 0.015[+] |
| IL-10Rβ 542C > T | 0.029 ± 0.024 | 0.223 |
| TGF-β1 701C > T | −0.009 ± 0.023 | 0.707 |

Data is presented as: α ± SE, allele substitution effect ± standard error; Pval and comparison-wise p-value for the SNP effect.
[+]experimental-wise p < 0.10

TABLE 4

Haplotypes for SNPs 1047C > A, 1398G > A and 1599C > T in IL-10Rα, their frequency in Canadian Holstein bulls and contrasts against the most frequent haplotype (AGC) for somatic cell score.

| IL-10Rα haplotype | | | | | |
|---|---|---|---|---|---|
| 1047C > A | 1398G > A | 1599C > T | Frequency | β ± SE | Pval |
| A | G | C | 40.8% | • | • |
| A | A | T | 16.8% | 0.101 ± 0.03 | 0.003[+] |
| A | A | C | 16.0% | −0.237 ± 0.14 | 0.096 |
| C | A | C | 11.0% | −0.022 ± 0.04 | 0.601 |
| A | G | T | 7.4% | 0.341 ± 0.15 | 0.029 |
| C | G | C | 5.0% | 0.324 ± 0.16 | 0.042 |
| C | A | T | 3.0% | 0.349 ± 0.15 | 0.025 |

Data is presented as: β ± SE, haplotype effect ± standard error; Pval, comparison-wise p-value.
[+]experimental-wise p < 0.10

TABLE 5

Characteristics of SNPs discovered in IL10, IL10Rα/β, TGF-β1, and NRAMP1 genes.

| Gene | SNP | dbSNP ssID | Region | Mutation | Primer set (5'-3') |
|---|---|---|---|---|---|
| IL10 | 1220A>C (SEQ ID NO: 8) | ss104807641 | 5' | | F: GGTAAAGCAGTCCTGAATCCAA (SEQ ID NO: 22) R: TCCTTCATGGGCCCTATTT (SEQ ID NO: 23) |
| | 969T>C (SEQ ID NO: 7) | ss104807640 | 5' | | F: AGCCAGCAGCTCTCAAAGTC (SEQ ID NO: 20) R: GTGTTCAGTGTGGTCCTGGAT (SEQ ID NO: 21) |
| IL10Rα | 1047C>A (SEQ ID NO: 9) | ss104807642 | Coding | Syn | F: TCGTGTTTATTGCTCTGGTTGT (SEQ ID NO: 24) R: CCTGCTTCCTTCCCTCCT (SEQ ID NO: 25) |
| | 1398G>A[a] (SEQ ID NO: 10) | ss104807643 | Coding | Syn | F: GGGTTCCTGCTGGTGACTC (SEQ ID NO: 26) R: GCCAATGCCACTGTCCTC (SEQ ID NO: 27) |
| | 1512C>T[a] (SEQ ID NO: 11) | ss104807644 | Coding | Syn | F: GGGTTCCTGCTGGTGACTC (SEQ ID NO: 28) R: GCCAATGCCACTGTCCTC (SEQ ID NO: 29) |
| | 1599C>T (SEQ ID NO: 12) | ss104807645 | Coding | Syn | F: AGTGCAGACAGCGGGATCT (SEQ ID NO: 30) R: TTCTTCAGGGGTCTGCAAAG (SEQ ID NO: 31) |
| | 1683T>C[a] (SEQ ID NO: 13) | ss104807646 | Coding | Syn | F: AGTGCAGACAGCGGGATCT (SEQ ID NO: 32) R: TTCTTCAGGGGTCTGCAAAG (SEQ ID NO: 33) |
| | 1716A>G[a] (SEQ ID NO: 14) | ss104807647 | Coding | Syn | F: AGTGCAGACAGCGGGATCT (SEQ ID NO: 34) R: TTCTTCAGGGGTCTGCAAAG (SEQ ID NO: 35) |
| IL10Rβ | 542C>T[b] (SEQ ID NO: 15) | ss104807648 | Coding | Non | F: GGGAATTCAGGGAATAAAGCA (SEQ ID NO: 36) R: CTGTTTGGGGAATGCAGATT (SEQ ID NO: 37) |
| | 608A>G[b] (SEQ ID NO: 16) | ss104807649 | Coding | Non | F: GGGAATTCAGGGAATAAAGCA (SEQ ID NO: 38) R: CTGTTTGGGGAATGCAGATT (SEQ ID NO: 39) |
| TGFβ1 | 701C>T (SEQ ID NO: 17) | ss104807650 | Coding | Syn | F: CCCTTGCCAAACACTGACA (SEQ ID NO: 40) R: CCTAGCCCAGGCCACTTT (SEQ ID NO: 41) |

TABLE 5-continued

Characteristics of SNPs discovered in IL10, IL10Rα/β, TGF-β1, and NRAMP1 genes.

| Gene | SNP | dbSNP ssID | Region | Mutation | Primer set (5'-3') |
|---|---|---|---|---|---|
| NRAMP1 | 723C>T (SEQ ID NO: 18) | ss104807654 | Coding | Non | F: TCCTCTGGAGAAGGGAAAGG (SEQ ID NO: 42) R: ATTCAGAGGCAGGAGTCGAG (SEQ ID NO: 43) |
|  | 1139C>G (SEQ ID NO: 19) | ss104807655 | Coding | Non | F: ACATGTGTTGGCCAAGTGAA (SEQ ID NO: 44) R: ACATCCGAGTCCTGAGTGGT (SEQ ID NO: 45) |

NOTE.

SNP, single nucleotide polymorphism; Syn/Non, synonymous, non-synonymous; F/R, forward/reverse primers; IL10, interleukin 10; IL10Rα, interleukin 10 receptor subunit alpha; IL10Rβ, interleukin 10 receptor subunit beta; NRAMP1, natural resistance-associated macrophage protein 1; $^{a,b}$, SNPs with common superscripts are linked ($r^2 \geq 98\%$).

TABLE 6

Genotypic frequencies and associations of SNPs in IL10, IL10Rα/β, TGF-β1, and NRAMP1 genes with MAP infection status.

| Gene | SNP | Genotype | Negative # (%) | Positive # (%) | Effect ± SE | OR (CI) |
|---|---|---|---|---|---|---|
| IL10 | 969T > C | N | 208 | 178 | a: −0.30 ± 0.28 | 0.74 (0.43-1.27) |
|  |  | TT | 163 (78.4) | 136 (76.4) | d: 0.57 ± 0.36 | 1.77 (0.87-3.61) |
|  |  | CT | 34 (16.3) | 37 (20.8) |  |  |
|  |  | CC | 11 (5.3) | 5 (2.8) |  |  |
| IL10Rα | 1047C > A | N | 238 | 193 | a: 0.57 ± 0.31 | 1.77 (0.97-3.25) |
|  |  | CC | 10 (4.2) | 7 (3.6) | d: −0.46 ± 0.35 | 0.63 (0.32-1.25) |
|  |  | CA | 72 (30.3) | 54 (28) |  |  |
|  |  | AA | 156 (65.5) | 132 (68.4) |  |  |
|  | 1398G > A | N | 235 | 183 | a: 0.65 ± 0.21** | 1.92 (1.28-2.89) |
|  |  | AA | 56 (23.8) | 18 (9.8) | d: 0.76 ± 0.23** | 2.13 (1.35-3.38) |
|  |  | AG | 111 (47.2) | 109 (59.6) |  |  |
|  |  | GG | 68 (28.9) | 56 (30.6) |  |  |
|  | 1599C > T | N | 240 | 198 | rm | rm |
|  |  | TT | 18 (7.5) | 5 (2.5) |  |  |
|  |  | TC | 93 (38.8) | 75 (37.9) |  |  |
|  |  | CC | 129 (53.8) | 118 (59.6) |  |  |
| IL10Rβ | 542C > T | N | 216 | 182 | a: 0.21 ± 0.16 | 1.23 (0.90-1.68) |
|  |  | CC | 36 (16.7) | 22 (12.1) | d: 0.14 ± 0.21 | 1.15 (0.76-1.75) |
|  |  | TC | 103 (47.7) | 89 (48.9) |  |  |
|  |  | TT | 77 (35.6) | 71 (39) |  |  |
| TGFβ1 | 701C > T | N | 237 | 201 | a: 0.09 ± 0.15 | 1.10 (0.82-1.47) |
|  |  | CC | 98 (41.4) | 74 (36.8) | d: 0.10 ± 0.20 | 1.10 (0.74-1.65) |
|  |  | CT | 106 (44.7) | 97 (48.3) |  |  |
|  |  | TT | 33 (13.9) | 30 (14.9) |  |  |
| NRAMP1 | 1139C > G | N | 219 | 176 | a: −0.20 ± 0.36 | 0.82 (0.41-1.66) |
|  |  | CC | 142 (64.8) | 106 (60.2) | d: 0.43 ± 0.40 | 1.55 (0.71-3.37) |
|  |  | CG | 71 (32.4) | 67 (38.1) |  |  |
|  |  | GG | 6 (2.7) | 3 (1.7) |  |  |

NOTE.

SNP, single nucleotide polymorphism; # (%), genotypic count (frequency); Effect ± SE, additive (a) or dominance effect (d) ± standard error; OR (95% CI), odds ratio (95% confidence interval); rm, removed to due strong multi-collinearity; IL10, interleukin 10; IL10Rα, interleukin 10 receptor subunit alpha; IL10Rβ, interleukin 10 receptor subunit beta; NRAMP1, natural resistance-associated macrophage protein 1;

**Experimental-wise significance at 5% after logistic regression and Bonferroni's procedure for multiple testing correction.

TABLE 7

Haplotype frequencies in the 3' coding region of IL10Rα gene and their association with MAP infection status.

| IL10Rα haplotype | | | Frequency | | | | |
| --- | --- | --- | --- | --- | --- | --- | --- |
| 1047 C>A | 1398 G>A | 1599 C>T | Negative (n = 235) | Positive (n = 180) | β ± SE | OR (95% CI) | Contrast ± SE |
| A | G | C | 52.6% | 60.6% | 0.35 ± 0.15 * | 1.42 (1.06-1.90) | |
| A | A | T | 27.2% | 20.8% | −0.37 ± 0.17 * | 0.69 (0.49-0.97) | −0.45 ± 0.18 ** |
| C | A | C | 19.1% | 17.8% | −0.09 ± 0.18 | 0.92 (0.65-1.30) | −0.23 ± 0.19 |
| A | A | C | 1.1% | 0.8% | −0.25 ± 0.74 | 0.78 (0.18-3.31) | −0.47 ± 0.74 |

NOTE.
IL1ORα, interleukin 10 receptor subunit alpha; OR, β ± SE, haplotype effect ± standard error; OR (95% CI), odds ratio (95% confidence interval); contrast ± SE, haplotype contrast ± standard error against the baseline, AGC.
* Comparison-wise significance at 5% after logistic regression of haplotype counts against infection status.
** Experimental-wise significance at 5% after logistic regression and Bonferroni's procedure for multiple testing correction.

FULL CITATIONS FOR REFERENCES REFERRED TO IN THE SPECIFICATION

Al-Attiyah R, Mustafa A S. Characterization of human cellular immune responses to novel *Mycobacterium tuberculosis* antigens encoded by genomic regions absent in *Mycobacterium bovis* BCG. Infect Immun 2008 September; 76(9):4190-8.

Ansari-Mahyari S, Berg P (2008) Combined use of phenotypic and genotypic information in sampling animals for genotyping in detection of quantitative trait loci. J. Anim Breed. Genet. 125, 100-109.

Ashwell M S, Heyen D W, Sonstegard T S, Van Tassell C P, Da Y, VanRaden P M, Ron M, Weller J I, Lewin H A (2004) Detection of quantitative trait loci affecting milk production, health, and reproductive traits in Holstein cattle. J Dairy Sci. 87, 4111-4119.

Ates O, Musellim B, Ongen G, Topal-Sarikaya A. Interleukin-10 and tumor necrosis factor-alpha gene polymorphisms in tuberculosis. J Clin Immunol, 2008 May; 28(3): 232-236.

Bannerman D D, Paape M J, Chockalingam A (2006) *Staphylococcus aureus* intramammary infection elicits increased production of transforming growth factor-alpha, beta1, and beta2. Vet Immunol Immunopathol. 112 (3-4), 309-315.

Bannerman D D, Paape M J, Lee J W, Zhao X, Hope J C, Rainard P (2004) *Escherichia coli* and *Staphylococcus aureus* elicit differential innate immune responses following intramammary infection. Clin Diagn Lab Immunol. 11 (1-2), 182-189.

Belsley D A. Conditioning Diagnostics: Collinearity and Weak Data in Regression. 1st ed. N Y, USA: Wiley-Interscience, 1991, 396 pages.

Bingisser R M, Holt P G (2001) Immunomodulating mechanisms in the lower respiratory tract: nitric oxide mediated interactions between alveolar macrophages, epithelial cells, and T-cells. Swiss Med. Wkly. 131 (13-14):171-9.

Bloemhof S, de Jong G, de Haas Y (2008) Genetic parameters for clinical mastitis in the first three lactations of Dutch Holstein cattle. Vet Microbiol. 34(1-2):165-71.

Boettcher P J, Pagnacco G, Stella A (2004) A Monte Carlo approach for estimation of haplotype probabilities in half-sib families. J Dairy Sci. 87, 4303-4310.

Brown K L, Cosseau C, Gardy J L, Hancock R E (2007) Complexities of targeting innate immunity to treat infection. Trends Immunol. 28, 260-266.

Carlen E, Schneider M del P, Strandberg E (2005) Comparison between linear models and survival analysis for genetic evaluation of clinical mastitis in dairy cattle. J Dairy Sci. 88, 797-803.

Cartmell T, Ball C, Bristow A F, Mitchell D, Poole S (2003) Endogenous interleukin-10 is required for the defervescence of fever evoked by local lipopolysaccharide-induced and *Staphylococcus aureus-induced* inflammation in rats. J. Physiol. 549, 653-664.

Chamary J V, Hurst L D. (2005) Evidence for selection on synonymous mutations affecting stability of mRNA secondary structure in mammals. Genome Biol; 6(9):R75.

Couper K N, Blount D G, Riley E M. IL-10: the master regulator of immunity to infection. J Immunol 2008 May 1; 180(9):5771-7.

Chamberlin W, Ghobrial G, Chehtane M, Naser S A. Successful treatment of a Crohn's disease patient infected with bacteremic *Mycobacterium paratuberculosis*. Am J Gastroenterol 2007 March; 102(3):689-91.

Chockalingam A, Paape M J, Bannerman D D (2005) Increased milk levels of transforming growth factor-alpha, beta1, and beta2 during *Escherichia coli*-induced mastitis. J Dairy Sci. 88, 1986-1993.

de Haas Y, Ouweltjes W, ten Napel J, Windig J J, de Jong G (2008) Alternative somatic cell count traits as mastitis indicators for genetic selection. J Dairy Sci. 91, 4860-4870.

Ding Y, Qin L, Zamarin D, et al. Differential IL-10R1 expression plays a critical role in IL-10-mediated immune regulation. J Immunol 2001 Dec. 15; 167(12):6884-92.

Ding Y, Qin L, Zamarin D, Kotenko S V, Pestka S, Moore K W, Bromberg J S (2001) Differential IL-10R1 expression plays a critical role in IL-10-mediated immune regulation. J. Immunol. 167, 6884-6892.

Duan J, Wainwright M S, Comeron J M, et al. Synonymous mutations in the human dopamine receptor D2 (DRD2) affect mRNA stability and synthesis of the receptor. Hum Mol Genet. 2003 Feb. 1; 12(3):205-16.

Feller M, Huwiler K, Stephan R, et al. *Mycobacterium avium* subspecies *paratuberculosis* and Crohn's disease: a systematic review and meta-analysis. Lancet Infect Dis 2007 September; 7(9):607-13.

Fietta A, Meloni F, Francioli C, et al. Virulence of *Mycobacterium tuberculosis* affects interleukin-8, monocyte chemoattractant protein-1 and interleukin-10 production by human mononuclear phagocytes. Int J Tissue React 2001; 23(4):113-25.

Gasche C, Grundtner P, Zwirn P, Reinisch W, Shaw S H, Zdanov A, Sarma U, Williams L M, Foxwell B M, Gangl A (2003) Novel variants of the IL-10 receptor 1 affect inhibition of monocyte TNF-alpha production. J. Immunol. 170, 5578-5582.

Gilmour A R, Gogel B J, Cullis B R, Thompson R (2006) A SRemI User Guide Release 2.0. Hemel Hempstead, UK: VSN International Ltd.

Glasser A L, Darfeuille-Michaud A. Abnormalities in the handling of intracellular bacteria in Crohn's disease: a link between infectious etiology and host genetic susceptibility. Arch Immunol Ther Exp (Warsz) 2008 July; 56(4):237-44.

Goddard M E, Hayes B J (2007) Genomic selection. J Anim Breed Genet. 124 (6):323-30.

Gonda M G, Chang Y M, Shook G E, Collins M T, Kirkpatrick B W. Genetic variation of *Mycobacterium avium* ssp. *paratuberculosis* infection in US Holsteins. J Dairy Sci 2006 May; 89(5):1804-12.

Graffelman J, Camarena J M (2008) Graphical tests for Hardy-Weinberg equilibrium based on the ternary plot. Hum Hered. 65, 77-84.

Halasa T, Huijps K, Osteras O, Hogeveen H (2007) Economic effects of bovine mastitis and mastitis management: a review. Vet Q. 29, 1721-1732.

Hillerton J E, West J G, Shearn M F (1992) The cost of summer mastitis. Vet Rec. 131 (14), 315-317.

Ho A S, Wei S H, Mui A L, Miyajima A, Moore K W. Functional regions of the mouse interleukin-10 receptor cytoplasmic domain. Mol Cell Biol 1995 September; 15(9):5043-53.

Holtsmark M, Heringstad B, Madsen P, Odegard J (2008) Genetic relationship between culling, milk production, fertility, and health traits in Norwegian red cows. J Dairy Sci. 91, 4006-4012.

Karcher E L, Beitz D C, Stabel J R. Modulation of cytokine gene expression and secretion during the periparturient period in dairy cows naturally infected with *Mycobacterium avium* subsp. *paratuberculosis*. Vet Immunol Immunopathol 2008 Jun. 15; 123(3-4):277-288.

Kauf A C, Rosenbusch R F, Paape M J, Bannerman D D (2007) Innate immune response to intramammary *Mycoplasma* bovis infection. J Dairy Sci. 90, 3336-3348.

Khalifeh M S, Stabel J R. Upregulation of transforming growth factor-beta and interleukin-10 in cows with clinical Johne's disease. Vet Immunol Immunopathol 2004 May; 99(1-2):39-46.

Khatkar M S, Thomson P C, Tammen I, Raadsma H W (2004) Quantitative trait loci mapping in dairy cattle: review and meta-analysis. Genet. Sel Evol. 36, 163-190.

Koets A P, Adugna G, Janss L L, et al. Genetic variation of susceptibility to *Mycobacterium avium* subsp. *paratuberculosis* infection in dairy cattle. J Dairy Sci 2000 November; 83(11):2702-8.

Kossaibati M A, Esslemont R J (1997) The costs of production diseases in dairy herds in England. Vet J. 154, 41-51.

Krawetz S A, Womble D D (2003) Introduction to Bioinformatics: A Theoretical and Practical Approach. Humana Press.

Lehner T (2008) Special regulatory T cell review: The resurgence of the concept of contrasuppression in immunoregulation. Immunology. 123(1), 40-44.

Lewis S E, Searle S M, Harris N, Gibson M, Iyer V, Richter J, Wiel C, Bayraktaroglu L, Birney E, Crosby M A, Kaminker J S, Matthews B B, Prochnik S E, Smithy C D, Tupy J L, Rubin G M, Misra S, Mungall C J, Clamp M E (2002) Apollo: a sequence annotation editor. Genome Biol. 3(12), reports0061.

Lewis S E, Searle S M, Harris N, et al. Apollo: a sequence annotation editor. Genome Biol 2002; 3(12):RESEARCH 0082.

Li M O, Flavell R A. Contextual regulation of inflammation: a duet by transforming growth factor-beta and interleukin-10. Immunity 2008 April; 28(4):468-76.

MacDermott R P (1996) Alterations of the mucosal immune system in inflammatory bowel disease. J. Gastroenterol. 31(6), 907-916.

Malo N, Libiger O, Schork N J (2008) Accommodating linkage disequilibrium in genetic-association analyses via ridge regression. Am J Hum Genet. 82(2), 375-385.

McDermid J M, Prentice A M. Iron and infection: effects of host iron status and the iron-regulatory genes haptoglobin and NRAMP1 (SLC11A1) on host-pathogen interactions in tuberculosis and HIV. Clin Sci (Lond) 2006 May; 110 (5):503-24.

McKenna S L, Keefe G P, Tiwari A, VanLeeuwen J, Barkema H W. Johne's disease in Canada part I I: disease impacts, risk factors, and control programs for dairy producers. Can Vet J 2006 November; 47(11):1089-99.

Medzhitov R, Janeway C A, Jr. (1997) Innate immunity: impact on the adaptive immune response. Curr Opin Immunol. 9, 4-9.

Meloun M, Militky J, Hill M, Brereton R G. Crucial problems in regression modelling and their solutions. Analyst 2002 April; 127(4):433-50.

Moore K W, de Waal Malefyt R, Coffman R L, O'Garra A (2001) Interleukin-10 and the interleukin-10 receptor. Annu Rev Immunol. 19, 683-765.

Mortensen H, Nielsen S S, Berg P. Genetic variation and heritability of the antibody response to *Mycobacterium avium* subspecies *paratuberculosis* in Danish Holstein cows. J Dairy Sci 2004 July; 87(7):2108-13.

Murphy M A, Shariflou M R, Moran C. High quality genomic DNA extraction from large milk samples. J Dairy Res 2002 November; 69(4):645-9.

Oviedo-Boyso J, Valdez-Alarcon J J, Cajero-Juarez M, Ochoa-Zarzosa A, Lopez-Meza J E, Bravo-Patino A, Baizabal-Aguirre V M (2007) Innate immune response of bovine mammary gland to pathogenic bacteria responsible for mastitis. J. Infect. 54(4), 399-409.

Pant S D, Schenkel F S, Leyva-Baca I, Sharma B S, Karrow N A. Identification of single nucleotide polymorphisms in bovine CARD15 and their associations with health and production traits in Canadian Holsteins. BMC Genomics 2007; 8,421.

Pyorala S (2002) New strategies to prevent mastitis. Reprod Domest Anim. 37(4), 211-216.

R Development Core Team (2008) R: A language and environment for statistical computing. Vienna, Austria: R Foundation for Statistical Computing.

Reents R, Jamrozik J, Schaeffer L R, Dekkers J C (1995) Estimation of genetic parameters for test day records of somatic cell score. J. Dairy Sci. 78, 2847-2857.

Roque S, Nobrega C, Appelberg R, Correia-Neves M. IL-10 underlies distinct susceptibility of BALB/c and C57BL/6 mice to *Mycobacterium avium* infection and influences efficacy of antibiotic therapy. J Immunol 2007 Jun. 15; 178(12):8028-35.

Rozen S, Skaletsky H. Primer3 on the WWW for general users and for biologist programmers. Methods Mol Biol 2000; 132:365-86.

Rupp R, Boichard D (1999) Genetic parameters for clinical mastitis, somatic cell score, production, udder type traits, and milking ease in first lactation Holsteins. J Dairy Sci. 82(10), 2198-2204.

Rupp R, Boichard D (2003) Genetics of resistance to mastitis in dairy cattle. Vet Res. 34(5), 671-688.

Salomons G S, Bok L A, Struys E A, Pope L L, Darmin P S, Mills P B, Clayton P T, Willemsen M A, Jakobs C (2007) An intriguing "silent" mutation and a founder effect in antiquitin (ALDH7A1). Ann Neurol. 62(4), 414-418.

Salomons G S, Bok L A, Struys E A, et al. An intriguing "silent" mutation and a founder effect in antiquitin (ALDH7A1). Ann Neurol 2007 October; 62(4):414-8.

Sechi L A, Rosu V, Pacifico A, Fadda G, Ahmed N, Zanetti S. Humoral immune responses of type 1 diabetes patients to *Mycobacterium avium* subsp. *paratuberculosis* lend support to the infectious trigger hypothesis. Clin Vaccine Immunol 2008 February; 15(2):320-6.

Shah J H, Maguire D J, Munce T B, Cotterill A (2008) Alanine in H I: a silent mutation cries out! Adv Exp Med. Biol. 614, 145-150.

Sharma B S, Leyva I, Schenkel F, Karrow N A. Association of toll-like receptor 4 polymorphisms with somatic cell score and lactation persistency in Holstein bulls. J Dairy Sci 2006 September; 89(9):3626-35.

Simhan H N, Ryckman K K, Williams S M, Krohn M A. Genetic regulation of cervical antiinflammatory cytokine concentrations during pregnancy. Am J Obstet Gynecol 2008 August; 199(2):163.

Slinker B K, Glantz S A. Multiple regression for physiological data analysis: the problem of multicollinearity. Am J Physiol 1985; 249(1 Pt 2).

Stephens M, Donnelly P. A comparison of bayesian methods for haplotype reconstruction from population genotype data. Am J Hum Genet. 2003 November; 73(5):1162-9.

Tamassia N, Calzetti F, Menestrina N, et al. Circulating neutrophils of septic patients constitutively express IL-10R1 and are promptly responsive to IL-10. Int Immunol 2008 April; 20(4):535-41.

Tamizifar B, Lankarani K B, Naeimi S, Rismankar Z M, Taghavi A, Ghaderi A. Promoter polymorphism of transforming growth factor-beta1 gene and ulcerative colitis. World J Gastroenterol 2008 Jan. 14; 14(2):243-7.

Tedde A, Laura P A, Bagnoli S, et al. Interleukin-10 promoter polymorphisms influence susceptibility to ulcerative colitis in a gender-specific manner. Scand J Gastroenterol 2008; 43(6):712-8.

Tuite A, Gros P (2006) The impact of genomics on the analysis of host resistance to infectious disease. Microbes. Infect. 8, 1647-1653.

Waddell L A, Rajic A, Sargeant J, et al. The zoonotic potential of *Mycobacterium avium* spp. *paratuberculosis*: a systematic review. Can J Public Health 2008 March; 99(2):145-55.

Wei S H, Ming-Lum A, Liu Y, Wallach D, Ong C J, Chung S W, Moore K W, Mui A L (2006) Proteasome-mediated proteolysis of the interleukin-10 receptor is important for signal downregulation. J Interferon Cytokine Res. 26(5), 281-290.

Weiss D J, Evanson O A, de S C, Abrahamsen M S. A critical role of interleukin-10 in the response of bovine macrophages to infection by *Mycobacterium avium* subsp *paratuberculosis*. Am J Vet Res 2005 April; 66(4):721-6.

Winfrey M, Rott M, Wortman A (1997) Unraveling DNA: Molecular Biology for the Laboratory. New Jersey, USA: Prentice Hall.

Zaahl M G, Winter T A, Warnich L, Kotze M J. The −237C→T promoter polymorphism of the SLC11A1 gene is associated with a protective effect in relation to inflammatory bowel disease in the South African population. Int J Colorectal Dis 2006 July; 21(5):402-8.

Zeng Z B, Wang T, Zou W. Modeling quantitative trait Loci and interpretation of models. Genetics 2005 March; 169 (3):1711-25.

Zhu Y, Magnusson U, Fossum C, Berg M (2008) *Escherichia coli* inoculation of porcine mammary glands affects local mRNA expression of Toll-like receptors and regulatory cytokines. Vet Immunol Immunopathol. 125(1-2), 182-189.

---

The invention claimed is:

1. A method of screening for, diagnosing, identifying susceptibility to or detecting a risk of developing mastitis or Johne's disease in a bovine comprising (a) detecting the presence of a SNP comprising an A nucleotide at position 1398 in SEQ ID NO:10 in a sample from the bovine, wherein the SNP is detected using a forward primer comprising the sequence in SEQ ID NO:26 and a reverse primer comprising the sequence in SEQ ID NO:27; and (b) identifying the bovine as having, being susceptible to or having an increased risk of mastitis or Johne's disease if the SNP comprising an A nucleotide at position 1398 in SEQ ID NO:10 is detected.

2. The method of claim 1, wherein the bovine is of the breed Holstein, Jersey or Guernsey.

3. The method of claim 2, wherein the bovine is of the Holstein breed.

* * * * *